US012622637B2

(12) United States Patent
Dunn et al.

(10) Patent No.: US 12,622,637 B2
(45) Date of Patent: May 12, 2026

(54) SYSTEMS AND METHODS FOR PREVENTION OF PRESSURE ULCERS

(71) Applicants: University of Massachusetts, Boston, MA (US); Worcester Polytechnic Institute, Worcester, MA (US)

(72) Inventors: Raymond Dunn, Shrewsbury, MA (US); John McNeill, Worcester, MA (US); Yitzhak Mendelson, Worcester, MA (US); Hamza Abujrida, Everett, MA (US)

(73) Assignees: University of Massachusetts, Boston, MA (US); Worcester Polytechnic Institute, Worcester, MA (US)

( * ) Notice: Subject to any disclaimer, the term of this patent is extended or adjusted under 35 U.S.C. 154(b) by 1006 days.

(21) Appl. No.: 17/340,925

(22) Filed: Jun. 7, 2021

(65) Prior Publication Data

US 2021/0361225 A1     Nov. 25, 2021

Related U.S. Application Data

(63) Continuation of application No. PCT/US2019/065074, filed on Dec. 6, 2019, which is
(Continued)

(51) Int. Cl.
A61B 5/00          (2006.01)
A61B 5/0205        (2006.01)
(Continued)

(52) U.S. Cl.
CPC ............ A61B 5/447 (2013.01); A61B 5/0022 (2013.01); A61B 5/02055 (2013.01);
(Continued)

(58) Field of Classification Search
None
See application file for complete search history.

(56) References Cited

U.S. PATENT DOCUMENTS 5,642,096 A      6/1997  Leyerer et al.
5,862,803 A  *   1/1999  Besson ............... H03F 3/45103
                                                              128/903
(Continued)

FOREIGN PATENT DOCUMENTS

CN      105047259 A    11/2015
CN      106174872 A    12/2016
(Continued)

OTHER PUBLICATIONS

Moon, M., & Lee, S.-K. (2017). Applying of decision tree analysis to risk factors associated with pressure ulcers in long-term care facilities. Healthcare Informatics Research, 23(1), 43-52. (Year: 2017).*

(Continued)

*Primary Examiner* — Niketa Patel
*Assistant Examiner* — Anant A Gupta
(74) *Attorney, Agent, or Firm* — McCarter & English, LLP

(57)          ABSTRACT

Systems, devices, and methods of the present application relate to the diagnostic measurement of condition for pressure ulcers. Preferred embodiments utilize pressure measurements at body locations to determine a diagnostic pressure ulcer value. A pressure sensor device generates patient pressure data that is processed by a data processor which utilizes a diagnostic function to determine the diagnostic value that indicates whether corrective action is needed to prevent pressure ulcer formation. One or more sensor devices can be attached to a patient to measure to transmit data for further processing.

21 Claims, 34 Drawing Sheets

Related U.S. Application Data a continuation-in-part of application No. 16/212,576, filed on Dec. 6, 2018, now Pat. No. 11,911,174, which is a continuation-in-part of application No. PCT/US2017/036208, filed on Jun. 6, 2017.

(60) Provisional application No. 62/346,151, filed on Jun. 6, 2016.

(51) Int. Cl.

| | |
|---|---|
| *A61B 5/021* | (2006.01) |
| *A61B 5/053* | (2021.01) |
| *A61B 5/1455* | (2006.01) |
| *G06N 3/08* | (2023.01) |
| *G06N 20/10* | (2019.01) |
| *G06N 20/20* | (2019.01) |
| *G16H 10/60* | (2018.01) |

(52) U.S. Cl.
CPC ............. *A61B 5/021* (2013.01); *A61B 5/053* (2013.01); *A61B 5/14551* (2013.01); *A61B 5/4872* (2013.01); *A61B 5/4875* (2013.01); *A61B 5/6833* (2013.01); *A61B 5/7264* (2013.01); *G06N 3/08* (2013.01); *G06N 20/10* (2019.01); *G06N 20/20* (2019.01); *G16H 10/60* (2018.01); *A61B 2562/0247* (2013.01); *A61B 2562/0271* (2013.01); *A61B 2562/029* (2013.01); *A61B 2562/164* (2013.01)

(56) References Cited

U.S. PATENT DOCUMENTS

| | | | |
|---|---|---|---|
| 6,030,351 | A | 2/2000 | Schmidt et al. |
| 6,287,253 | B1 | 9/2001 | Ortega et al. |
| 7,090,647 | B2 | 8/2006 | Mimura et al. |
| 7,311,675 | B2 | 12/2007 | Peifer et al. |
| 7,378,975 | B1 | 5/2008 | Smith et al. |
| 7,761,945 | B2 | 7/2010 | Butler |
| 7,798,150 | B2 | 9/2010 | Huber et al. |
| 7,823,219 | B2 | 11/2010 | Freund |
| 8,111,165 | B2 | 2/2012 | Ortega et al. |
| 8,121,800 | B2 | 2/2012 | Altman et al. |
| 8,272,276 | B2 | 9/2012 | Gorjanc et al. |
| 8,416,088 | B2 | 4/2013 | Ortega et al. |
| 8,528,135 | B2 | 9/2013 | Turo et al. |
| 8,535,246 | B2 | 9/2013 | Drennan et al. |
| 8,544,336 | B2 | 10/2013 | Main et al. |
| 8,893,561 | B2 | 11/2014 | Gorjanc et al. |
| 9,076,154 | B1 | 7/2015 | Song et al. |
| 9,220,455 | B2 | 12/2015 | Sarrafzadeh et al. |
| 9,737,263 | B1 | 8/2017 | Kumar et al. |
| 9,833,194 | B2 | 12/2017 | Hayes et al. |
| 10,219,725 | B2 | 3/2019 | Williamson et al. |
| 10,226,187 | B2 | 3/2019 | Al-Ali et al. |
| 10,638,969 | B2 | 5/2020 | Drennan |
| 10,939,850 | B2 | 3/2021 | Roberts et al. |
| 2005/0096513 | A1 | 5/2005 | Ozguz et al. |
| 2005/0165284 | A1* | 7/2005 | Gefen .................... A61B 5/103 |
| | | | 600/557 |
| 2005/0172398 | A1 | 8/2005 | Smith et al. |
| 2006/0085919 | A1 | 4/2006 | Kramer et al. |
| 2007/0038042 | A1 | 2/2007 | Freeman et al. |
| 2007/0232930 | A1 | 10/2007 | Freeman et al. |
| 2008/0278336 | A1 | 11/2008 | Ortega et al. |
| 2009/0143703 | A1 | 6/2009 | Dixon et al. |
| 2009/0234249 | A1 | 9/2009 | Randolph |
| 2010/0162832 | A1 | 7/2010 | Brauers |
| 2010/0324455 | A1 | 12/2010 | Rangel et al. |
| 2011/0068939 | A1 | 3/2011 | Lachenbruch |
| 2011/0263950 | A1 | 10/2011 | Larson et al. |
| 2012/0071743 | A1* | 3/2012 | Todorov ................. A61B 5/486 |
| | | | 600/372 |
| 2013/0006151 | A1 | 1/2013 | Main et al. |
| 2013/0019408 | A1* | 1/2013 | Jacofsky ............... A61B 5/447 |
| | | | 5/613 |
| 2013/0090571 | A1* | 4/2013 | Nourani ................. G16H 50/20 |
| | | | 600/587 |
| 2013/0144751 | A1 | 6/2013 | Gorjanc et al. |
| 2013/0172699 | A1 | 7/2013 | Rebec |
| 2013/0249695 | A1 | 9/2013 | Hann |
| 2013/0281804 | A1 | 10/2013 | Lee et al. |
| 2013/0283530 | A1 | 10/2013 | Main et al. |
| 2013/0332104 | A1 | 12/2013 | Russell |
| 2014/0039351 | A1 | 2/2014 | Mix et al. |
| 2014/0100432 | A1* | 4/2014 | Golda .................... A61B 5/259 |
| | | | 600/595 |
| 2014/0135657 | A1 | 5/2014 | Wu et al. |
| 2014/0200486 | A1 | 7/2014 | Bechtel et al. |
| 2015/0095054 | A1 | 4/2015 | Kaigler et al. |
| 2015/0100135 | A1 | 4/2015 | Ives |
| 2015/0320352 | A1 | 11/2015 | Ben Shalom et al. |
| 2016/0135731 | A1 | 5/2016 | Drennan |
| 2016/0143535 | A1 | 5/2016 | Hyde et al. |
| 2016/0149292 | A1* | 5/2016 | Ganton .............. A61B 5/14532 |
| | | | 29/601 |
| 2016/0228050 | A1* | 8/2016 | Sugla ..................... A61B 5/447 |
| 2016/0249829 | A1 | 9/2016 | Trabia et al. |
| 2016/0256100 | A1 | 9/2016 | Jacofsky et al. |
| 2016/0299021 | A1 | 10/2016 | Thillainadarajah et al. |
| 2016/0319330 | A1 | 11/2016 | Kim |
| 2017/0007153 | A1 | 1/2017 | Tonar et al. |
| 2017/0027498 | A1 | 2/2017 | Larson et al. |
| 2017/0128297 | A1 | 5/2017 | Cernasov et al. |
| 2017/0156658 | A1 | 6/2017 | Maharbiz et al. |
| 2017/0193181 | A1 | 7/2017 | Carter et al. |
| 2017/0245799 | A1* | 8/2017 | Fleischer ............... A61B 5/447 |
| 2017/0273599 | A1 | 9/2017 | Reese et al. |
| 2017/0281073 | A1 | 10/2017 | Drennan et al. |
| 2018/0125412 | A1 | 5/2018 | Ferber |
| 2018/0220953 | A1 | 8/2018 | Burns et al. |
| 2018/0220954 | A1 | 8/2018 | Burns et al. |
| 2018/0220961 | A1 | 8/2018 | Burns et al. |
| 2019/0104982 | A1 | 4/2019 | Dunn et al. |

FOREIGN PATENT DOCUMENTS

| | | |
|---|---|---|
| CN | 106999047 A | 8/2017 |
| WO | 2001/00089 A1 | 1/2001 |
| WO | 2011/097255 A2 | 8/2011 |
| WO | 2015/123157 A1 | 8/2015 |
| WO | 2015/148223 A1 | 10/2015 |
| WO | 2015/187377 A1 | 12/2015 |
| WO | 2016/077310 A1 | 5/2016 |
| WO | 2017/123794 A1 | 7/2017 |
| WO | 2017/176667 A1 | 10/2017 |
| WO | 2018/005108 A1 | 1/2018 |
| WO | 2018/046324 A1 | 3/2018 |
| WO | 2018/071715 A1 | 4/2018 |
| WO | 2018/129631 A1 | 7/2018 |
| WO | 2018/130309 A1 | 7/2018 |
| WO | 2018/144946 A1 | 8/2018 |
| WO | 2019/190378 A1 | 10/2019 |
| WO | 2020/049548 A2 | 3/2020 |
| WO | 2020/233329 A1 | 11/2020 |

OTHER PUBLICATIONS

Anthony et al., Norton, Waterlow and Braden scores: a review of the literature and a comparison between the scores and clinical judgement. J Clin Nurs. Mar. 2008;17(5):646-53.

Batchu et al., Design of a Bio-Impedance Analyzer and Tissue Phantom for Prevention of Pressure Ulcers. A Major Qualifying Project proposal to be submitted to the faculty of Worcester Polytechnic Institute in partial fulfillment of the requirements for the Degree of Bachelor of Science. 163 pages, submitted to faculty on Aug. 14, 2018.

Bluestein et al., Pressure ulcers: prevention, evaluation, and management. American Family Physician. Nov. 15, 2008;78(10):1186-1194.

(56) References Cited

OTHER PUBLICATIONS

Chen et al., Pressure Ulcers Prediction Using Support Vector Machines. 2008 4th International Conference on Wireless Communications, Networking and Mobile Computing. IEEE, 4 pages. Oct. 12-14, 2008.

Crivello et al., Modeling of Force Sensor Nonlinearity for Time-Domain-Based Pressure Measurement in Biomedical Sensors. Northeast Biomedical Engineering Conference, 2 pages, Apr. 2016.

Fergus et al., Collaborative Pressure Ulcer Prevention: An Automated Skin Damage and Pressure Ulcer Assessment Tool for Nursing Professionals, Patients, Family Members and Carers. Cornell University. Retrieved online at: https://arxiv.org/abs/1808.06503. 5 pages, Aug. 17, 2018.

Goodell et al., An In vitro Quantification of Pressures Exerted by Earlobe Pulse Oximeter Probes Following Reports of Device-related Pressure Ulcers in ICU Patients. Ostomy Wound Manage. Nov. 2012;58(11):30-34.

Greff et al., LSTM: A Search Space Odyssey. Transactions on Neural Networks and Learning Systems. 12 pages, Oct. 4, 2017.

Hause et al., Wireless Pressure Ulcer Prevention Device. A Major Qualifying Project submitted to the faculty of Worcester Polytechnic Institute in partial fulfillment of the requirements for the Degree of Bachelor of Science. 105 pages, Apr. 26, 2012.

Hochreiter, Long Short-Term Memory. Neural Computation. Dec. 1997;9(8):1735-1780.

Interlink Electronics, FSR® Force Sensing Resistor®, Integration Guide and Evaluation Parts Catalog. 400 Series Evaluation Parts with Suggested Electrical Interfaces. 26 pages. Retrieved online at: www.sparkfun.com/datasheets/sensors/pressure/fsrguide.pdf, Nov. 23, 2009.

Jindal et al., An adaptive deep learning approach for PPG-based identification. 2016 38th Annual International Conference of the IEEE Engineering in Medicine and Biology Society (EMBC). pp. 6401-6404, Aug. 16-20, 2016.

Kaewprag et al., Predictive models for pressure ulcers from intensive care unit electronic health records using Bayesian networks. BMC Medical Informatics and Decision Making. Jul. 5, 2017;17(Suppl 2):65, 11 pages.

Mcneill et al., Wearable Wireless Sensor Patch for Continuous Monitoring of Skin Temperature, Pressure, and Relative Humidity. 2017 IEEE International Symposium on Circuits and Systems (ISCAS). 4 pages, May 28-31, 2017.

Miao, Simplifying Long Short-Term Memory Acoustic Models for Fast Training and Decoding. IEEE International Conference on Acoustics, Speech and Signal Processing (ICASSP). 5 pages, Mar. 20-25, 2016.

Moore et al., SEM Scanner made easy. Wounds International. Retrieved online at: www.woundsinternational.com. pp. 1-6, Jan. 2018.

Pouyan et al., A Pressure Map Dataset for Posture and Subject Analytics. 2017 IEEE EMBS International Conference on Biomedical & Health Informatics (BHI). pp. 65-68, Feb. 16-19, 2017.

Raizman et al., Utility of a sensor-based technology to assist in the prevention of pressure ulcers: A clinical comparison. Int Wound J. Aug. 2018; 15:1033-44.

Sak et al., Long Short-Term Memory Recurrent Neural Network Architectures for Large Scale Acoustic Modeling. Cornell University, arXiv:1402.1128 [cs.NE]. 5 pages, Feb. 5, 2014.

Sen et al., A New Vision for Preventing Pressure Ulcers. IEEE Pulse. pp. 28-31, Nov./Dec. 2018.

Sen et al., Time-Domain-Based Measurement Technique for Pressure Measurement in a Wearable Wireless Sensor Patch. 2018 IEEE International Symposium on Circuits and Systems (ISCAS). 5 pages, May 27-30, 2018.

Sen et al., Wearable Wireless Pressure Ulcer Prevention System: Validation in a Euthanized Animal Model. 2018 EEE Life Sciences Conference (LSC). 9 pages, Oct. 28-30, 2018.

Sen et al., Wireless Sensor Patch Suitable for Continuous Monitoring of Contact Pressure in a Clinical Setting. 2018 16th IEEE International New Circuits and Systems Conference (NEWCAS). 5 pages, Jun. 24-27, 2018.

Seu et al., The effect of padded adhesive dressing and static body position on sacral interface pressure. PRS Global Open. Abstract 65. 2019. (1 page).

Su et al., Data Mining Techniques for Assisting the Diagnosis of Pressure Ulcer Development in Surgical Patients. J Med Syst. 2012;36:2387-2399. Published online Apr. 19, 2011.

Walia et al., Efficacy of monitoring devices in support of prevention of pressure injuries: systematic review and meta-analysis. Adv Skin Wound Care. Dec. 2016;29(12):567-74.

Wang et al., Portable Gage for Pressure Ulcer Detection. Proc. IEEE Engineering in Medicine and Biology Society Conference. Aug. 2006;1:5997-6000.

Wong et al., Pressure ulcer prevalence and perceptions on prevention: a hospital-wide survey of health professionals. J Wound Care. Apr. 1, 2018;27(Sup4):S29-S35.

Wong, Efficacy of a pressure-sensing mattress cover system for reducing interface pressure: study protocol for a randomized controlled trial. Trials. Sep. 2015;16:434, 11 pages.

Xie et al., A Predictive Model for Force-Sensing Resistor Nonlinearity for Pressure Measurement in a Wearable Wireless Sensor Patch. 61st IEEE International Midwest Symposium on Circuits & Systems (MWSCAS), pp. 476-479, Aug. 2018.

Yousefi et al., A Smart Bed Platform for Monitoring & Ulcer Prevention. 2011 4th International Conference on Biomedical Engineering and Informatics (BMEI). pp. 1362-1366, Oct. 15-17, 2011.

International Search Report and Written Opinion for Application No. PCT/US2017/036208, dated Oct. 11, 2017, 13 pages.

International Search Report and Written Opinion for Application No. PCT/US2019/065074, dated Feb. 19, 2020, 18 pages.

U.S. Appl. No. 16/212,576, filed Dec. 6, 2018, 2019-0104982, Published.

* cited by examiner

Sensor unit
110

Antenna
119

Pressure Sensor
112

Temperature Sensor
116

Temperature Readout circuit
124

Power and Communications Interface
111, 118

Pressure Readout circuit
122

Battery

Sensor unit
110

Sensors or interface electronics

125
Cover

120
Flex-PCB

126
Adhesive

| Average Current | | Value | Units |
|---|---|---|---|
| Sleep | $i_Q$ | 240 | µA |
| Sense | $i_{S(AVG)}$ | | |
| | µC DATA | < 1 | |
| | | 73 | |
| Transmit | $i_{X(AVG)}$ | | |
| | BLE DATA | < 1 | |
| Sensing | | < 1 | |
| Total Current | | 315 | µA |
| Total Power ($V_{DD} = 3.3V$) | | 1.04 | mW |

| RAT ID | Nominal Pressure [mmHg] | Actual Range [mmHg] | Applied Time [Hours] | Size of Pressure Injury [mm] | Epidermal Level Damage | Clinical Ulcer Stage (visual) | Histology Analysis Control Side | Histology Analysis Magnet Side | Muscular Level Damage |
|---|---|---|---|---|---|---|---|---|---|
| 1 | 150 | 240 – 577 | 4 | 13 x 15 | Moderate to severe | 2 | | | Mild |
| 2 | 120 | 130 – 263 | 4 | 13 x 4 | Mild to moderate | 2 | | | Focally mild |
| 3 | 90 | 91 – 186 | 4 | 3 x 3 | Minimal | 2 | | | No visible damage |
| 4 | 60 | 100 – 220 | 6 | 7 x 2 | No visible damage | 2 | | | Minimal thickening |
| 5 | 30 | 60 – 142 | 8 | 7 x 2 | Minimal | 2 | | | No visible damage |

FIG. 17

BRADEN SCALE — For Predicting Pressure Sore Risk

SEVERE RISK: Total score ≤ 9    HIGH RISK: Total score 10-12
MODERATE RISK: Total score 13-14    MILD RISK: Total score 15-18

| RISK FACTOR | SCORE/DESCRIPTION | | | | DATE OF ASSESS ⇧ | | | |
|---|---|---|---|---|---|---|---|---|
| | | | | | 1 | 2 | 3 | 4 |
| SENSORY PERCEPTION Ability to respond meaningfully to pressure-related discomfort | 1. COMPLETELY LIMITED – Unresponsive(does not moan, flinch, or gasp) to painful stimuli due to diminished level of consciousness or sedation, OR limited ability to feel pain over most of body surface | 2. VERY LIMITED – Responds only to painful stimuli. Cannot communicate discomfort except by moaning or restlessness, OR has a sensory impairment which limits the ability to feel pain or discomfort over 1/2 of body. | 3. SLIGHTLY LIMITED – Responds to verbal commands but cannot always communicate discomfort or need to be turned, OR has some sensory impairment which limits ability to feel pain or discomfort in 1 or 2 extremities. | 4. NO IMPAIRMENT – Responds to verbal commands. Has no sensory deficit which would limit ability to feel or voice pain or discomfort. | | | | |
| MOISTURE Degree to which skin is exposed to moisture | 1. CONSTANTLY MOIST – Skin is kept moist almost constantly by perspiration, urine, etc. Dampness is detected every time patient is moved or turned. | 2. OFTEN MOIST – Skin is often but not always moist. Linen must be changed at least once a shift. | 3. OCCASIONALLY MOIST – Skin is occasionally moist, requiring an extra linen change approximately once a day. | 4. RARELY MOIST – Skin is usually dry; linen only requires changing at routine intervals. | | | | |

FIG. 18

| | 1 | 2 | 3 | 4 |
|---|---|---|---|---|
| | | | | |
| | | | | |
| | | | | |
| ACTIVITY Degree of physical activity. | 1. BEDFAST – Confined to bed. | 2. CHAIRFAST – Ability to walk severely limited or nonexistent. Cannot bear own weight and/or must be assisted into chair or wheelchair. | 3. WALKS OCCASIONALLY – Walks occasionally during the day, but for very short distances, with or without assistance. Spends majority of each shift in bed or chair. | 4. WALKS FREQUENTLY – Walks outside the room at least twice a day and inside room at least once every 2 hours during waking hours. |
| MOBILITY Ability to change and control body position | 1. COMPLETELY IMMOBILE – Does not make even slight changes in body or extremity position without assistance. | 2. VERY LIMITED – Makes occasional slight changes in body or extremity position but unable to make frequent or significant changes independently. | 3. SLIGHTLY LIMITED – Makes frequent though slight changes in body or extremity position independently. | 4. NO LIMITATIONS – Makes major and frequent changes in position without assistance |
| NUTRITION Usual food intake pattern [1]NPO: Nothing by mouth. [2]IV: Intravenously. [3]TPN: Total parenteral nutrition | 1. VERY POOR – Never eats a complete meal. Rarely east more than 1/3 of any food offered. Eats 2 servings or less of protein (meat or dairy products) per day. Takes fluids poorly. Does not take a liquid dietary supplement, OR is NPO[1] and/or maintained gn clear liquids or IV[2] for more than 5 days. | 2. PROBABLY INADEQUATE – Rarely eats a complete meal and generally eats only about 1/2 of any food offered. Protein intake includes only 3 servings of meat or dairy products per day. Occasionally will take a dietary supplement OR receives less than optimum amount of liquid diet or tube feeding. | 3. ADEQUATE – Eats over half of most meals. Eats a total of 4 servings of protein (meat, dairy products) each day. Occasionally refuses a meal but will usually take a supplement if offered, OR is on tube feeding or TPN[3] regimen, which probably meets most of nutritional needs. | 4. EXCELLENT – Eats most of every meal. Never refuses a meal. Usually eats a total of 4 or more servings of meat and dairy products. Occasionally eats between meals. Does not require supplementation. |

FIG. 18 (cont.)

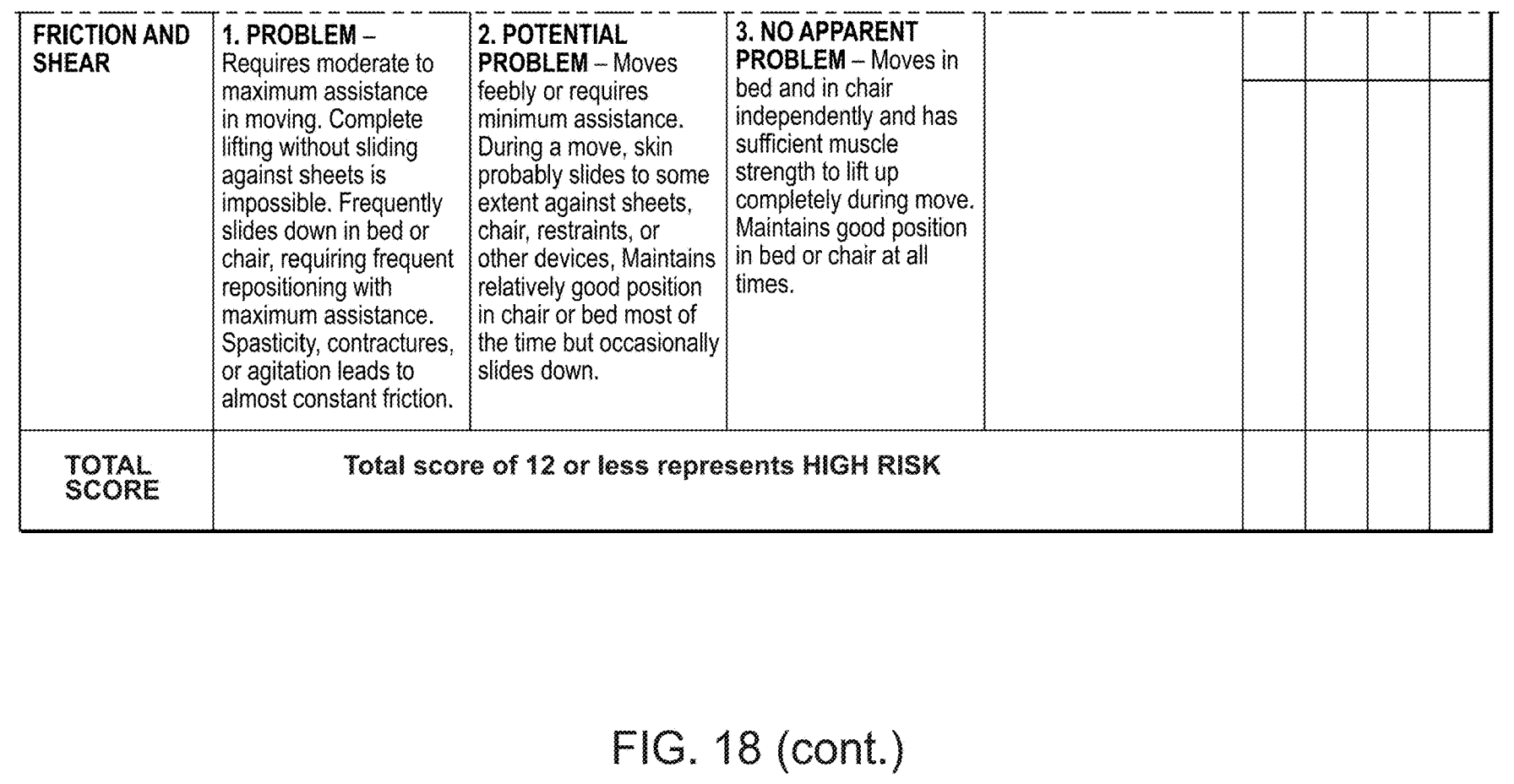

| FRICTION AND SHEAR | 1. PROBLEM – Requires moderate to maximum assistance in moving. Complete lifting without sliding against sheets is impossible. Frequently slides down in bed or chair, requiring frequent repositioning with maximum assistance. Spasticity, contractures, or agitation leads to almost constant friction. | 2. POTENTIAL PROBLEM – Moves feebly or requires minimum assistance. During a move, skin probably slides to some extent against sheets, chair, restraints, or other devices, Maintains relatively good position in chair or bed most of the time but occasionally slides down. | 3. NO APPARENT PROBLEM – Moves in bed and in chair independently and has sufficient muscle strength to lift up completely during move. Maintains good position in bed or chair at all times. | |
|---|---|---|---|---|
| TOTAL SCORE | Total score of 12 or less represents HIGH RISK | | | |

FIG. 18 (cont.)

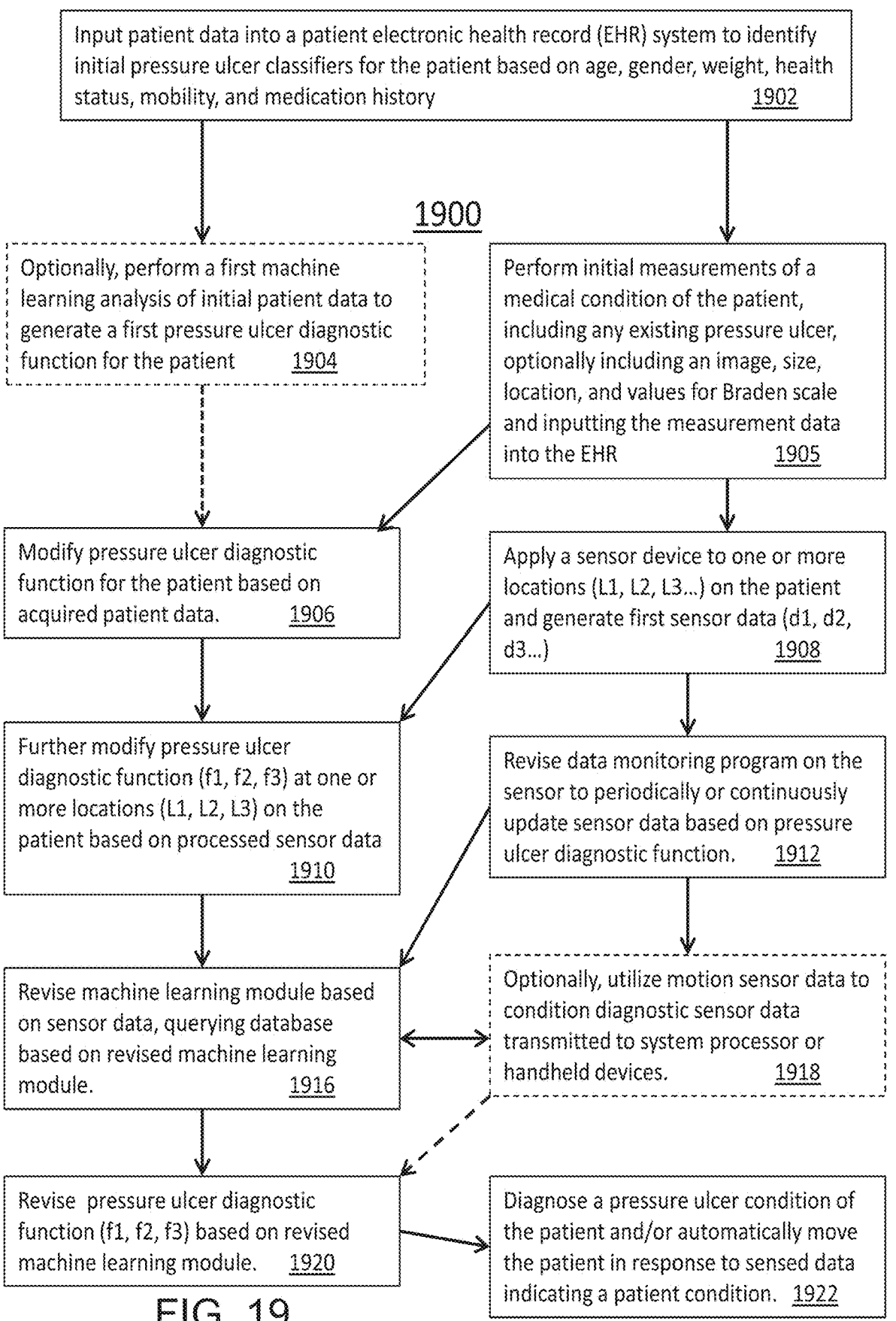

Input patient data into a patient electronic health record (EHR) system to identify initial pressure ulcer classifiers for the patient based on age, gender, weight, health status, mobility, and medication history                    1902

1900

Optionally, perform a first machine learning analysis of initial patient data to generate a first pressure ulcer diagnostic function for the patient        1904

Perform initial measurements of a medical condition of the patient, including any existing pressure ulcer, optionally including an image, size, location, and values for Braden scale and inputting the measurement data into the EHR                    1905

Modify pressure ulcer diagnostic function for the patient based on acquired patient data.        1906

Apply a sensor device to one or more locations (L1, L2, L3...) on the patient and generate first sensor data (d1, d2, d3...)                    1908

Further modify pressure ulcer diagnostic function (f1, f2, f3) at one or more locations (L1, L2, L3) on the patient based on processed sensor data                    1910

Revise data monitoring program on the sensor to periodically or continuously update sensor data based on pressure ulcer diagnostic function.        1912

Revise machine learning module based on sensor data, querying database based on revised machine learning module.                    1916

Optionally, utilize motion sensor data to condition diagnostic sensor data transmitted to system processor or handheld devices.        1918

Revise  pressure ulcer diagnostic function (f1, f2, f3) based on revised machine learning module.        1920

Diagnose a pressure ulcer condition of the patient and/or automatically move the patient in response to sensed data indicating a patient condition.  1922

FIG. 19

SYSTEMS AND METHODS FOR PREVENTION OF PRESSURE ULCERS

RELATED APPLICATION

This application is a continuation of International Patent Application PCT/US2019/065074, filed Dec. 6, 2019, which is a continuation-in-part of U.S. patent application Ser. No. 16/212,576, filed Dec. 6, 2018, which is a continuation-in-part of International Patent Application PCT/US2017/036208, filed Jun. 6, 2017, which claims priority to U.S. Provisional Application 62/346,151, filed Jun. 6, 2016, the entire contents of each of these applications being incorporated herein by reference.

BACKGROUND OF THE INVENTION

A pressure ulcer, commonly referred to as a bed sore, is defined as a breakdown of the skin due to a lack of blood flow and often results in an increase in pressure on boney prominences. The most common locations of pressure ulcers are on the back of the heels, the backbone, and the shoulder blades although pressure ulcers can form in nearly any location on the body. There are millions of cases of pressure ulcers in the world each year, and 2.4 million cases were recorded in the United States alone in 2007. There are substantial costs for the treatment of a single pressure ulcer, and, in some cases, insurers have indicated that they will no longer reimburse hospitals for the treatment of pressure ulcers as they are classified as a preventable problem.

Other than periodic patient movement, there are currently no methods in general use for preventing pressure ulcers. The current standard of care has clinicians taking preventative measures to help decrease the likelihood of forming pressure ulcers based on clinical practice guidelines. Existing approaches have utilized sensors integrated into patient supports such as tables or beds. However, when the patient is turned, the measurement is disrupted so that the cumulative impact of pressure over time is not considered. When these measures fail, ulcers are diagnosed and treated based on a scale of severity. All too often, the preventative measures are not effective enough to prevent pressure ulcers at an early stage thereby creating a need for costly and painful treatment of the ulcers. Further improvements in the diagnostic assessment of pressure ulcer formation are needed.

SUMMARY OF THE INVENTION

The present invention relates to devices and methods for detecting the formation of pressure ulcers. Preferred embodiments utilized measured sensor data that is processed to determine a diagnostic value indicative of pressure ulcer formation. A sensor device in accordance with such embodiments can include at least one pressure sensor and a processing device that receives pressure data and processes this data using a diagnostic function to determine whether the patient or their caregiver should take action to avoid injury. As the conditions under which pressure ulcers will occur in a given patient depend on the specific condition of that patient, simply measuring the pressure applied at any instant to the skin of a patient does not provide meaningful information that is useful to the patient or caregiver. A particular pressure measurement at a particular time, for example, may indicate that no action is needed or that immediate corrective action is necessary both of which can be false depending on the circumstances. In conventional systems, time domain based measurements to determine the accumulated effects at a selected location on a patient's body are not available.

Preferred embodiments employ a number of patient specific attributes that are used to determine a diagnostic function for each individual patient. Patient attributes can include one or more body locations at which pressure is being measured, the weight or body mass of the patient as well as the age, medical condition, medical history, mobility, nutrition, blood oxygenation, blood pressure, temperature and other factors impacting diagnostic assessment. The diagnostic function provides a quantitative analysis to indicate to the user that a patient is at low or high risk of ulcer formation, for example. The diagnostic function can be the sum of weighted parameters, each parameter having a coefficient to define the weight given to the respective parameter, for example, or another analytic expression can be used that enables accurate computation of a quantitative diagnostic value over time. A location on the heel of a patient having peripheral vascular disease, for example, will have a substantially lower threshold than a location on a shoulder of a healthy child. In some embodiments, the diagnostic function can include a machine learning module that can comprise a Bayesian statistical data integration algorithm, for example.

A preferred embodiment can employ a conformable sensor patch that can be fixedly attached to one or more body locations of a particular patient. The device can include a wireless transmitter, a data processor, a power source such as a battery, and one or more sensor elements such as a pressure sensor or array of sensors, a bioimpedance sensor, a temperature sensor, a moisture sensor, an acceleration sensor, a motion sensor, and/or a light sensor. The processor can be programmed to determine a diagnostic value based on the measured data and communicate this value to the patient or other user. The sensor device is attached to the skin of the patient at specific body location(s) to perform time domain measurements to provide continuous or periodic measurements. The pressure sensor can be triggered to actuate device operation when a threshold pressure level is sensed for a preset time period or when the pressure reaches a level that could cause an impact injury, such as the patient falling. Pressure ulcer injury often occurs with the occlusion of microvasculature between a bone and a region of skin under pressure. Sustained oxygen deprivation of tissue arising from vascular occlusion over days or weeks can eventually cause ulcer formation. Triggering based upon pressure measurements can limit consumption of battery power by actuating device operation only during those times when a particular body location is subject to a pressure that can contribute to pressure ulcer formation. The device can also be activated by receipt of wired or wireless transmission of data by an onboard receiver that receives diagnostic data (e.g. blood pressure, blood oxygenation) from a separate sensor device.

Preferred embodiments can utilize the wireless communication of the sensor device to deliver the measured or processed data to a local communication device such as a cellular phone, a tablet or other computing device in proximity with the sensor. Alternatively, the device can directly communicate such data to a remote receiver, server or other networked computing device for further processing or storage, such as an electronic medical record as described herein. Data can be processed onboard the sensor device or on the local device, or remotely or combinations thereof.

For many patients, a plurality of locations on the body need to be monitored over time with each location having different criteria to measure and characterize risk. Thus, a preferred embodiment tracks different sensor units at different locations that integrate data over time for that specific patient for each of the body locations separately. Each location can have a sensor unit that comprises an array of pixel sensor elements distributed over a surface area of the skin. The pixel array can have sub-regions corresponding to sub-arrays of pixel elements that can be processed together as a unit, such as by averaging, or as individual pixel elements. Each pixel element can have a surface area in a range of 0.2 to 2.0 square centimeters, and preferably in the range of 0.5-1 square centimeter.

Embodiments can include a mobile device such as an internet enabled mobile phone or tablet that provides a handheld unitary interface for control of one or more sensor devices that are positioned on a patient. A tablet, for example, can include a near field sensing device or other machine code reader that detects a code, or communicates with a pressure sensor device or patch being activated for use with a particular patient. This both initiates the pressure sensor device and actuates the tablet user interface to record usage and display data. A patient identifier can be stored in a patch memory and a patch identifier can be stored in the tablet as being associated with a particular patient. A password protected patient record can be accessed through a web browser or other Internet portal at a clinic, hospital or a physician's office, a caregiver can thereby communicate remotely with the patient and view a sensor placement or injury via a camera on the mobile device. The tablet has a plurality of pull down menus and fields for data entry and display including patient data entry fields and one or more display windows to display sensor data as it is recorded and/or processed. The display windows can separately display sensor device parameters, or within each sensor device display window can display parameter presets or user adjustable parameters such as thresholds for different sensor outputs. For example, the minimum sensor threshold for sensed pressure for each patch, or for selected pixel elements in a sensor array, can be separately operated by finger actuated touch gestures on the touch screen.

Alternatively, a user can employ a mouse or other cursor control device to manipulate the graphical user interface (GUI) of the tablet. The displayed data window for each patch can have separate touch actuated menus to display different data sets or graphical features for each body location. The GUI can display the diagnostic function for a particular sensor device, can display traces of the individual sensor element data in real time, and display scoring data to indicate the condition of the location(s) being monitored. A caregiver can conduct a video conference with a remotely located patient to discuss and view sensor position and any condition.

Different body locations can be individually controlled via the unitary control interface. Two or more locations can be linked, such as a first patch on the left heel and a second patch on a right heel of a patient, as they can be indicating similar conditions and have similar therapeutic indications. A plurality of patients can be monitored with a single device by selecting a particular patient to then display one or more patches that are operating on the selected patient at one time. Prior data sets can also be retrieved for each patient and data correlations computed for each dataset. For sensor arrays, pressure distributions can be displayed to identify particular regions requiring further monitoring or treatment. Image processing can be used to further characterize and quantify characteristics of a particular ulcer location.

The system can be linked to an automated patient movement device that can indicate to the patient that they must move and/or can cause the required movement under condition where the patient is immobilized, asleep or medicated.

BRIEF DESCRIPTION OF THE DRAWINGS

FIG. 17 is a table showing results of animal protocol measurements.

FIG. 18 illustrates the Braden scale for scoring and describing patient data variables.

FIG. 19 illustrates a flowchart of a technique to diagnose a pressure ulcer condition of a patient in accordance with various embodiments described herein.

DETAILED DESCRIPTION OF THE INVENTION

Embodiments of the present invention relate to systems and methods for prevention or mitigation of pressure ulcers. The systems and methods taught herein include sensors attached to sites on a patient that may be prone to development of pressure ulcers. Data collected by the sensors can be used in combination with patient-specific data to determine the risk of development of a pressure ulcer at the site. In various embodiments, the data can be collected and processed directly by the sensors, by a local computing device such as a handheld tablet, Internet enabled cellular phone or smartphone, or by a remote computing device.

A pressure ulcer is a localized injury to the skin and/or underlying tissue usually over a bony prominence as a result of pressure alone or in combination with shear and/or friction. Although direct measurements of pressure are an important component of determining risk to develop a pressure ulcer, the risk also strongly depends on other environmental variables such as temperature and humidity and patient-specific data such as age and mobility level. Systems and methods taught herein can adjust a diagnostic function, such as a risk model, based on historical measurements of environmental variables and patient-specific data. In some embodiments, the systems and methods taught herein can generate a patient-specific risk model from accumulated patient data using a neural network or support vector machine to create a supervised learning model. The diagnostic function can comprise a weighted combination of variables for a specific patient or for defined classes of patients. Sensor devices can be placed at a plurality of different locations on the body such that the different sensors can have different diagnostic functions based on known correlations between a body location and the likelihood of generating on ulcer at that location for a particular patient. Exemplary diagnostic functions can comprise a plurality of attributes or classifiers that meet certain operating thresholds or ranges that can be weighted to reflect their relative importance in computing the diagnostic state of the patient at a point in time. Existing approaches have failed to provide the localized measurements needed to accurately situate where a patient is at a point in time in terms of the risk of developing a pressure ulcer.

As used herein, "integration of measurement data" includes computation of a mathematical integral or summation of measurement data over time or alternatively, can include functional treatments of measurement data over time including nonlinear techniques, moving averages, apodization, interpolation, and discrete sampling, for example.

Figure 1:
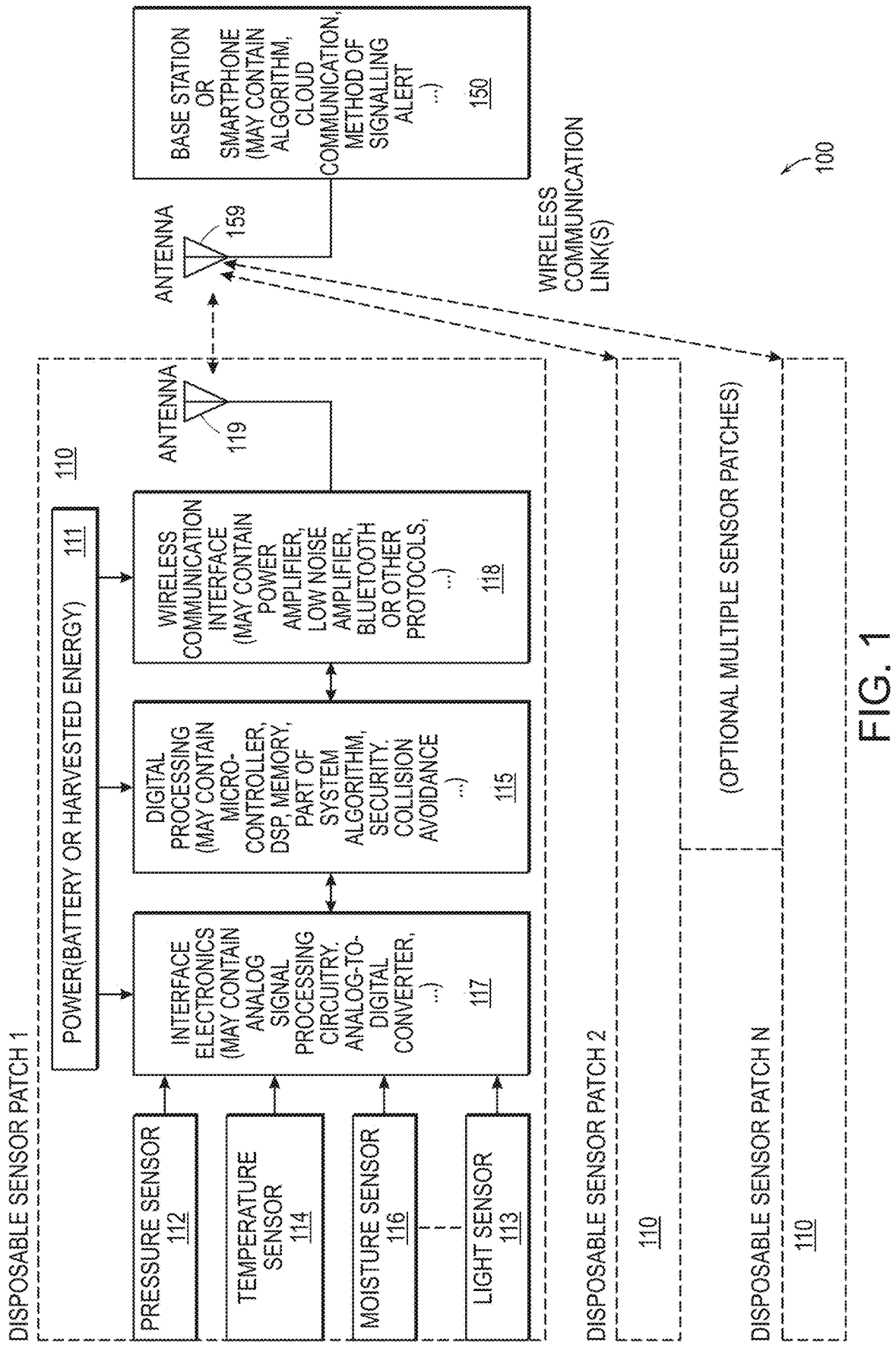
FIG. 1 illustrates a schematic of a system for prevention of pressure ulcers in accordance with some embodiments of the present disclosure.

FIG. 1 illustrates an embodiment of a pressure ulcer monitoring system 100 that includes one or more sensor devices 110 and a base station 150. The sensors 110 can be in communication with the base station 150 to transmit or receive data. Base station 150 can be a bedside monitoring system that monitors one or more sensors including blood pressure or blood oxygenation or can be a personal communication device of the patient.

The sensor devices 110 can include a one or more of a power source 111, a pressure sensor 112, a moisture sensor 116, a temperature sensor 114, an acceleration sensor, such as a microelectromechanical (MEMS) motion sensor, a light sensor 113, interface electronics 117, digital processing 115, a communications interface 118, and an antenna 119. The sensor devices 110 can be attached to a patient at any location on the body or, more preferably, at locations on the body that are prone to developing a pressure ulcer. For example, sensor devices may be affixed to a patient that primarily uses a wheelchair on the heels of the feet, the sides of the legs, the buttocks, or any other place that commonly comes into contact with the wheelchair. The sensor device 110 may include an adhesive layer in some embodiments to enable fixation to the patient's body. The adhesive can include a biodegradable or bioabsorbable polymer, hydrogel or acrylate ester/vinyl pyrrolidone copolymers, dimethyl silicone polymers, and acrylate polymers, for example. In other embodiments, the sensor device 110 can be affixed to the patient using externally applied adhesive (e.g., tape) or a fabric sleeve/sock that positions the sensor device or sensor array on a fixed tissue surface location such that movement of the patient does not alter the position of the sensor relative to the patient. In some embodiments, the sensor devices 110 are disposable or sterilizable. In some embodiments, the sensor devices 110 are waterproof or water-resistant to prevent damage to internal components of the sensor device 110 in a clinical setting. The patient can wear the sensor devices 110 without replacement in some embodiments for 1 to 14 days or more, preferably for between 3 and 7 days. In some embodiments, the sensor device 110 can be a conformable patch that is disposable, or alternatively, utilizes a reusable electronic package positioned within a disposable sleeve.

The pressure sensor 112 can produce an output signal that is proportional to the pressure applied to the sensor device 110. The pressure sensor 112 can be adapted to measure pressures in a range from 0 mmHg to 350 mmHg in various embodiments. Each sensor device 110 can include more than one pressure sensor 112 in some embodiments. The use of more than one pressure sensor 112 can enable spatially-resolved pressure measurements within a single sensor device 110. The sensor device 110 can include interface electronics 117 to convert or calibrate the signal provided by the pressure sensor 112 to a format suitable for output by the communications interface 118. The interface electronics can include power management as well as data transmission and reception with interface 118 as described herein. The power management circuit must efficiently allocate available power to the sensor elements, and the data processing and transmission functions. In some embodiments, the pressure sensor 112 can include a polymer thick-film device that exhibits a change in electrical resistance as the force applied to the device changes. In some embodiments, the pressure sensor 112 can include a capacitive sensor that produces a change in output signal when the capacitance between two surfaces across a dielectric material changes. In some embodiments, the pressure sensor 112 can include an FSR 402 resistive force sensor (Interlink Electronics, Westlake Village, California). Embodiments of the pressure sensor 112 are described in greater detail below.

The power source 111 of the sensor device 110 can include a battery in some embodiments. The battery can be single-use or rechargeable. In some embodiments, the battery can be a polymer battery that can be formed on the sensor substrate. In embodiments where the battery is rechargeable, the sensor device 110 may include additional circuitry to receive inductive or RF power from an external source to recharge the power source 111. In some embodiments, the power source 111 can include an energy-harvesting mechanism to recharge the power source 111 by capturing kinetic energy produced by patient movement. The energy-harvesting mechanism can include MEMS accelerating weights in some embodiments. The power source 111 can provide power to the electrical components of the sensor device 110 such as the digital processing 115, communications interface 118, or interface electronics 117.

The temperature sensor 114 and moisture sensor 116 can provide output signals correlated to temperature and relative humidity, respectively. In some embodiments, the sensor device 110 can include interface electronics 117 to convert or calibrate the signals from the temperature sensor 114 or the moisture sensor 116 to a format suitable for output by the communications interface 118. In some embodiments, the output from the temperature sensor 114 can be used to calibrate the output signal obtained from the pressure sensor 112. In an exemplary embodiment, the temperature sensor 114 and the moisture sensor 116 can exist together in a single package. For example, the SHT3x-ARP (Sensirion AG, Staefa, Switzerland) can be used which has the benefits of relatively low cost, acceptable size, and high relative humidity and temperature sensor accuracies.

The sensor device 110 is not limited to including the sensor types described thus far. In some embodiments, the sensor device 110 can include additional sensors to measure other physical or chemical properties in the patient. For example, the sensor device 110 can include a light sensor 113 (e.g., photodiode or other photosensor) or other suitable sensor to detect light reflected or emitted from the skin of the patient. In embodiments with a light sensor 113, the sensor device 110 can also include a light source such as an LED or LED array having one or more emission wavelengths. The light sensor 113 can generate colorimetric data corresponding to a color of the skin of the patient. Hyperemia can be an early predictor of formation of a pressure ulcer and can manifest as a reddening of the skin. Blue, black, or green coloration of tissue can also be indicative of imminent or ongoing damage to the tissue. In some instances, colorimetric data may be indicative of restricted or altered blood flow in the tissue and thus can be predictive of risk for pressure ulcer development. In some embodiments, the light sensor 113 can be a component of a pulse oximeter.

In some embodiments, the sensor device 110 can include sensing elements for any suitable chemical or physical parameter of tissue or the surrounding environment. For example, the sensor device 110 can include a component to directly measure blood flow in tissue such as an ultrasound transducer device or a laser Doppler device.

The communications interface 118 of the sensor devices 110 can include appropriate electronics to transmit and receive data including power amplifiers or low-noise amplifiers. In various embodiments, the communications interface 118 can communicate through a wired or wireless interface. In wireless embodiments, the communications interface 118 can communicate using protocols or standards associated with 802.11x (wi-fi), BLUETOOTH®, or any other suitable wireless technology standard. This provides for the packetized aggregator and transmission of data that is clocked by circuitry residing on the sensor device. The sensor circuitry can enter the sensed data in a given clock cycle into individual fields of each packet that can include a patient ID, a sensor ID, a time stamp, a body location and a data field for each sensor element, for example. The sensor device can also receive and process packets of the information by wireless transmission from the host computer which can include one or more data fields for the diagnostic function for the patient and sensor device including time stamp, body location, calibration data, etc.

In some embodiments, the sensor device 110 can include digital processing 115 to perform various functions. For example, the digital processing 115 can include a microcontroller, a data processor, a digital signal processor, ASIC, memory, security architecture to encrypt data in accordance with patient data privacy protocols, collision avoidance architecture, or at least a portion of processor-executable code to generate a pressure ulcer diagnostic value indicative of a risk assessment using measurement data and patient-specific data. The memory can have both non-volatile and volatile memory components which can be used in some embodiments to store processor-executable code to control device operation and store or process the measured data. In some embodiments, the sensor device 110 can store measurement data in the memory and specifically if the connection between the communications interface 118 of the sensor device 110 and an external device is interrupted. The stored measurement data can be transmitted at a later time when the connection is re-established. In some embodiments, the digital processing module(s) 115 of the sensor device 110 can self-diagnose the sensor device's readiness state and report (using the communications interface 118) if one or more components of the sensor device 110 have failed or not functioning in accordance with specifications. Alternatively, the device can have a simplified configuration to automatically stream data to an external device by wired or wireless connection.

The pressure ulcer monitoring system 100 also can include a base station 150. In some embodiments, the base station 150 can be a computing device or mobile communications device such as a tablet or smartphone. The base station 150 can include a processor, memory, communications interface, an alert module, an antenna 159, and at least a portion of processor-executable code to generate a pressure ulcer risk assessment using measurement data and patient-specific data. In some embodiments, the base station 150 can be located within range of wireless communication with the sensor devices 110 or can be located distantly. In some embodiments, the base station 150 can communicate with the sensor devices 110 through an intervening communications network such as the Internet or a local area network (LAN).

Figures 2A, 2B:
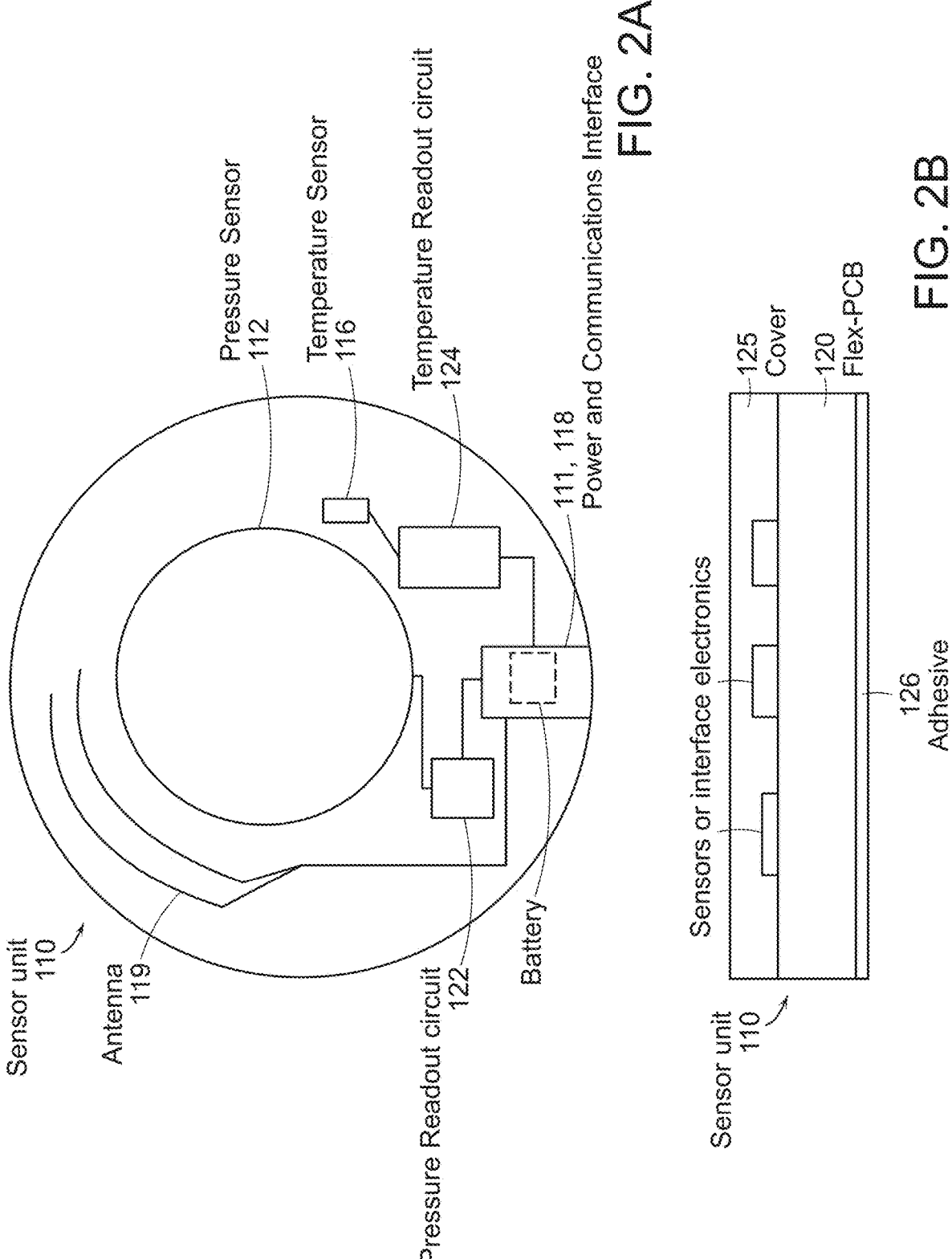
FIGS. 2A and 2B illustrate top and side views of a sensor device in accordance with some embodiments of the present disclosure.

FIGS. 2A and 2B illustrate top and side views of a sensor device 110 according to some embodiments of the present disclosure. The sensor device 110 can include a printed circuit board 120 onto which various components are mounted. The sensor device 110 can include the pressure sensor 110, the temperature sensor 114, interface electronics 117 such as a pressure readout circuit 122 or a temperature readout circuit 124, the power source 111, communications interface 118, and the antenna 119. The sensor device 110 can include a layer of adhesive 126 to enable the device to be affixed to a patient. In some embodiments, the printed circuit board 120 is a flexible printed circuit board (flex-PCB).

Because the sensor device 110 can be situated between the patient and bearing surface that threatens to create a pressure ulcer (for example, affixed directly to the tissue surface of the patient), it is important that the sensor device 110 itself not contribute to causing a pressure ulcer. In some embodiments, the sensor device 110 can include a cover 125. In certain embodiments, the cover 125 can have a uniform or flat external surface to prevent concentration of pressure or force on the patient due to the size and rigidity of certain internal components of the sensor device 110 such as the discrete components or chips. In some embodiments, the cover 125 can be molded onto the flex-PCB 120. In some embodiments, the cover 125 can seal the sensor device 110 to prevent moisture infiltration. The cover can provide a thin, pliable, conformable sensor device in which the opposite sides are aligned and the thickness is less than 4 mm, and preferably less than 3 mm and further preferably less than 2 mm. The sensor device or patch has an area less than 4 cm$^2$ and will preferably be rectangular circular or oval in shape.

Figure 3:
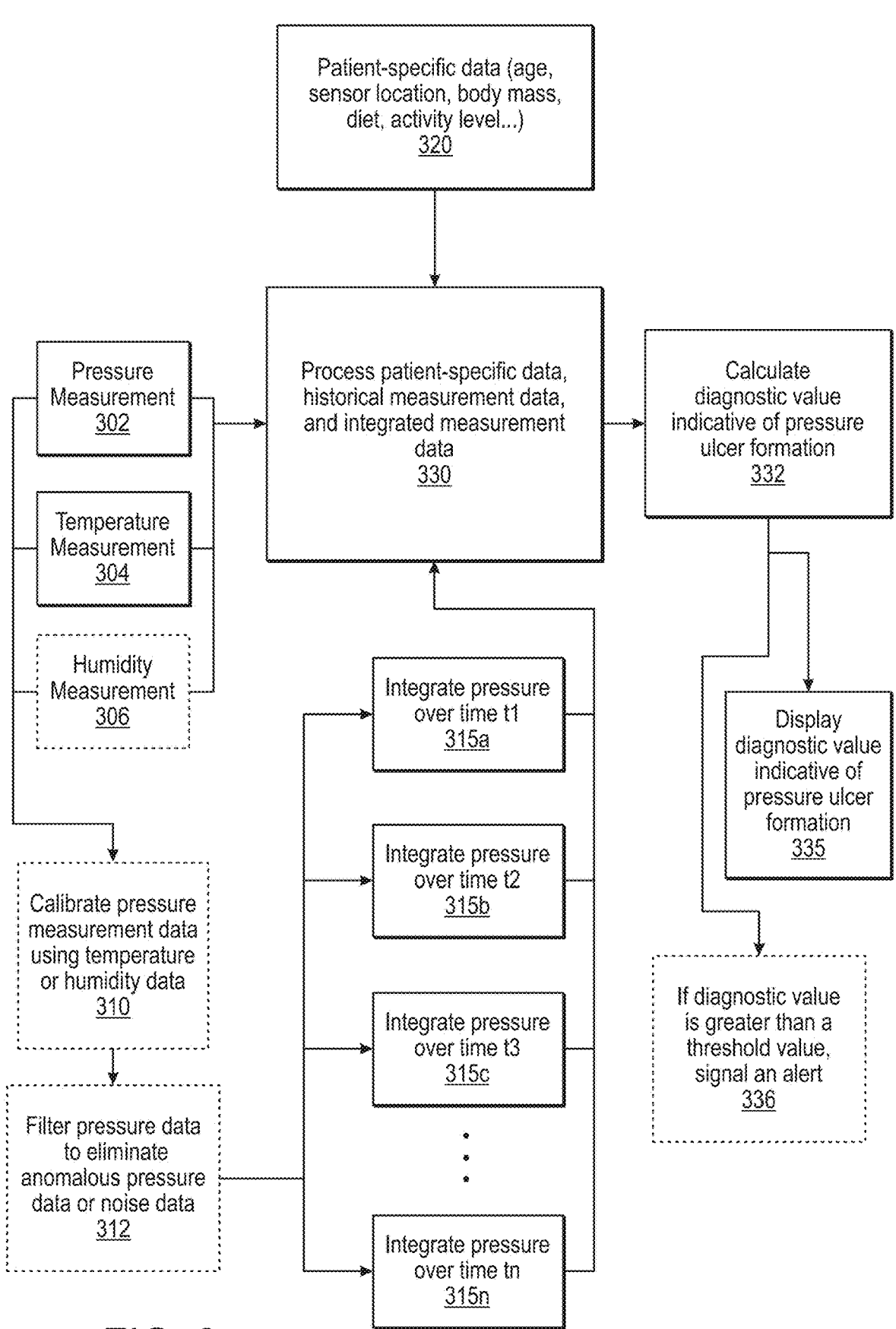
FIG. 3 illustrates a schematic flowchart of the calculation of a value indicative of pressure ulcer formation a schematic of a method for calculating a value indicative of pressure ulcer formation in accordance with some embodiments of the present disclosure.

FIG. 3 illustrates a schematic flowchart of a procedure to evaluate risk of pressure ulcer formation using current and historical measurement data and patient-specific data in accordance with various embodiments of the present disclosure. The procedure can process 330 integrated and historical measurement data such as pressure measurements 302, temperature measurements 304, and humidity measurements 306, measured physiological states such as blood oxygenation or blood pressure, and other patient-specific data 320. The procedure uses the processed data to calculate one or more pressure ulcer diagnostic values indicative of pressure ulcer formation 332. The procedure can manipulate the pressure measurement data by optionally calibrating the data using the temperature data, the humidity data, or both 310 or by filtering the pressure measurement data over time using a filter to eliminate anomalous pressure data or noise 312. The procedure can integrate the pressure data over different time periods 315*a* . . . 315*n*. The procedure can display the pressure ulcer diagnostic value indicative of pressure ulcer formation 335 at each location. If the pressure ulcer diagnostic value is greater than a threshold value, for example, the procedure can signal an alert 336.

In some embodiments, the pressure ulcer diagnostic value indicative of pressure ulcer formation can be a probability value. In some embodiments, the probability value can be provided with confidence intervals.

In some embodiments, signaling the alert can include activating an alarm or displaying a warning on a display. In some embodiments, the alert can include actionable information including, but not limited to, suggestions to offload pressure from the area, move the patient, alter a movement regimen, change patient bedding, or other appropriate information. In some embodiments, signaling the alert can include providing feedback to a computerized bed, wheelchair, or an Internet of Things (TOT) device involved with patient care or positioning. Upon receipt of the alert, the bed, wheelchair, or IOT device can then directly move the patient from a particular position until the pressure ulcer monitoring system 100 indicates that appropriate pressure relief had occurred at the affected site. By directly communicating alert status related to a specific location on the patient to the computerized bed, wheelchair, or IOT device such as a patient harness, systems and methods described herein can fully automate healthcare by removing the need for a human healthcare provider or helper from the care path to arrive to alleviate the patient. In various embodiments, the computerized bed can be a hospital bed, a nursing home bed or a motorized residential bed. In some embodiments, the wheelchair can be a multipositional electronic and/or motorized wheelchair.

Patient-specific data 320 can include any data that may impact diagnostic assessment for development of a pressure ulcer. Examples of patient-specific data include, but are not limited to, patient age, mobility level, weight, nutrition level, history of smoking, medication history (type, dosage, and schedule), medical history (e.g, heart disease, hypertension, or peripheral vascular disease), and blood pressure. In some embodiments, patient-specific data can include prior evaluations of a patient's risk for developing a pressure ulcer (e.g., output from a patient evaluation using the Braden, Waterlow, or Norton scales). Some patient-specific data is also specific to a measurement site such as location of the measurement site (e.g., heel, buttocks, back, leg, etc.), blood oxygenation level, and/or skin temperature.

Figure 4:
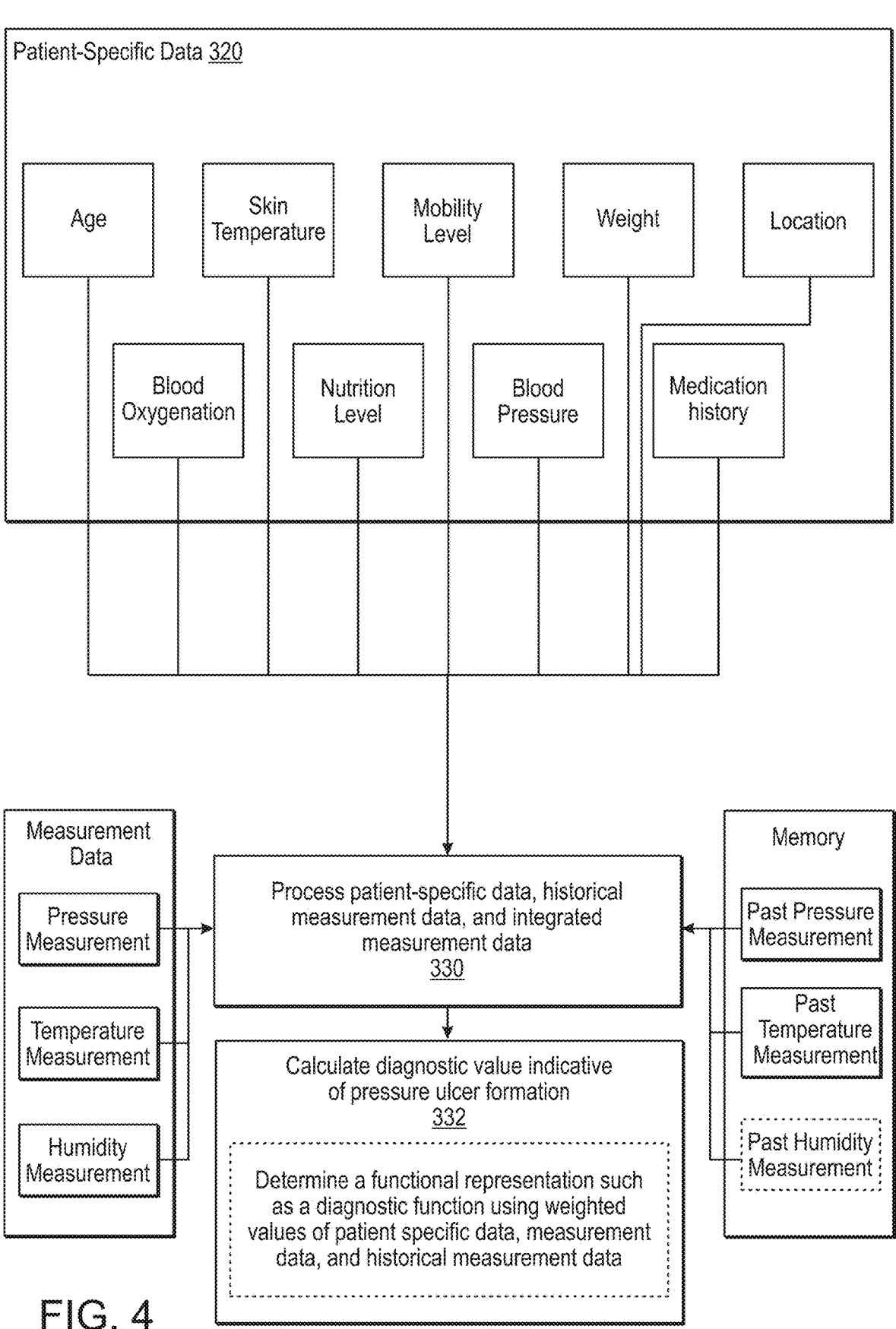
FIG. 4 illustrates a schematic of a method for calculating a value indicative of pressure ulcer formation in accordance with some embodiments of the present disclosure.

As shown in FIG. 4, the patient-specific data can be processed along with the integrated measurement data and the historical measurement data. In some embodiments, processing the patient-specific data can include binning the patient-specific data. For example, a patient's age or weight may be provided to the calculation step as a range. Different patient-specific data can impact the calculation of the value indicative of pressure ulcer formation in different ways. For example, high values of age and weight, a medical condition such as diabetes, and low mobility for a patient can indicate a greater likelihood of pressure ulcer formation, and the calculated pressure ulcer diagnostic value may accordingly be indicative of greater risk of pressure ulcer formation for this patient.

Systems and methods described herein can use the real-time physiological patient data stream measured by the sensor device as inputs to a Bayesian statistical data integration algorithm. In some embodiments, the patient data are combined with user-entered inputs, such as skin and tissue conditions, weight, blood pressure, or others that are patient-specific. In some embodiments, these data (e.g., blood pressure) can be automatically acquired by the system. The data integration algorithm can yield estimates of the probability that the patient or caregiver must take proactive actions to reduce or eliminate the external pressure applied on the body part where the sensor is located to avoid further tissue damage leading to a pressure ulcer. If the probability is higher than a pre-determined threshold, an alarm can be triggered indicating that there is a potential risk of developing a pressure ulcer.

Methods and systems taught herein can process the measurement data before inputting the data into the calculation of the pressure ulcer diagnostic value indicative of formation of a pressure ulcer. In some embodiments, the pressure measurements can be calibrated using the value of temperature measurements. For example, a pressure sensor that has a resistivity value associated with it may experience temperature-dependent changes in resistance. The temperature measurement can be used to calibrate the resistance value in these embodiments. In some embodiments, the pressure measurement data can be integrated over time to generate an accumulated pressure measurement. The area over which pressure is applied to a tissue can be indicative of the potential for formation of a pressure ulcer. For example, the body can have a greater capacity to repair a pressure insult applied to a small area than a similar insult applied to a large area. In that scenario, the large area would be at greater risk for formation of a pressure ulcer. In some embodiments, the pressure measurement data can be integrated over time and space (e.g., the size of the sensor) to create an accumulated force measurement.

Methods and systems taught herein can use historical measurement data to calculate the value indicative of pressure ulcer formation. For example, a site on a patient that has recently been under adverse pressure conditions without full recovery may be more disposed to developing a pressure ulcer. In some embodiments, pressure, temperature, or humidity measurements can be stored in a memory and can be provided as inputs to the calculation of the pressure ulcer diagnostic value indicative of pressure ulcer formation.

A large pressure applied to a tissue even for a short time can predispose the tissue to formation of pressure ulcers (i.e., the effect of pressure on tissue need not saturate at a specific value). Although a pressure of 35 mmHg can be sufficient to occlude blood flow in the capillaries of a tissue, higher pressures can create additional impacts that can increase the chances of forming a pressure ulcer. Systems and methods taught herein can measure the pressure applied to an area of tissue over time and weight the measurement appropriately during calculation of the pressure ulcer diagnostic value indicative of formation of a pressure ulcer.

In some embodiments, calculating the pressure ulcer diagnostic value indicative of pressure ulcer formation can include determining a functional representation such as a diagnostic function using weighted values of patient specific data, integrated measurement data, and historical measurement data. In some embodiments, the determined diagnostic function can incorporate historical measurement data directly into the representation rather than accessing historical data in a memory. For example, the historical data can be incorporated into the representation coupled with a decaying function that slowly de-weights the data's importance over time. An important purpose of the diagnostic function is to measure the time dependent effects of the pressure exerted at a particular tissue site. The diagnostic function preferably depends substantially on the accumulated pressure over time. The occurrence of repetitive injury at a particular body location where blood flow has been restricted periodically due to excessive pressure can substantially increase the risk of pressure ulcer formation. Different body locations, however, will respond differently for given levels of pressure over time. Thus, different locations on a particular patient will employ different diagnostic functions. Any given function can be iteratively processed at specified time intervals to determine whether a selected metric is converging to a particular value, for example. The metric can comprise an error metric, for example, in which a machine learning module iteratively computes a likelihood that a particular diagnosis is correct by minimizing an error function.

The pressure ulcer diagnostic function can be understood to comprise a function of a plurality of variables:

$$f(P_1, P_2, P_3, \ldots P_x, S_1, S_2, S_3 \ldots S_x)$$

Where $P_1, P_2, P_3, \ldots P_x$ comprise patient data as described generally herein and $S_1, S_2, S_3 \ldots S_x$ can comprise sensor data. As these features can vary with time for a given patient and can reflect actual values or reflect a target value or range in which a measured value should reside. The variables can each be defined in terms of a measured value at a point in time and a weighting coefficient for that variable, for example.

Figure 5A:
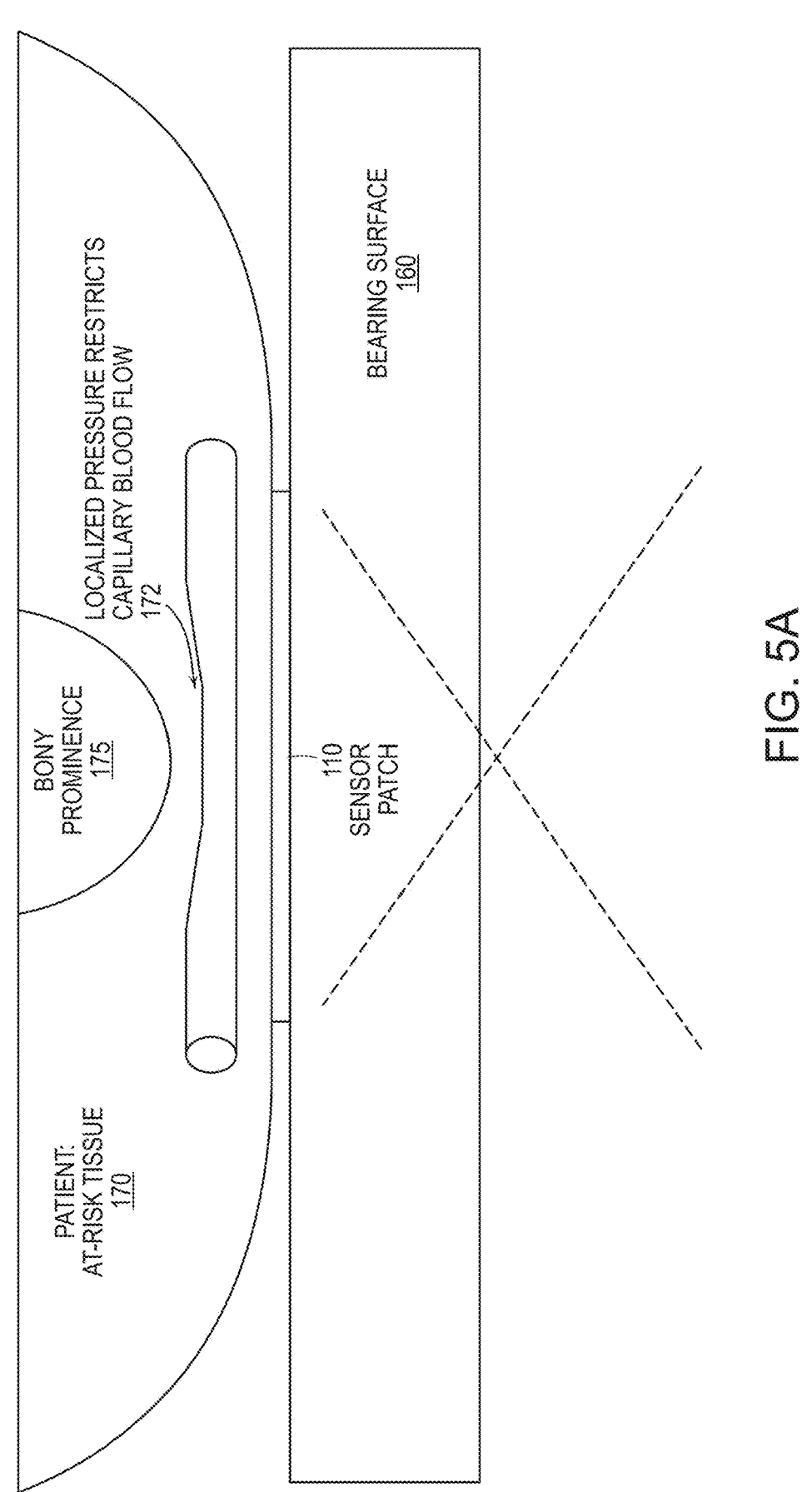
FIGS. 5A and 5B schematically illustrate a sensor device of some embodiments of the present disclosure affixed to a tissue of a patient.
Figure 5B:
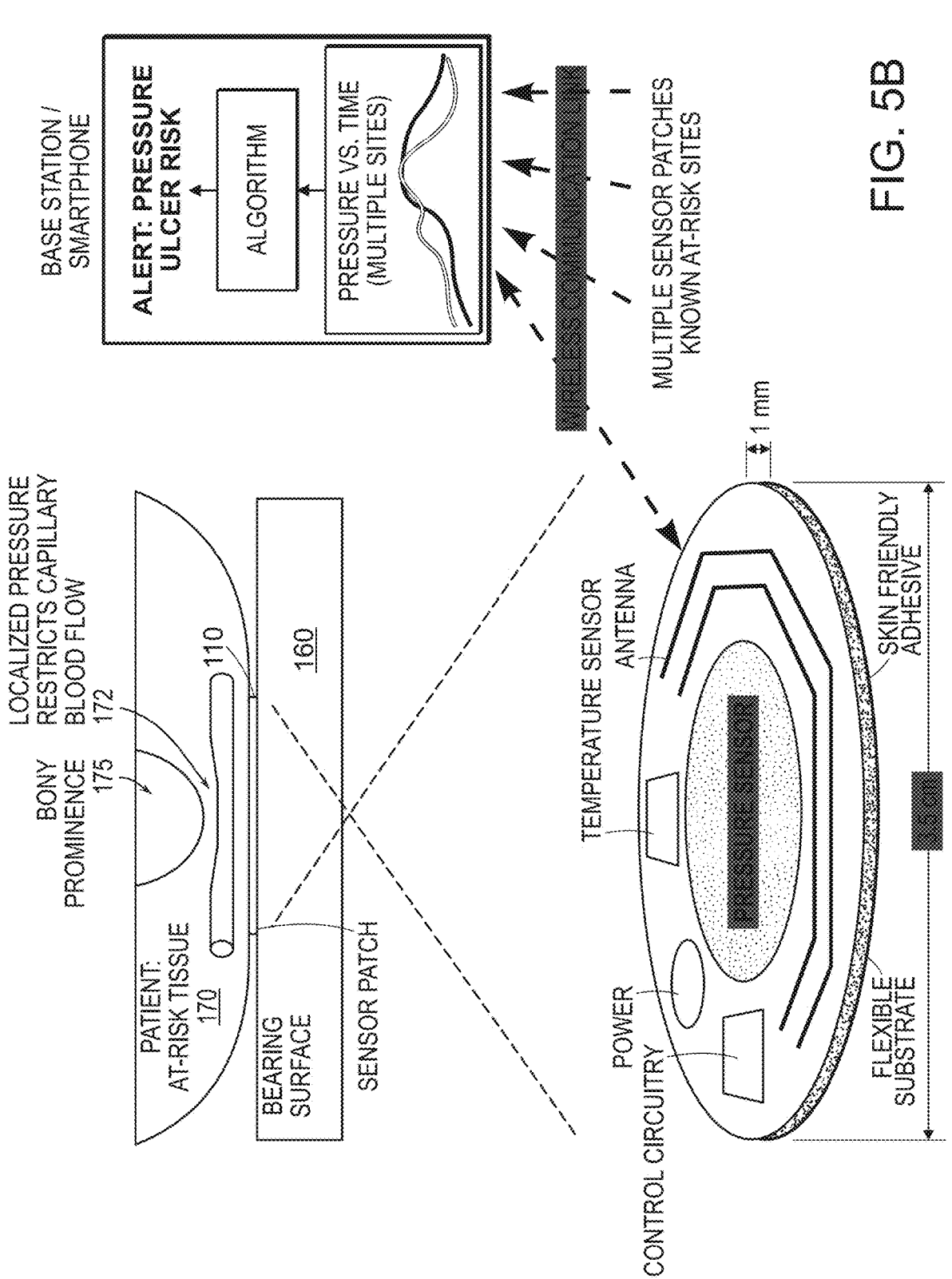

FIGS. 5A and 5B illustrate schematics of the sensor device 110 placed at an anatomical site of the patient in accordance with various embodiments of the present disclosure. The sensor device 110 can be placed on any tissue of the patient but is most preferably positioned on at-risk tissue 170 proximate to a bony prominence 175. In some embodiments, the sensor device 110 can be placed on or near the patient's ischium, sacrum, trochanter, heel, malleolus, knee, iliac crest, elbow, pretibial crest, pinous process, occiput, chin, scapula, or any other suitable location. When the anatomical site is placed into contact with a bearing surface 160, the tissue 170 located between the bony prominence 175 and the bearing surface 160 can be compressed. If the compression pressure is high enough, blood flow in the capillaries 172 can be occluded. This reduced blood flow (and concomitant reduction in blood oxygenation) can lead to tissue damage or necrosis that the body is unable to repair in a timely fashion. In some embodiments, the sensor device 110 can detect reductions in blood flow or other changes in the tissue 170 such as temperature, color, or oxygenation level.

Figure 6A:
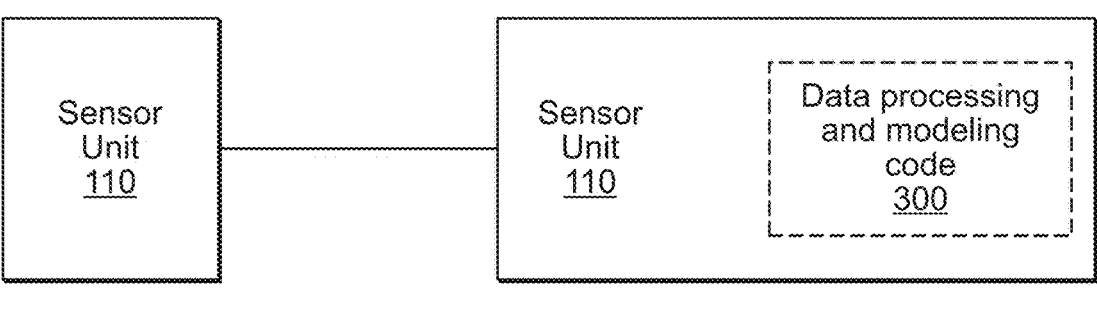
FIGS. 6A, 6B, and 6C illustrate schematic embodiments of systems for prevention of pressure ulcers in accordance with some embodiments of the present disclosure.
Figure 6B:
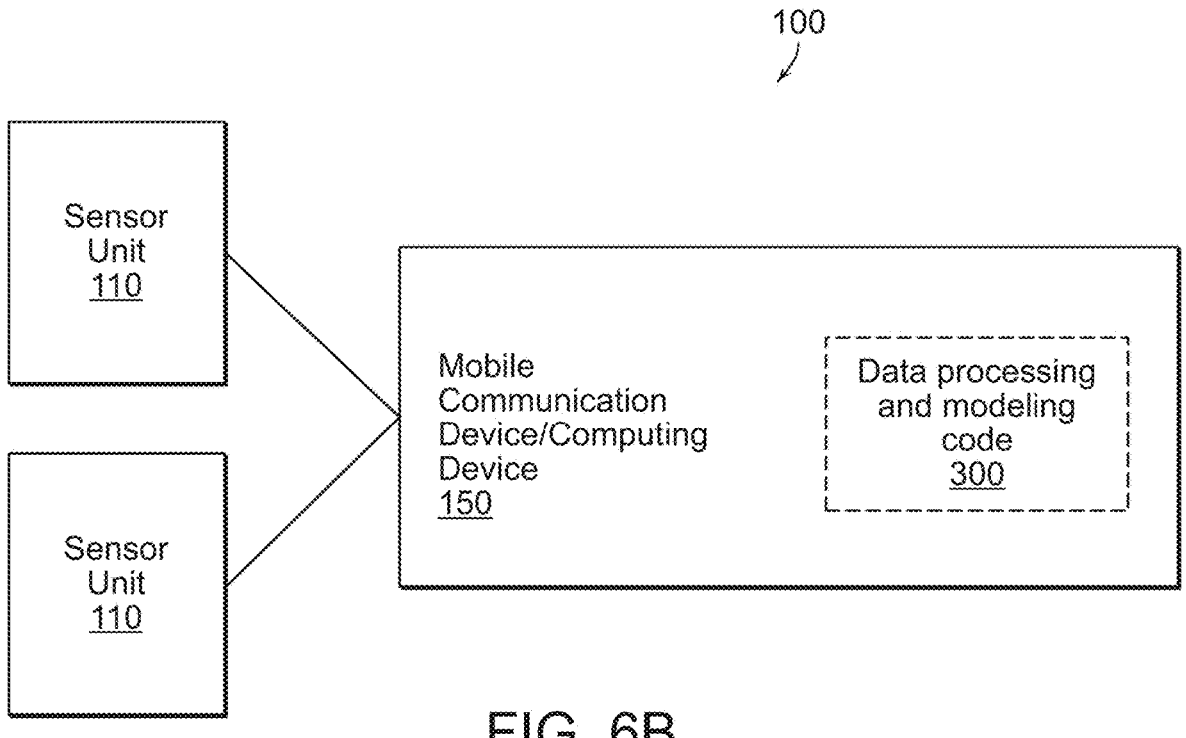
Figure 6C:
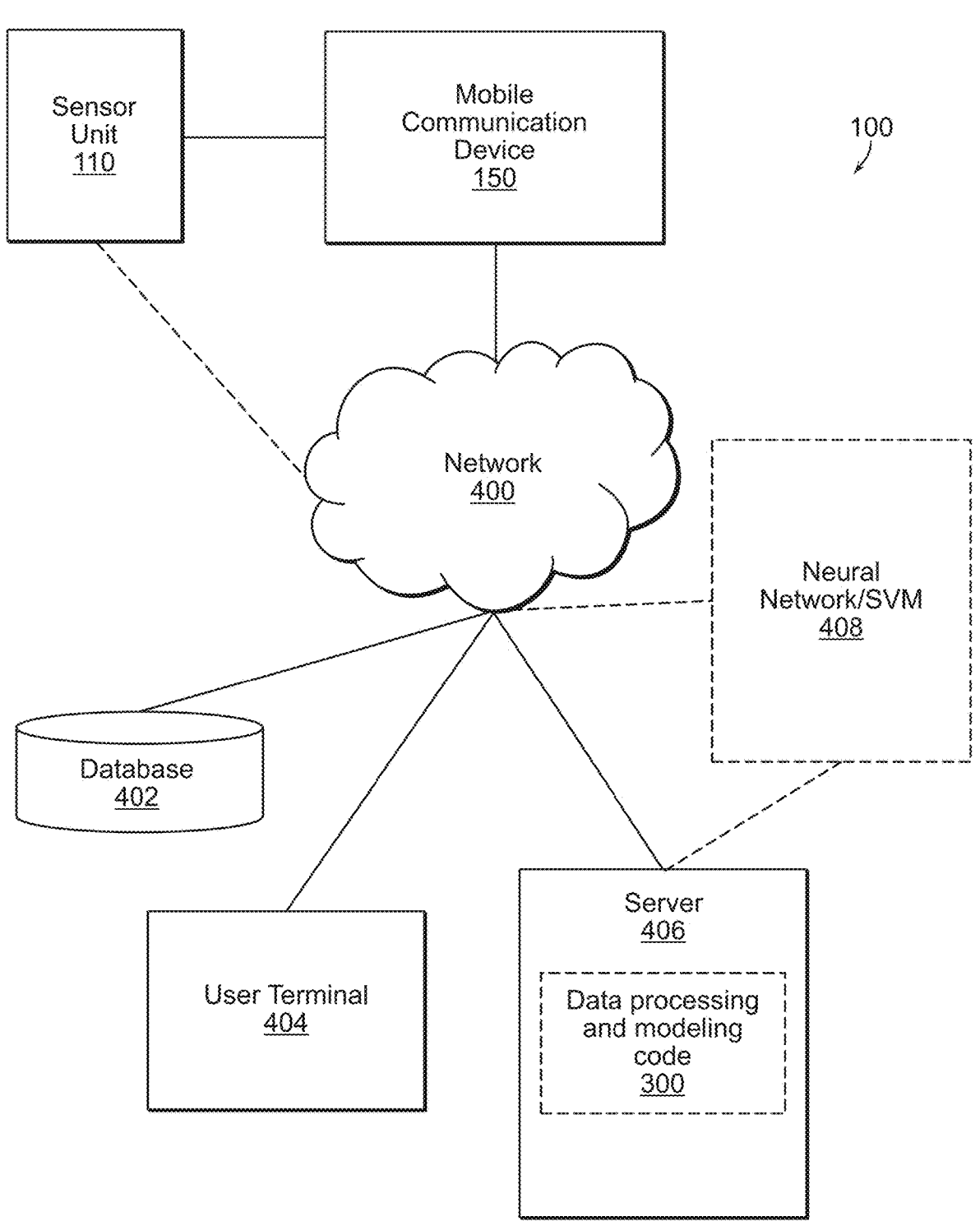

FIGS. 6A-6C illustrate schematic representations of systems for prevention or monitoring of pressure ulcers in accordance with various embodiments of the present disclosure. In FIG. 6A, the system 100 includes one or more sensor devices 110. The sensor devices 110 may be similar to those described above with reference to FIGS. 1-2B. In some embodiments with a plurality of sensor devices 110, the sensor devices 110 can each include a communications interface 118 to allow the sensor devices 110 to communicate with one another. The communications interface 118 can non-exclusively include the capability to communicate using a variety of standards such as 802.11x, BLUETOOTH®, near-field communications (NFC) or RFID device, or any other suitable communications standard. In some embodiments, at least one of the sensor devices 110 can include a data processing and modeling code 300 that can receive measurement data from sensors in the one or more sensor devices 110. The data processing and modeling code 300 can process the measurement data, patient-specific data, and historical measurement data to calculate the pressure ulcer diagnostic value indicative of the formation of a pressure ulcer.

FIG. 6B shows a system 100 for preventing formation of pressure ulcers including one or more sensor devices 110 and the base station 150. The base station 150 can include a mobile communications device or a computing device. The base station 150 can be located locally or remotely with respect to the one or more sensor devices 110. In some embodiments, the base station 150 can include data processing and modeling code 300. In some embodiments, the base station 150 can be a mobile communications device such as a smartphone. In such an embodiment, the smartphone can provide an alert to the patient or a provider that action is needed to prevent formation of a pressure ulcer (e.g., an alarm to awaken the patient if they are sleeping in one position for too long). The mobile devices can include an electronic display utilizing a graphic user interface (GUI). The GUI can have expandable menus from a toolbar to access patient data entry, diagnostic function profile as well as display real time and/or historical data.

FIG. 6C shows a system 100 for preventing pressure ulcers including one or more sensor devices 110, the base station 150, a network 400, a database 402, a user terminal 404, and a server 406. The system 100 can also optionally include a neural network or support vector machine (SVM) 408 that can be connected to the network 400 or directly to the server 406. In some embodiments, the server 406 or neural network 408 can include data processing and modeling code 300. In some embodiments, the neural network/ SVM 408 can include a learning capability that can use a dataset (such as found in database 402, for example) including measurement data, patient-specific data, and patient outcomes to train a model including a functional representation such as a diagnostic function using weighted values of the data. In some embodiments, the SVM 408 can identify correlations between patient-specific data, measurement data, and patient outcomes. Correlations identified by the SVM 408 can be used to revise and improve the weighted values in the diagnostic function or can be used to revise the diagnostic function itself. In some embodiments, the SVM 408 can communicate with the server 406 to revise the data processing and modeling code 300 with improved diagnostic functions which can be functional represented as a plurality of variable with weighting parameters.

Generally, an SVM module trains a classifier and computes a weight vector w.

$$w = \sum_{i=1}^{n} \alpha_i y_i x_i,$$

Where $x_i$ comprises the attribute set such as the system variables described herein and $y_i$ is a class label such as sensor data or patient data. The $\alpha_i$ can comprise Laguargian multipliers for weighting the vectors to optimize the system. The system defines ranking criterion $C_i$ defined as a quadratic function of the weight vector, namely $C_i=(w_i)^2$ for all i Next, the feature with the smallest ranking criterion is identified by determining argmin(c), and removing this feature from the ranking. With the ranking established, parameters are selected. Further details regarding implementation of an SVM module applied to pressure ulcer data can be found in Su et al., "Data Mining Techniques for Assisting the Diagnosis of Pressure Ulcer Development in Surgical Patients," J. Med. Syst. (2012 36:2387-2399), the entire contents of which is incorporated herein by reference. Such systems however, failed to utilize real time sensor data used in conjunction with machine learning output to generate a diagnostic function.

Figure 6D:
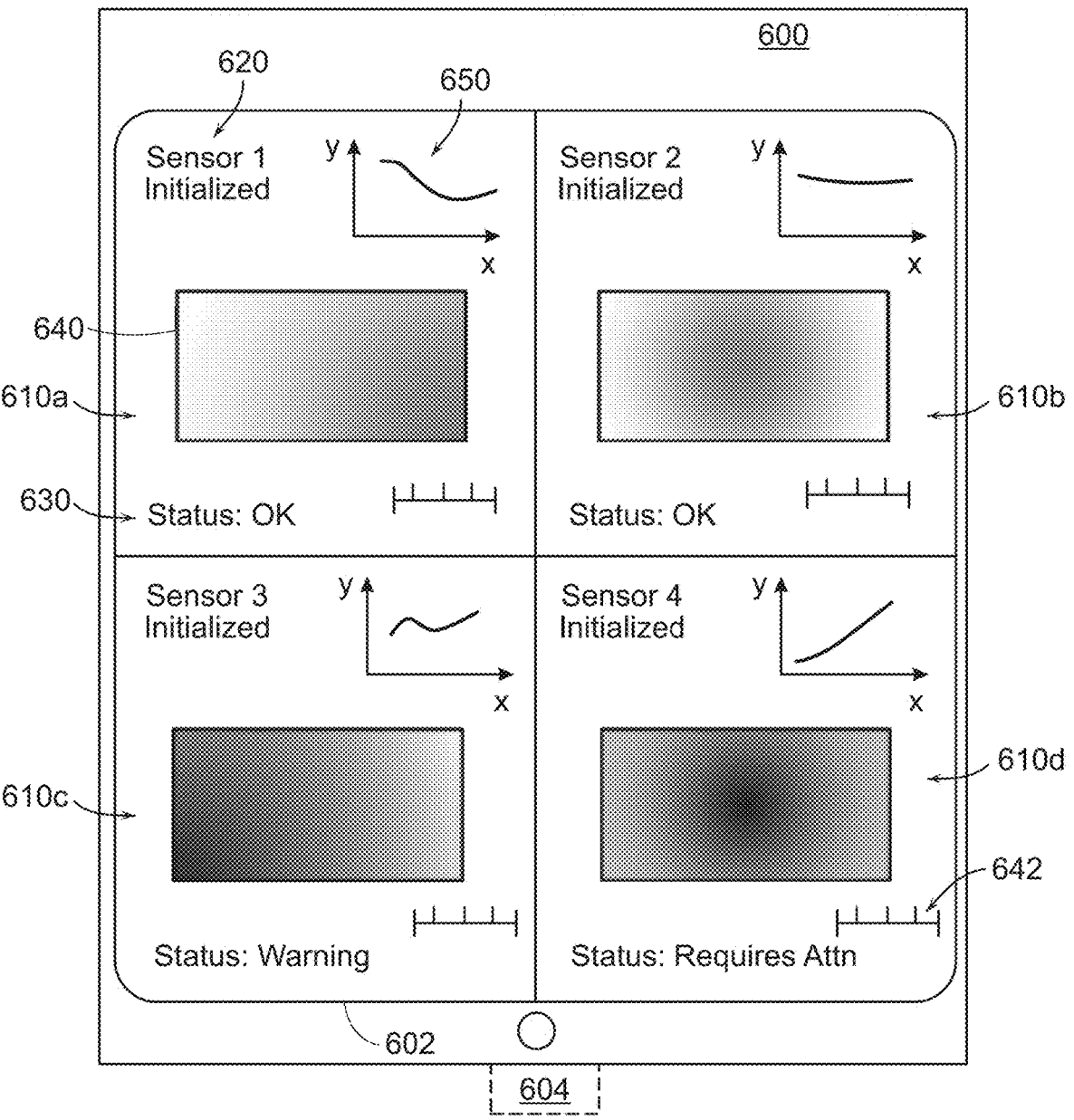
FIG. 6D illustrates an exemplary graphical user interface for a computing device connected to one or more sensor devices in accordance with some embodiments of the present disclosure.

FIG. 6D illustrates an exemplary graphical user interface (GUI) 602 for a computing device or mobile communications device such as a tablet 600 that is connected to one or more sensor devices 110 in accordance with embodiments of the present disclosure. In some embodiments, the GUI 602 can be divided into portions 610a-610d that correspond to different sensor devices 110. Each portion 610a-610d can include textual or graphical information. Although FIG. 6D illustrates a device having four portions 610a-610d, it will be apparent to one of ordinary skill in the art that the GUI

602 could be divided into a greater or lesser number of portions. In some implementations, the user can reduce the number of portions shown on the GUI 602 to focus on data from one or more specific sensor devices 110 or increase the number of portions shown on the GUI 602 to get a broad overview of the status system wide. In some implementations, the GUI 602 can dynamically change the number of portions 610a-610d that are displayed in response to initializing additional sensor devices 110 or losing communication or de-registering sensing devices 110.

The tablet 600 can include a scanner 604 to read a unique identifier associated with each sensor device. For example, the scanner 604 can be a proximity scanner or machine reader such as an RFID scanner that can interface with an RFID tag on the sensor device. In another embodiment, the scanner 604 can include an imaging device or barcode scanner to read the unique identifier that is visually displayed on the sensor device. The tablet 600 is programmed to activate the sensor device, identify the data format to be provided by each device, perform the data analysis required by each device, and display the resulting diagnostic data for each device. As a user activates a particular sensor device, the user identifies the body location for that device for a particular patient. The patient's electronic medical record can be accessed along with sensor activation so that data retrieved from sensors applied sequentially to the same location can be utilized in the continuing monitoring of the patient's condition. The tablet or mobile communication device touchscreen operates as a unitary interface for operation of the one or more sensors activated for the patient.

Each portion 610a-610d can provide a user with information related to the operation of the sensor device and/or information related to data received from the sensor device. For example, the portion 610a can include a label 620 identifying the sensor device that corresponds to that portion. The label 620 can be provided by the computing system 150 or can be user-defined. In some embodiments, the label 620 can include a descriptive phrase corresponding to the location of the sensor device 110 on the body such as "heel," "left buttock," or "right leg." In some embodiments, the label 620 can include unique identifying information for the sensor device 110 such as, for example, a serial number. The portion 610a-610d can include a status indicator 630. The status indicator 630 can provide a status of the portion of the body adjacent to the relevant sensor device 110 as adjudged by the risk model. For example, the status indicator 630 can identify the adjacent body portion as not needing medical attention, soon to be in need of attention if pressure continues, or currently in need of medical attention. In some embodiments, the status indicator 630 can include color such as red to indicate danger, yellow to indicate caution, and green to indicate that no problems are imminent.

Each portion 610a-610d can include a graphical pressure representation 640 of pressure sensed by the sensor device 110. In various embodiments, the graphical pressure representation 640 can illustrate instantaneous pressure values, current and historical pressure values, or a metric related to pressure value in combination with other measurement values. In some embodiments wherein the sensor device 110 includes an array of pressure-sensitive areas, the graphical pressure representation 640 can include a "pixelated" view showing the pressure values across the array of pressure-sensitive areas. For example, the graphical pressure representation 640 can include false-color or grayscale information correlated to the intensity of the pressure at a given point. The graphical pressure representation 640 can provide visual feedback to a user to illustrate which specific section of the body portion is receiving a particularly high or low level of pressure and to make adjustments to body position accordingly.

Each portion 610a-610d can include a plot 650 of pressure values. The y-axis of the plot can represent measured values of pressure, temperature, relative humidity, probability of pressure ulcer formation, or other relevant data in various embodiments. The x-axis of the plot can represent time in various embodiments. The user can select (e.g., by using a drop-down menu) the data to be displayed on each axis. The plot 650 can be updated continuously or at intervals (for example, every 5 seconds, 10 seconds, 30 seconds, 60 seconds, 120 seconds, or more). In some embodiments, the plot 650 can provide a quick assessment of the pressure history trend at the location of the sensor device 110.

The GUI 602 can include a pressure threshold setting 642 that can be adjusted by a user, for example, by touching or dragging the indicator. Depending upon the location of the associated sensing unit, the threshold pressure at which the system should trigger an alert for imminent formation of pressure ulcers can change. In various embodiments, the tablet 600 can automatically calculate a range of pressure thresholds appropriate to the location of the sensor unit 110 on the body of the patient. The tablet user can use the pressure threshold setting 642 to apply gross or fine adjustments to the pressure threshold. The decision to adjust the pressure threshold setting 642 can be based upon factors such as knowledge of ulcer formation on the analogous body part (e.g., knowledge that the patient's other heel has formed an ulcer) or either heightened circumstances.

Figure 6E:
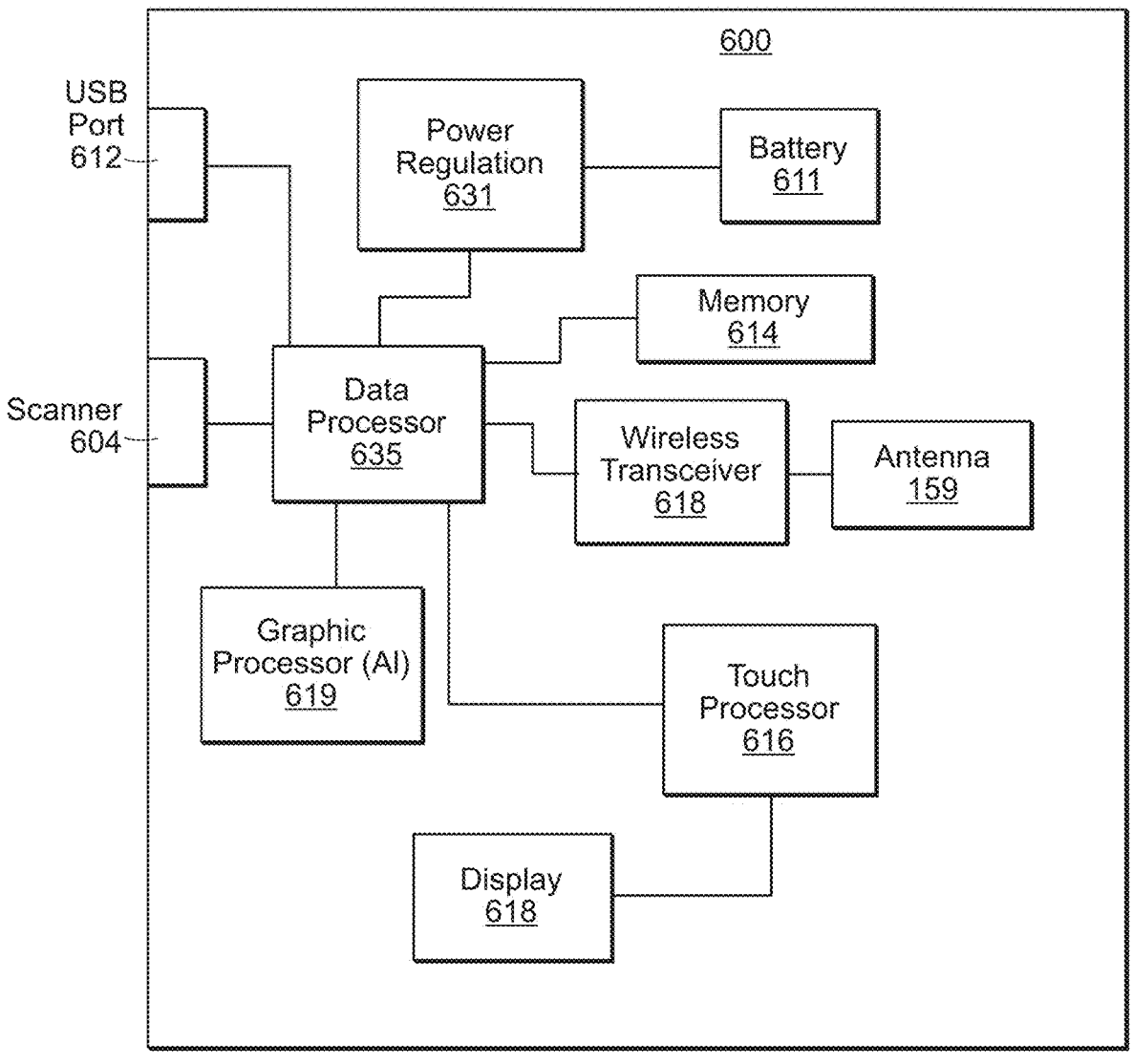
FIG. 6E illustrates a schematic representation of a computing device for use with systems and methods described herein in accordance with various embodiments.

FIG. 6E illustrates an schematic representation of a tablet 600 or computing device for use with various embodiments described herein. The tablet 600 can include any of a scanner 604, a battery 611, power regulation circuitry 631, a memory 614, a wireless transceiver 618, an antenna 159, a second data processor 635, a touch processor 616, a touchscreen display 618, a graphics processor 619, and a USB port 612. In such embodiments, a housing of the data processor 635 and other components can be a portable device such as a tablet 600.

The pressure sensor 112 can include a force sensing resistor (FSR) in some embodiments. FSRs can include semiconductor polymer composites (e.g., supplied as a polymer sheet or ink that can be supplied by screen printing). A matrix in the FSR can be selected from nonconductive polymers, while a filler can be selected from conductive materials. Under a compressive force, the electrical resistivity changes due to the change of particle separation distance in the matrix. Theoretically, the force-resistance characteristic is relatively linear in the log-log scale. However, some FSRs can exhibit a time dependent behavior and nonlinearity issues caused by the fact that interparticle separation reduces as the polymer matrix in the semiconductor polymer composites creeps under a fixed stress. This nonlinearity problem of the FSR can become a concern in the pressure ulcer prevention measurements where accuracy and reliability are significant factors. Earlier works proposed an algorithm that implements derivative criteria to distinguish between the increase of applied load and the creep behavior under a fixed load. However, in the continuous pressure monitoring environment, if the increase of pressure shares the same characteristic with the creep behavior, this algorithm will not work. Other works have developed mathematical models to predict the resistance and its time dependence by considering the cause of the change in resistance within composites, constriction resistance, tunneling resistance, and contact resistance between the electrodes and the polymer composite. These models have the disadvantage that they require knowledge of material parameters, such as volume fraction, filler particle diameter, potential barrier height, and others.

As described above, the pressure sensor 112 of some embodiments can be a polymer thick-film sensor. One challenge associated with use of a polymer thick-film pressure sensor can be part-to-part variability of up to ±25%. In some embodiments, the interface electronics can employ a voltage-based resistance measurement technique. The pressure sensor can be placed in a voltage divider configuration with a reference resistance. With a known reference voltage applied, the voltage divider output can be digitized by an analog-to-digital converter (ADC). The resistance value of the pressure sensor can be inferred from the measured voltage using the voltage divider relationship. With the resistance value of the pressure sensor, Equation 1 can be used to determine force, and pressure can be determined using the sensor active area.

$$R_{SENSOR} = R_0 F^x \tag{1}$$

In some embodiments, a time-based resistance measurement technique can be used with the pressure sensor as described below with respect to FIG. 13. Systems and methods taught herein can provide a calibration procedure to enable linear force measurement with accuracy approaching single-part repeatability of ±2%.

Figure 7:
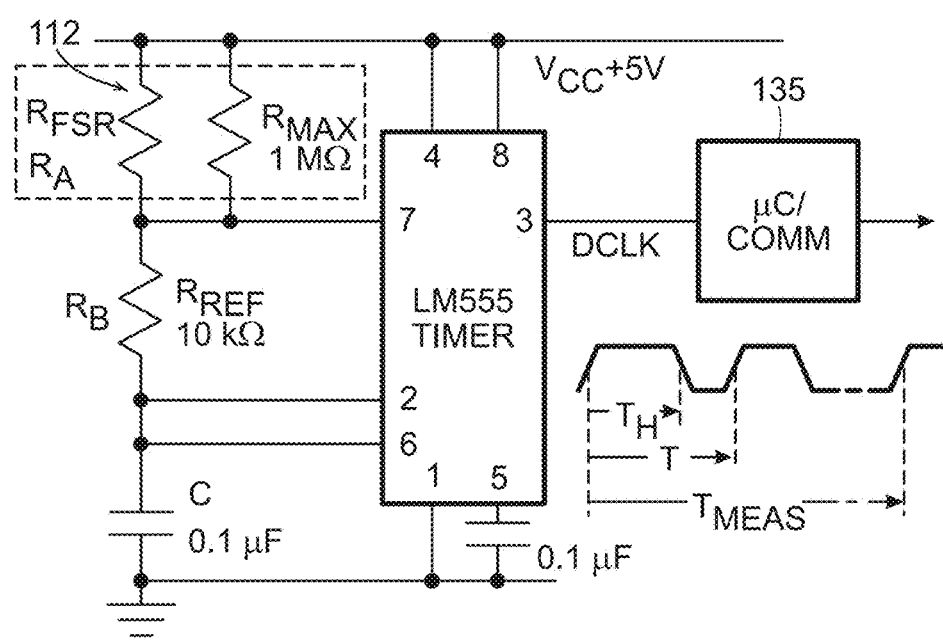
FIG. 7 illustrates a circuit diagram including a pressure sensor for use with some embodiments of the present disclosure.

FIG. 7 illustrates an exemplary circuit for obtaining a time-based resistance measurement from the pressure sensor 112 in accordance with various embodiments of the present disclosure. For the output digital waveform DCLK, the frequency f and duty cycle $\delta = T_H/T$ (fractional "high" time $T_H$ relative to the waveform period T) are given by $$f = \frac{1.44}{(R_A + 2R_B)C} \qquad \delta = \left(\frac{R_A + R_B}{R_A + 2R_B}\right) \tag{2}$$

Either expression in (2) can be used to determine resistance from a time domain measurement. In some embodiments, duty cycle can be used because it is independent of the capacitor value C. The duty cycle can be calculated by the microcontroller 135, which measures $T_H$ and Tin the digital domain over interval $T_{MEAS}$, covering many T periods. The microcontroller can also implement the calibration algorithm described below in some embodiments. The resolution of the measurement can be improved in some embodiments by increasing the $T_{MEAS}$ time measurement interval.

In FIG. 7, the pressure sensor 112 is shown as force sensing resistor $R_{FSR}$ placed in parallel with resistor $R_{MAX}$, giving $$R_A = R_{FSR} \parallel R_{MAX} = \frac{R_{FSR}R_{MAX}}{R_{FSR} + R_{MAX}} \tag{3}$$

This limits the maximum value of $R_A$, as $R_{FSR} \to \infty$ for zero force, which would result in a waveform period T exceeding $T_{MEAS}$. A known reference resistance $R_{REF}$ is used for $R_B$.

Combining (1), (2), and (3) and solving for force F gives $$F = \left[R_0\left(\frac{1}{R_{REF}}\left[\frac{1-\delta}{2\delta-1}\right] - \frac{1}{R_{MAX}}\right)\right]^{-1/x} \tag{4}$$

in which $R_{REF}$ and $R_{MAX}$ are known, and best-fit parameters $R_0$ and x can be determined from initial measurements.

Figure 8A:
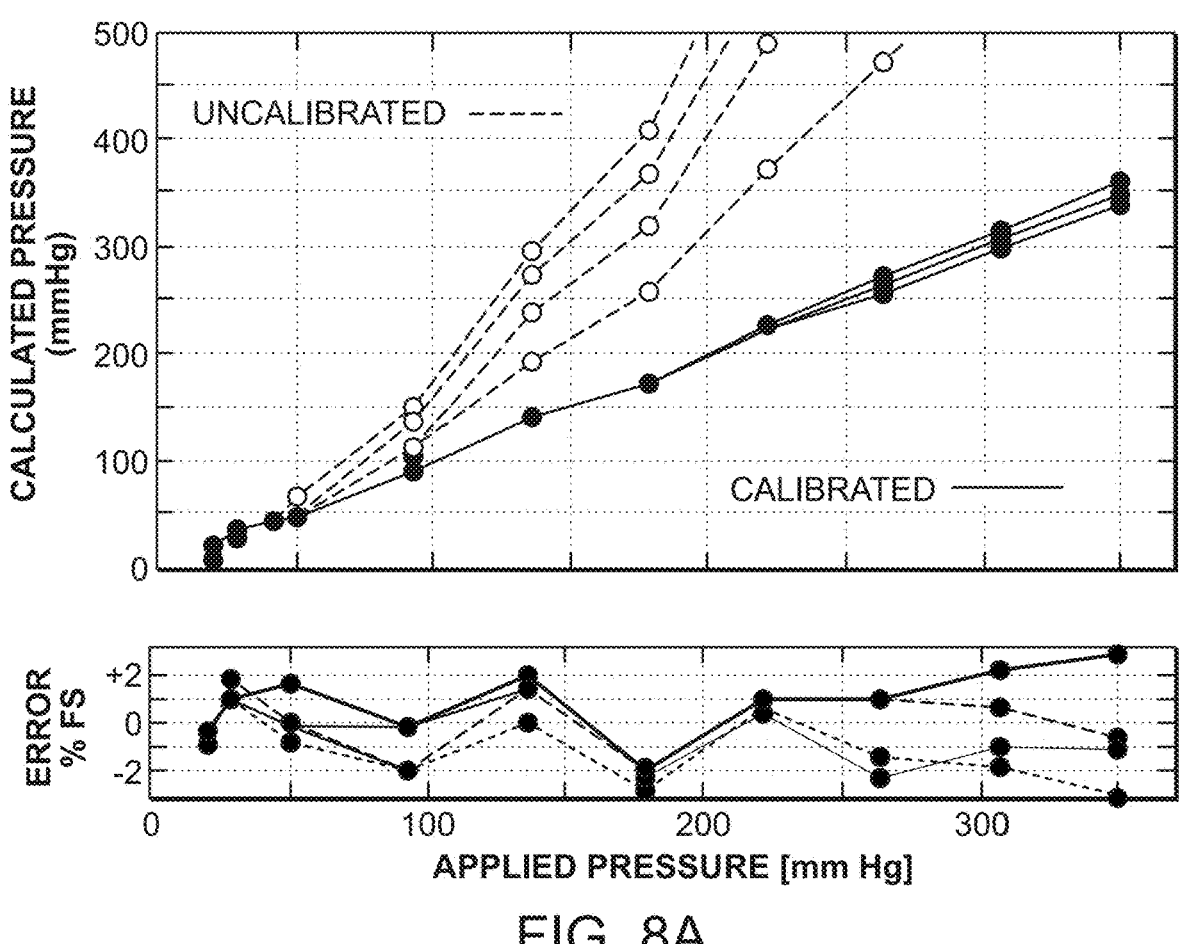
FIG. 8A illustrates a plot of calibrated and uncalibrated pressure measurements obtained using a pressure sensor in accordance with some embodiments of the present disclosure.

The embodiment of FIG. 7 was analyzed for accuracy over forces corresponding to a pressure range of 20 to 350 mm Hg. To assess tolerance of this approach to variation in the FSR characteristic, four different sensors were used for measurements. System parameters and results are summarized in Table I. The upper plot in FIG. 8A shows calculated pressure from (4) as a function of the known applied pressure. Each of the four sensors is represented in a different color. The dashed lines indicate calculated pressure using the nominal FSR parameters of (1); the wide sensor-to-sensor variability of parameters is apparent. The solid lines show results after calibration, using a least-squares determination of best-fit values for $R_0$ and x from (1) for each sensor. The lower plot in FIG. 8A shows the measurement error (the difference between the calculated pressure and actual applied pressure) as a fraction of the 350 mm Hg full scale. Despite the wide variation in initial uncalibrated performance, the model of (1) enables accuracy within ±3% for calibrated output.

In accordance with various embodiments, the calibration curve can be corrected for variation due to temperature. In some embodiments, the system can correct the slope or offset of the calibration curve itself as a function of temperature measured, for example, using a temperature sensor 114 as described above. In some embodiments, the system can apply a correction to the data based upon the measured temperature. For example, the system can apply an absolute or percentage shift in the obtained pressure values for each degree of temperature change with respect to the temperature at which the calibration occurred.

Figure 8B:
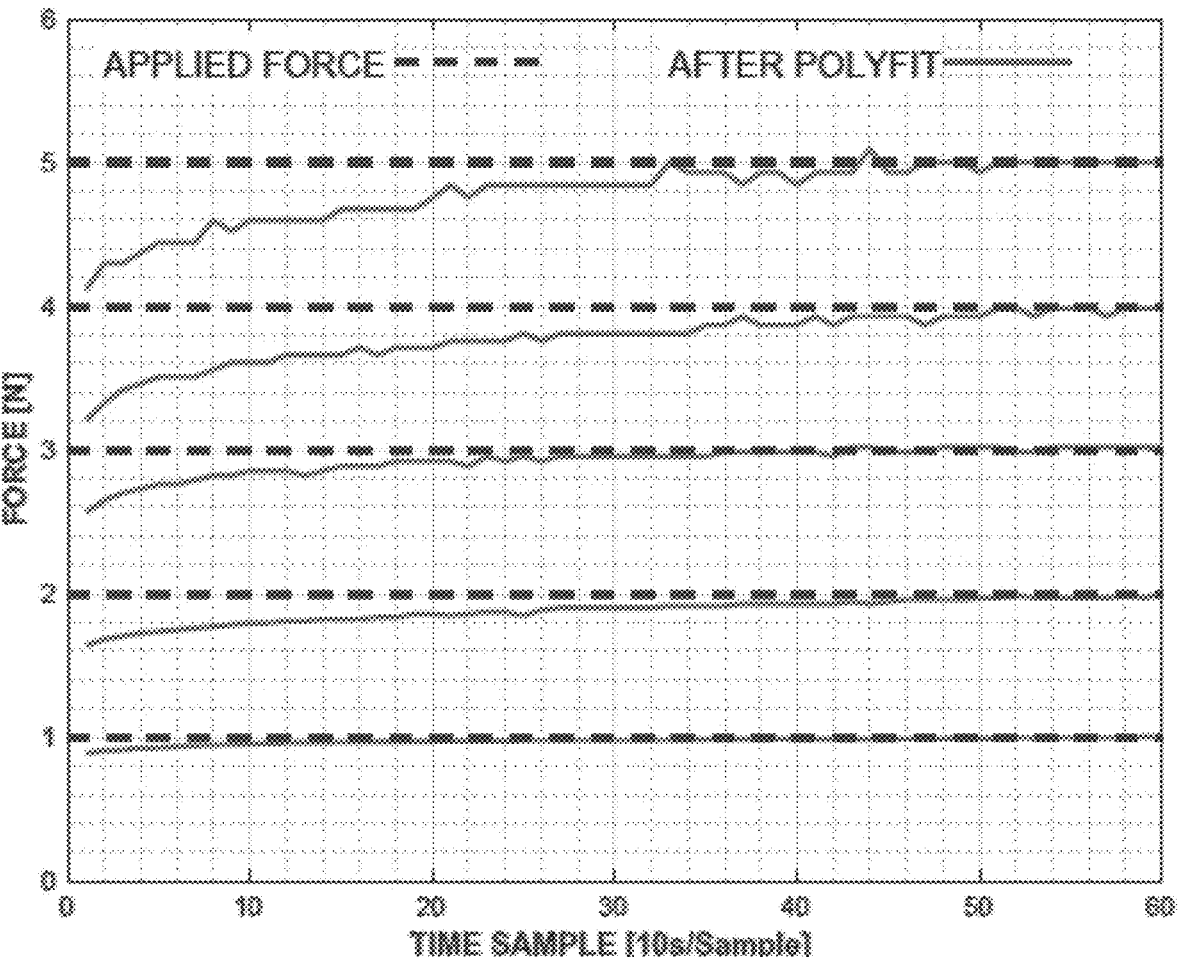
FIG. 8B shows measured force over time for individual pressure sensors to illustrate the phenomenon of settling.
Figure 8C:
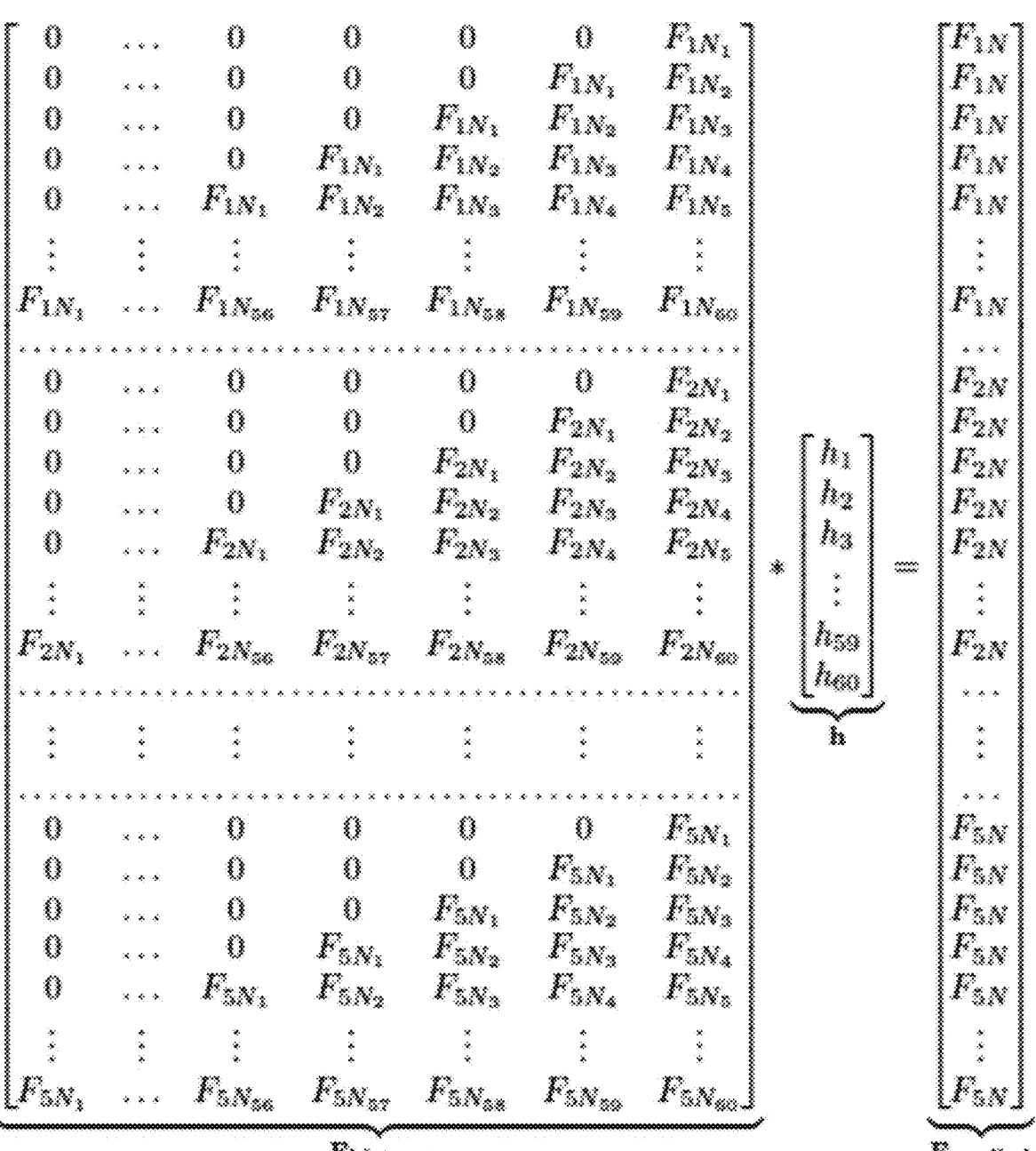
FIG. 8C illustrates the formulation and use of the past history data matrix in a convolutional method for sensor calibration in accordance with some embodiments described herein.

The polynomial curve fitting method described above can provide acceptable error levels in some embodiments. However, the polynomial curve fitting method works best when the sensor device 110 has already settled as shown in FIG. 8B. Thus, the polynomial curve fitting method described above can be improved further in some embodiments using a mathematical method of deconvolution to predict the force by taking the measured force history into consideration. For example, a past history data matrix $F_{history}$ can be constructed as shown in FIG. 8C. Upon calculation of the force as described above, each new sample of force data over time is added to the past history data matrix. Each new row of the matrix has one more sample than the previous row until all columns have been filled in. Every element before the first sample data is zero which indicates that no load is applied. Then, the past history data matrix can be multiplied by a vector h in order to deconvolve to the target applied force vector $F_{applied}$. The vector h is calculated by taking the pseudo-inverse of the past history data matrix $F_{history}$ and multiplying it by $F_{applied}$. By using the calculated value of vector h, the model prediction results for every force value can be computed.

Figure 8D:
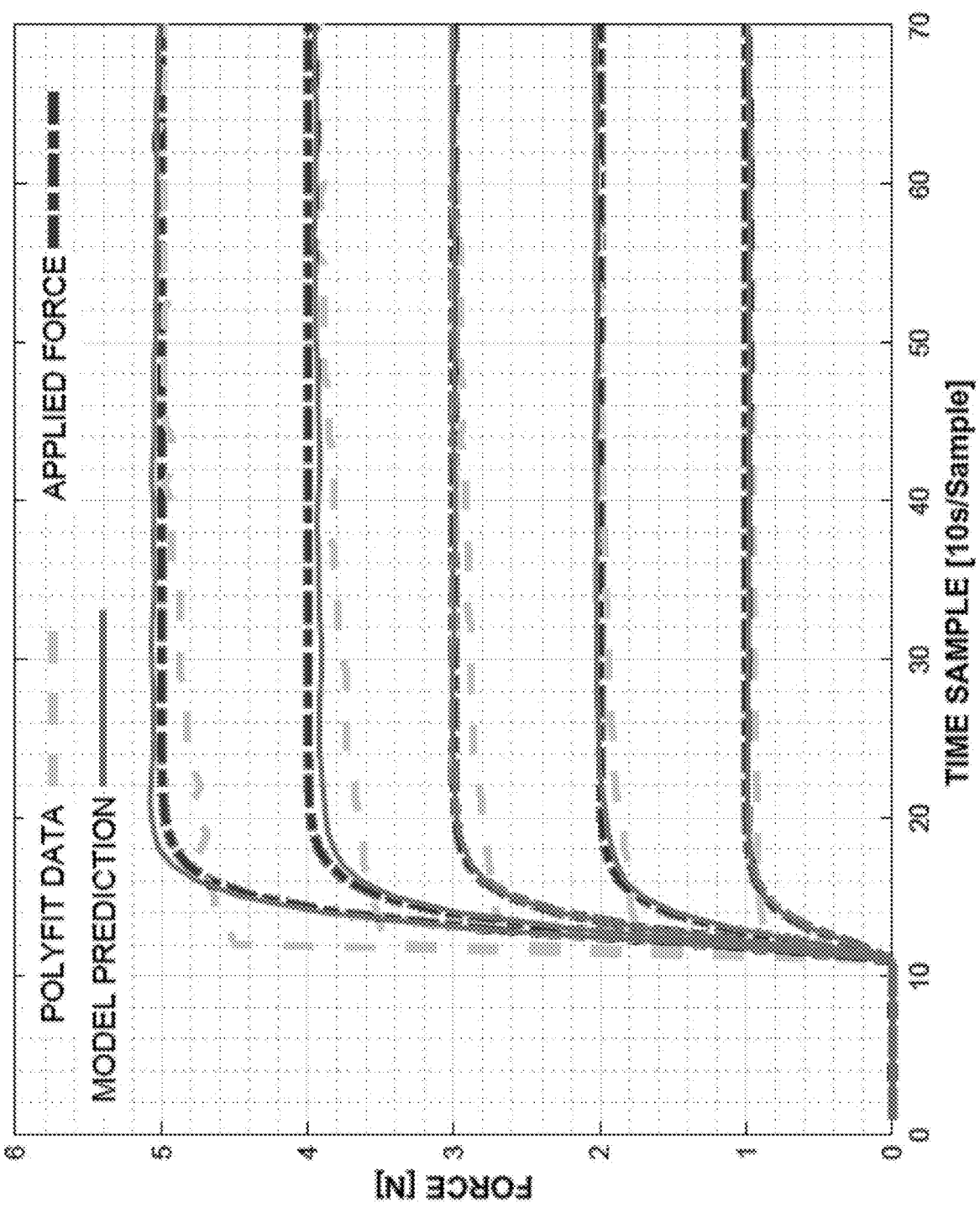
FIG. 8D illustrates the results of a test of the polynomial curve-fit and convolutional approaches.

FIG. 8D illustrates the results of a test of the polynomial curve-fit and convolutional approaches. The system was tested for two different force-sensing resistors to better understand part-to-part variability. Five different fixed loads were applied (1N, 2N, 3N, 4N, and 5N). As seen in FIG. 8D, the dashed-dotted line shows the second order step response for the applied force in each case. The dashed line shows the calculated force data after polynomial curve fitting methods. We can see that the accuracy of this method is dependent on the settling time of the sensor. The imperfections of the polynomial curve fitting method are rectified by the deconvolution algorithm, which predicts the force by knowing the history path. When the experimental data is still catching up to the applied force, the deconvolution algorithm already predicted the force in advance. The solid line shows the calculated force after the deconvolution algorithm. The prediction closely matches the applied force.

Figure 8E:
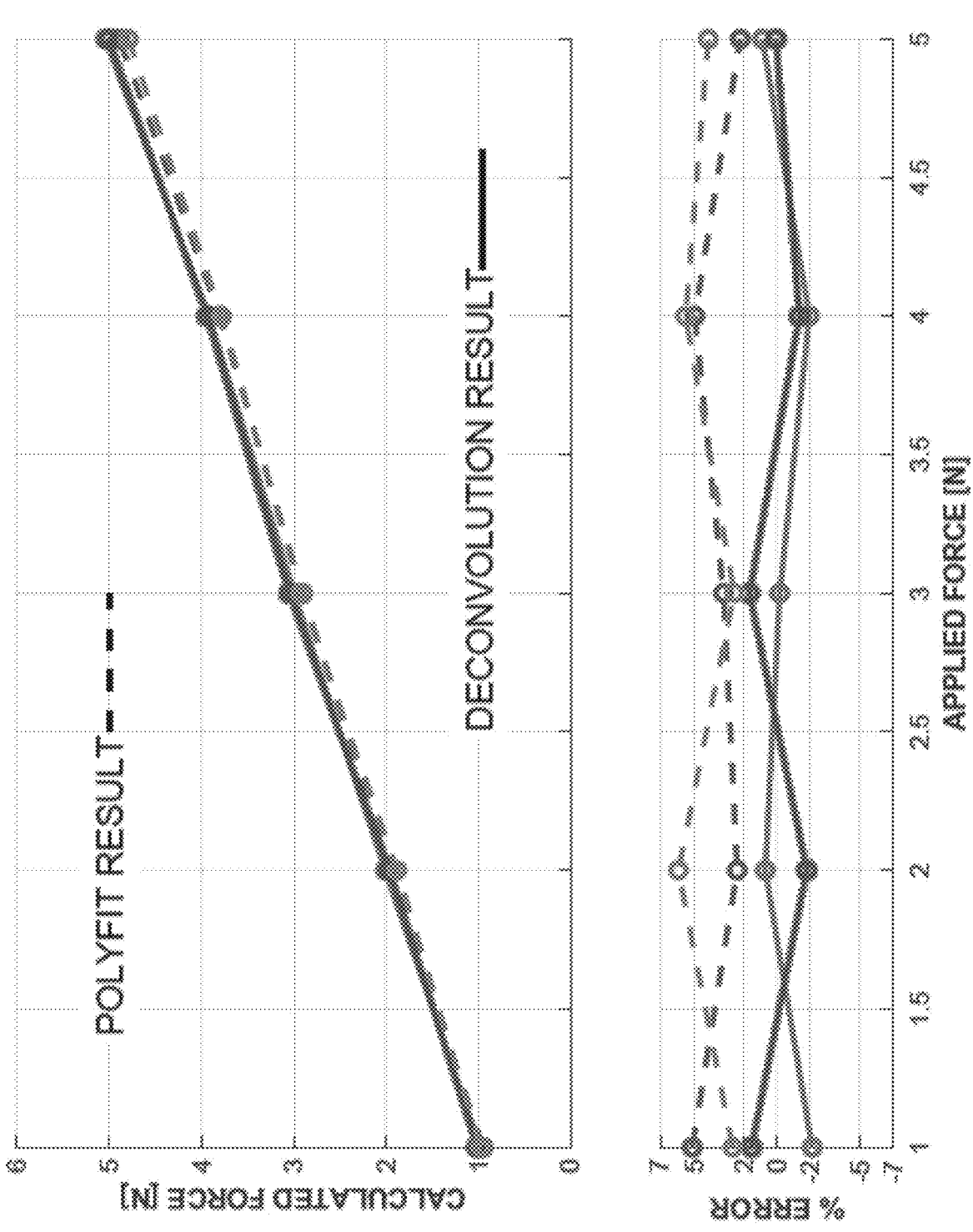
FIG. 8E shows the correction results after polynomial fit and the deconvolution prediction model results for the corrected force data.

FIG. 8E shows the correction results after polynomial fit and the deconvolution prediction model results for the corrected force data. Each point is calculated by taking the average of all 60 time samples for every given applied force. Two FSRs are evaluated to verify the reliability of the model. We can see that after polynomial curve fitting, the error is as high as 6%. Application of the deconvolution algorithm to the measured force can bring down the error to ±2%. In addition, the method of deconvolution calibration does not depend on settling time and does not require knowledge of particular material parameters or characteristics for the sensor.

Figure 9:
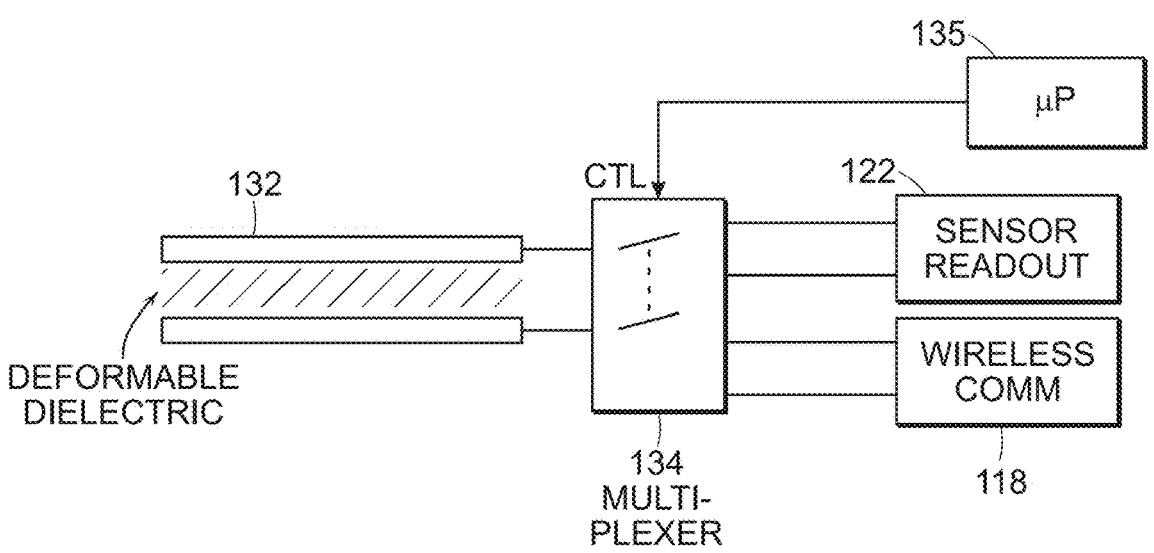
FIG. 9 illustrates a portion of a system including a pressure sensor that can also act as an antenna in accordance with some embodiments of the present disclosure.

As shown in FIG. 9, the pressure sensor of certain embodiments of a sensor device 110 according to the present disclosure can be a capacitive sensor 132. In some embodiments, the capacitive sensor 132 can be used as an antenna to transmit and receive information. In these embodiments, the sensor device 110 can also include a multiplexing unit 134 that can switch the function of the capacitive sensor 132 from antenna-like (i.e., transmitting and receiving information) to sensor-like (i.e., measuring capacitance to determine pressure values). The multiplexing unit 134 can be under the control of a microprocessor 135. In some embodiments, the signal transmitted or received at the capacitive sensor 132 can be demodulated by the pressure sensor readout 122 or the multiplexing unit 134 to provide information indicative of the pressure on the capacitive sensor 132. The communications interface 118 can include a portion that senses the quality of impedence matching to the capacitive sensor 132 acting as an antenna. The quality of impedence matching can be correlated to the pressure applied to the capacitive sensor.

Figure 10:
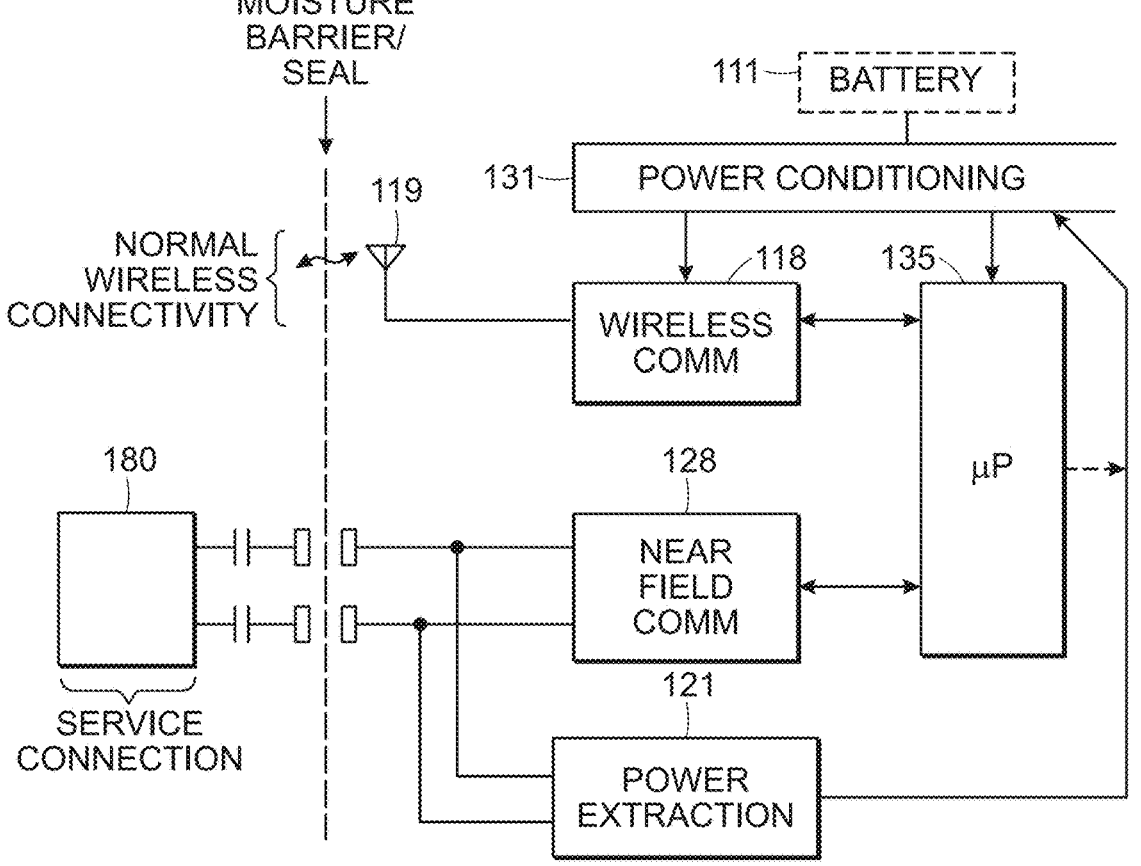
FIG. 10 illustrates a portion of a system including components to enable a service connection in accordance with some embodiments of the present disclosure.

FIG. 10 illustrates a schematic of a portion of a sensor device including components to enable a service connection in accordance with some embodiments of the present application. In some embodiments, the use of a service connection or secondary communication method can enable communication with the sensor device even if the primary connection method is disabled. The sensor device can include a near field communications (NFC) component 128 that can be activated using an external service connection device 180 across the moisture barrier or seal. In some embodiments, the near field communications component can be an RFID or other sensor that is latent until powered by the external device. In some embodiments, the microcontroller 135 can receive or transmit data through the near field communications module 128 to the service connection 180. The sensor device can also include a power extraction module 121 that can extract power from the service connection 180 and deliver the power to a power conditioning unit 131 that may be connected to a power source 111 such as a battery.

Figure 11:
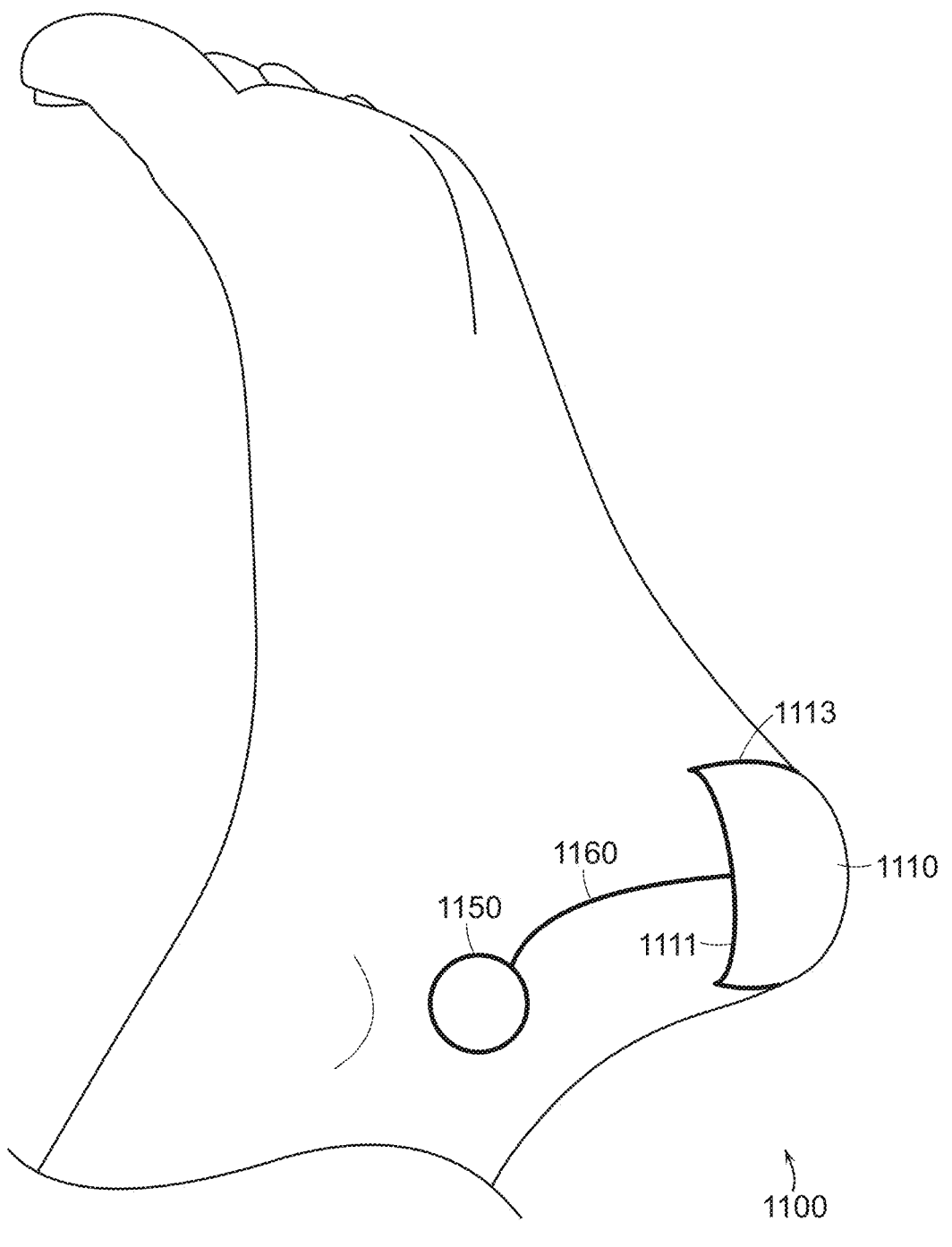
FIG. 11 illustrates a system for prevention of pressure ulcers in accordance with some embodiments of the present disclosure positioned on a heel of a patient.

Because the systems and methods described herein are often located at the position where a pressure ulcer is likely to occur (for example, at a bony prominence), the sensor device must be able to withstand large pressures over a period of time. However, the systems applied to these locations must be comfortable enough for long-term wear on a user's body to promote compliance in wearing the device. FIG. 11 illustrates an embodiment of a pressure ulcer monitoring system 1100 applied to a heel of a user. The pressure ulcer monitoring system 1100 can include a sensor device 1110, an electronics unit 1150, and a communication link 1160 (such as a cable or flexible band in some embodiments) between the sensor device 1110 and electronics unit 1150. In some embodiments, the sensor device 1110 can include sensors while the electronics unit 1150 can include the associated integrated circuit elements for the system 1100. By spatially separating the sensor device 1110 from the accompanying electronics unit 1150, the integrated circuit elements in the electronics unit 1150 are located outside the high-pressure zone (thus reducing the likelihood of damage) where the user is less likely to feel them during normal activities.

Similar to the sensor device 110 described above with relation to FIG. 1, the sensor device 1110 can include the pressure sensor 112, the temperature sensor 114, the moisture sensor 116, or the light sensor 113. In accordance with various embodiments, the sensor device 1110 can conform to the portion of the body to which it is affixed. To accommodate portions of the body that are highly curved such as, for example, the heel or elbow, the sensor device 1110 can flex or bend in one or two directions to conform to the curved body portion. In some embodiments, the sensor device 1110 can have a first maximum bend radius 1111 (i e, minimum radius of curvature) with respect to a first dimension of the device and a second maximum bend radius 1113 (i.e., minimum radius of curvature) with respect to a second dimension of the device. When the sensor device 1110 is bent by less than the first bend radius along the first direction and less than the second bend radius along the second direction, the sensors included within the sensor device 1110 will still function properly. In certain embodiments, the sensor device is manufactured to have a surface area that is configured with a selected radius of curvature in one, two or more directions so that it confirms to a specific surface area of the skin of a patient. This is particularly advantageous in embodiments having a sensor array on an individual patch as each sensor element in the array then has uniform contact pressure to the skin surface. The radius of curvature can vary within a specific quantitative range for a particular body location. The heel, for example, has a first preferred range, the shoulder has a second range for the radius of curvature, a third body portion as described herein can have a third range of the radius of curvature, etc., where the sensor device is flexible within the indicated range for a given body portion, with each range being different. The system software can detect matrix sensor elements that generate data that indicate poor pressure contact with the skin surface and can remove data from those elements from the analysis. The system can verify that a threshold of operative sensor elements in the array is sufficient to provide accurate diagnostic analysis. The system can prompt the user to reapply the sensor device if the threshold is not reached within the entire array or a subset of elements in areas of the array.

In some embodiments, the electronics unit 1150 can include the power source 110, the interface electronics 117, the digital processing 115, the wireless communication interface 118, or the antenna 119. In various embodiments, the electronics unit 1150 can be affixed on the user's body a short distance from the sensor device 1110. In some embodiments, the electronics unit 1150 can be located less than 5 cm, 10 cm, or 15 cm from the sensor device 1110. Some components in the electronics unit 1150 such as integrated circuits can have a thickness or shape that makes them prominent in the form factor of the unit even in the presence of surrounding cushioning. As such, pressure tends to focus on these elements and cause pre-mature breakage. Moreover, the user tends to find these "high points" in the electronics unit 1150 to be painful points. To mitigate these issues, the electronics unit 1150 can be located in an unobtrusive location on the body that experiences pressure only infrequently. For example, the electronics unit 1150 can be located in the depression in the hindfoot midway between the heel and the inner ankle.

The communication link 1160 can be wired or wireless in various embodiments of the present disclosure. For example, the communication link 1160 can utilize wireless communications methods such as near-field communications, BlueTooth™, or variants of 802.11 (wi-fi) to communicate. In some embodiments, the communication link 1160 can be facilitated through a network as described above with reference to FIGS. 6B and 6C. The communications link 1160 can be a physical, wired connection in some embodiments. In some embodiments, a wire connecting the electronics unit 1150 and the sensor device 1110 can be insulated or otherwise treated to protect against moisture or friction that arise due to movement of the user.

Figure 12A:
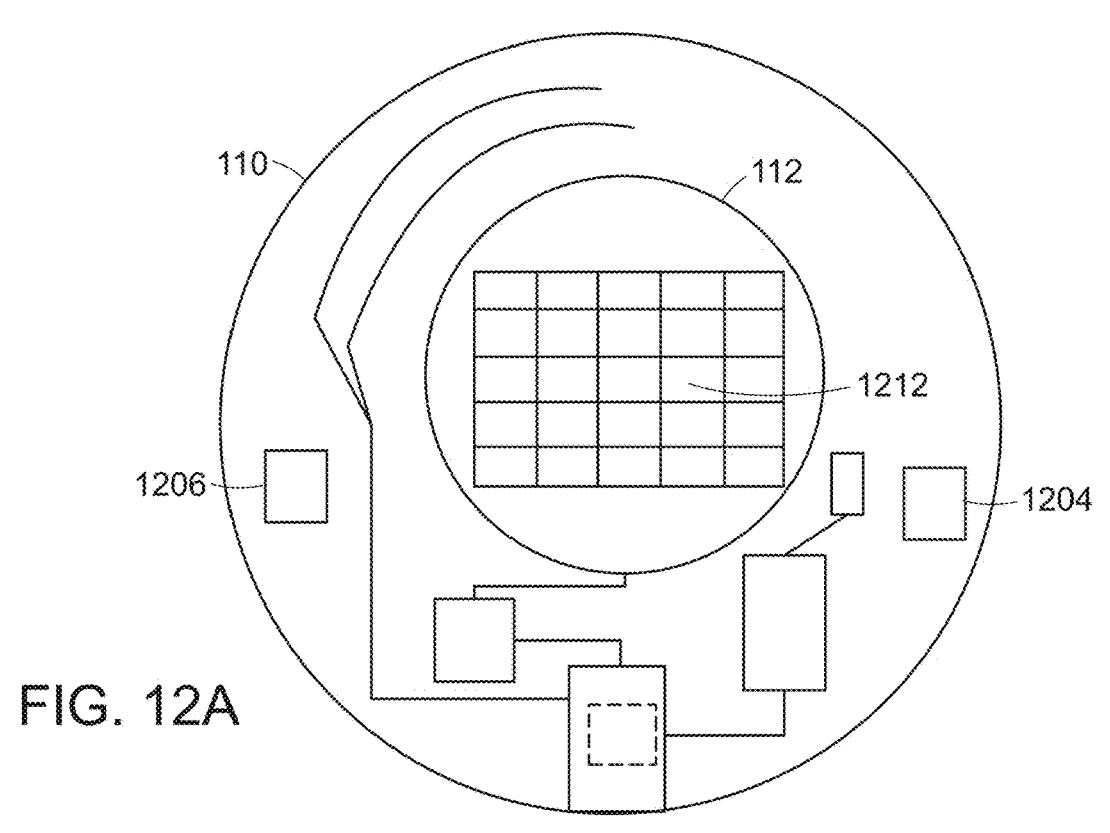
FIGS. 12A and 12B illustrate alternative embodiments of a pressure sensor in accordance with some embodiments of the present application.
Figure 12B:
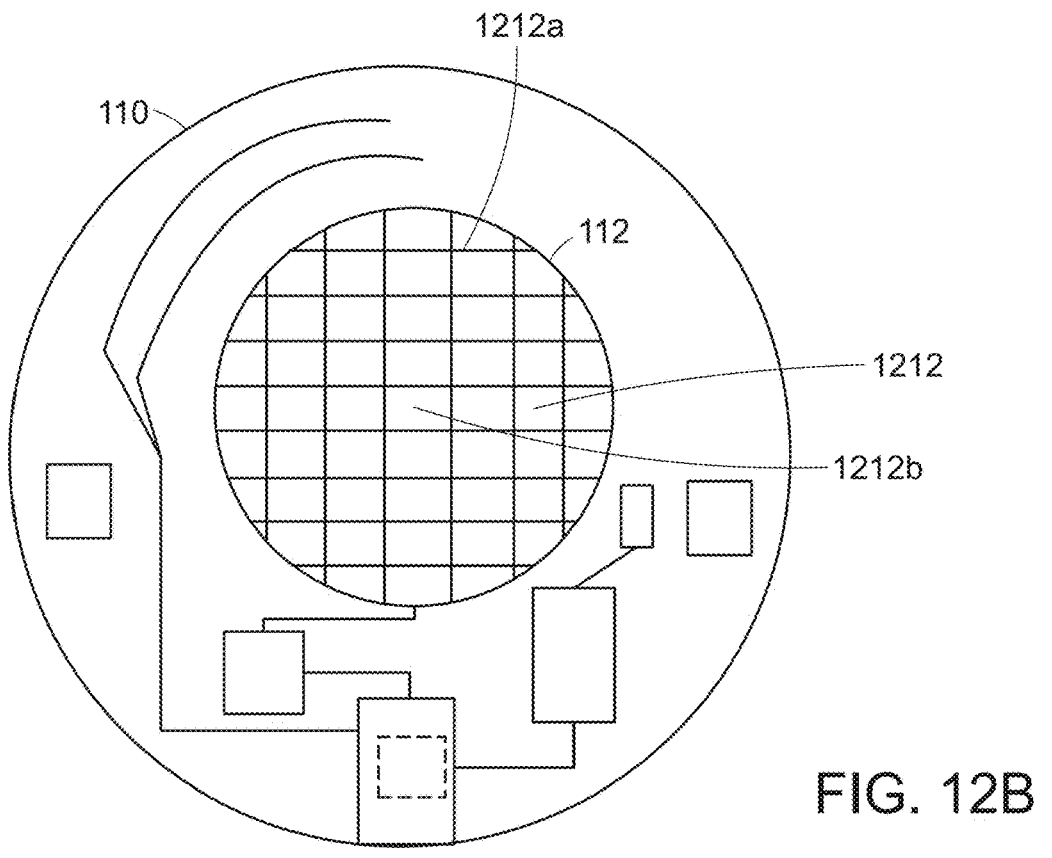

FIGS. 12A and 12B illustrate alternative embodiments of sensor devices 110 having pressure sensors 112 in accordance with some embodiments of the present application. In accordance with various embodiments, the pressure sensor 112 can include a single active area as shown above with reference to FIG. 1 or can include an array of pressure-sensitive areas as shown in FIGS. 12A and 12B. In FIG. 12A, the pressure sensor 112 includes an array of pressure-sensitive areas 1212 wherein an area of each of the pressure sensitive areas is the same. In FIG. 12B, the pressure sensor 112 includes an array of pressure-sensitive areas 1212 wherein an area of the each of the pressure-sensitive areas is not necessarily the same. For example, the sensing area of the pressure-sensitive area 1212a at the edge of the pressure sensor 112 is lower than the sensing area of the pressure-sensitive area 1212b near the middle of the pressure sensor 112.

In some embodiments, the sensor device 110 can include a radio-frequency identification device (RFID) chip 1204. The RFID chip 1204 can communicate with a scanner 604 of the tablet 600 or computing system as described above with reference to FIGS. 6D and 6E. The RFID chip can include unique identifying information for the sensor device 110 such as a serial number. In some embodiments, the scanner 604 of the tablet 600, such as a machine reader, can receive the unique identifying information and can transmit instructions to the sensor device 110 to initialize or power up to prepare to receive further instructions.

In some embodiments, the sensor device 110 can include a machine-readable pattern 1206 that encodes unique identifying information. For example, the machine-readable pattern 1206 can include a one-dimensional pattern such as a barcode or a two-dimensional pattern such as a quick response code. In various embodiments, the scanner 604 of the tablet 600 can scan the machine-readable pattern 1206 (e.g., by imaging the pattern using an imaging device) to gather the unique identifying information and identify the sensor unit 110.

In various embodiments, the pressure-sensitive areas 1212 of the pressure sensor 112 can be implemented as separate devices or as neighboring areas integrated into a single device. As an example of the former, the pressure sensor 112 can include an array of discrete aligned sensing elements that individually output data values. Alternatively, the array of pressure-sensitive areas can be implemented as, for example, addressable portions of a larger sensing element. In some embodiments, the pressure sensor 112 can have between 12 and 128 pressure-sensitive areas or sensor elements, more preferably, between 50 and 70 pressure-sensitive areas. In some embodiments, a dimension (e.g., length or width) of each pressure-sensitive area or sensor element can be in a range from 0.5 to 1 cm. Data collected from arrayed pressure-sensitive areas such as those depicted in FIGS. 12A and 12B can be displayed in a two-dimensional format to indicate locations on the body portion to which the sensor device 1110 is attached where pressure is higher or lower. A graphical representation of this "pixelated" pressure data is described above with reference to FIG. 6D.

In some embodiments, the system can separate data by subregion of pressure-sensitive areas or elements and treat the data differently by subregion. For example, the system can threshold different subregions differently. In some embodiments, the system can interrogate the sensor device 110 periodically and take action if no pressure has been measured for a period of time. For example, if no pressure has been measured over a period of several minutes, the system can conserve power by subsequently polling only a subregion of the array of pressure-sensitive elements rather than gathering data from all elements.

In some embodiments, systems and methods described herein can utilize the array of pressure-sensitive areas or pressure elements to optimize placement of the sensor device 110 on the patient. For example, if a particular subregion to the edge of the pressure sensor 112 senses pressure consistently while another region does not, the location of the sensor device 110 may need to be adjusted on the patient to position the peak pressure in the center of the pressure sensor 112. In some embodiments, the system can detect off-center pressure application and provide a notice to a user (for example, through the GUI 602) that the location of the sensor device 110 should be adjusted.

A preferred embodiment can utilize a neural network as an adaptive computational system whereby data is accumulated for a particular patient, and/or particular classes of patients and/or classes of body locations and/or therapeutic indications. Processors, such as graphics processors, available from Nvidia Corporation, Santa Clara Calif., are integrated into the tablet system, for example, or alternatively, can be connected by a communication network to a plurality of individual systems associated with a given network such as a hospital or group of networked hospitals, clinics or other patient treatment sites. Each sensor array can generate a two dimensional distribution or image of data that varies over time. The data can be integrated over time by the neural network processor.

Figure 13A:
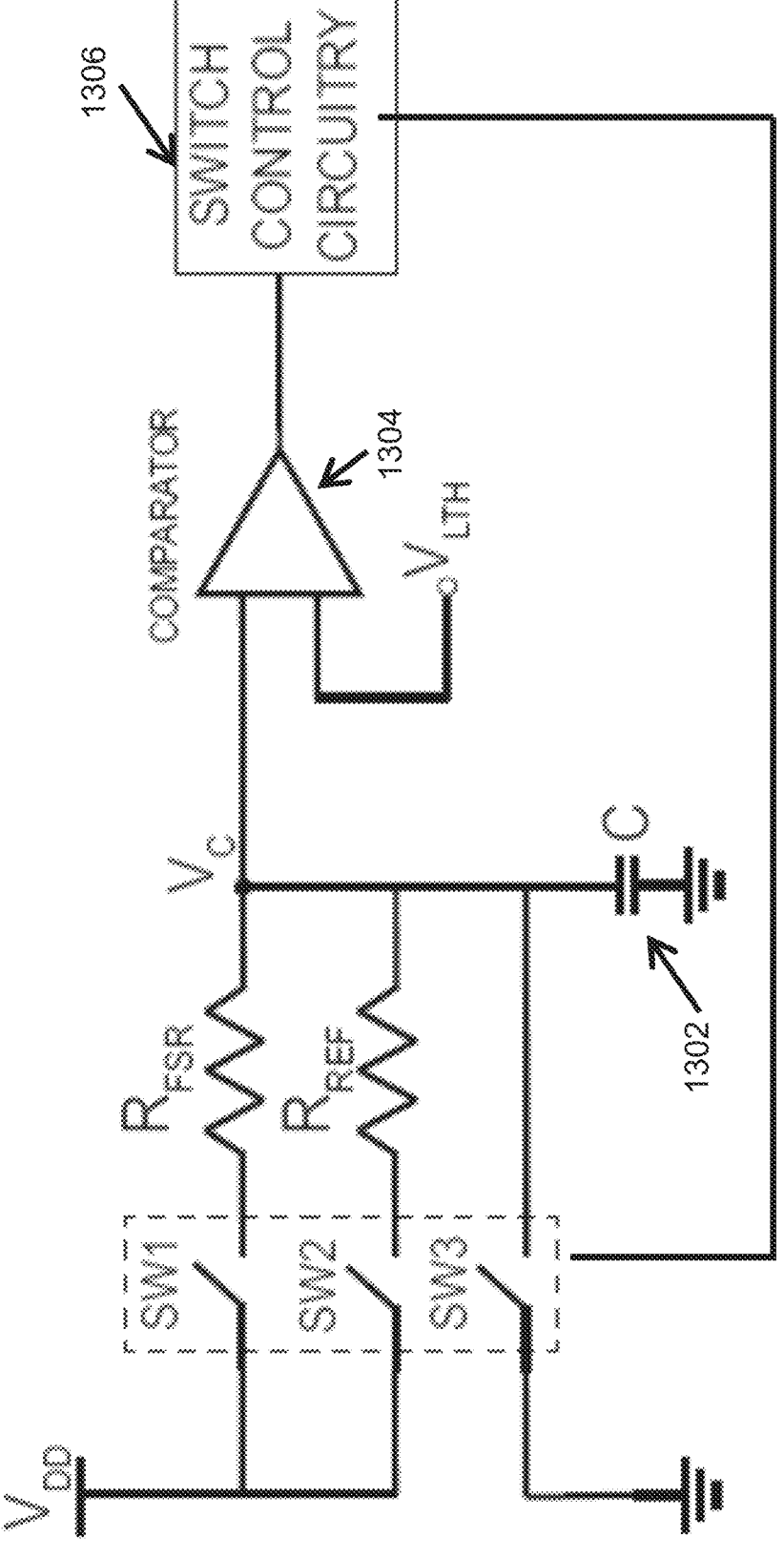
FIG. 13A illustrates a high-level schematic of a time-based resistance measurement in accordance with embodiments of this application.
Figure 13B:
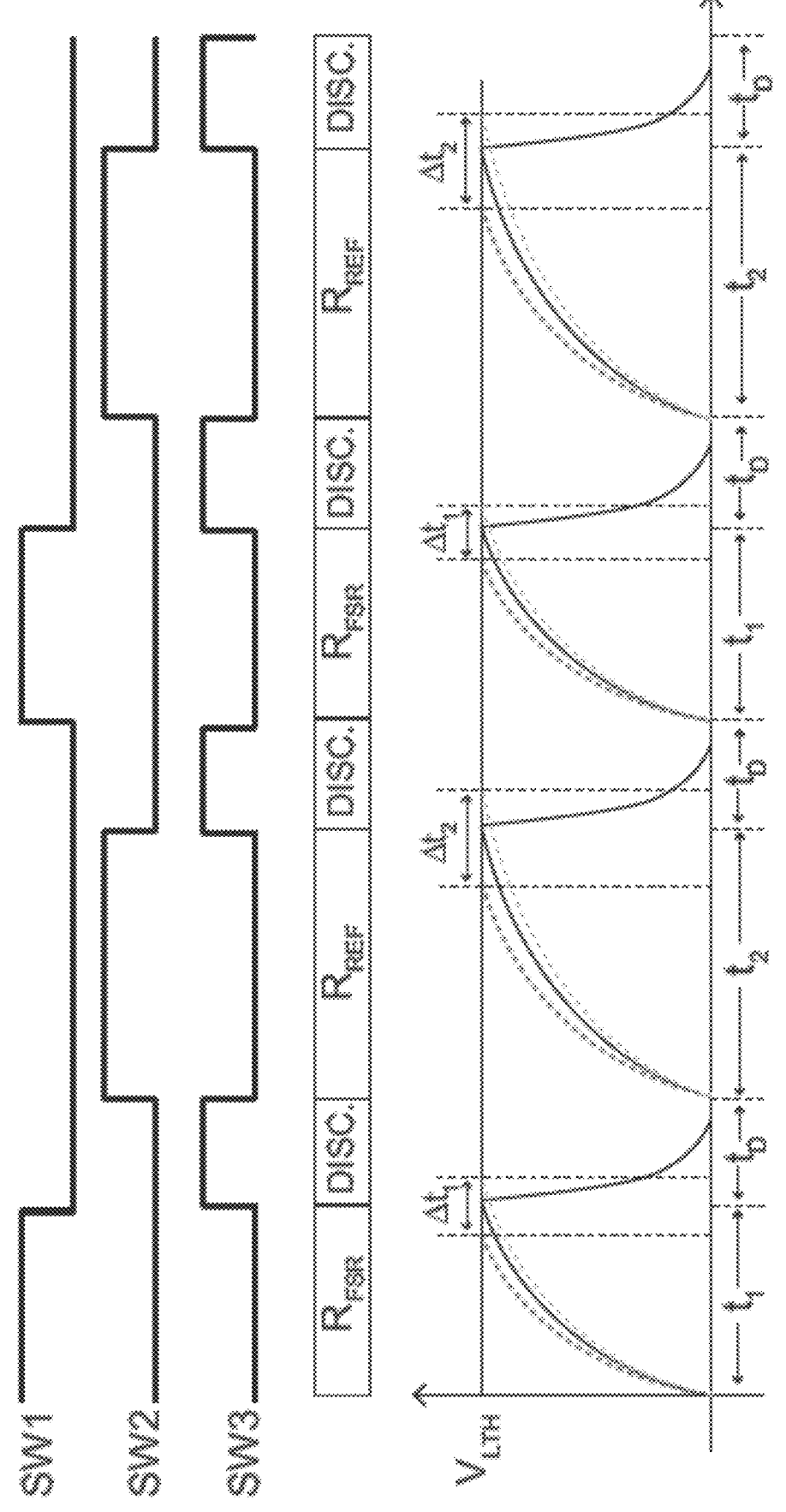
FIG. 13B illustrates a timing diagram for the switches SW1, SW2, and SW3.

FIG. 13A illustrates a high-level schematic of a time-based resistance measurement in accordance with embodiments of this application. FIG. 13B illustrates an exemplary timing diagram of the schematic system of FIG. 13A. In FIG. 13A, when the switch SW1 is enabled, the capacitor 1302 is charged via the resistor $R_{FSR}$. The voltage across the capacitor $V_C$ is compared to the threshold voltage $V_{LTH}$ through a comparator 1304. When the comparator 1304 judges that $V_C > V_{LTH}$, the switch SW1 can be disabled using switch control circuitry 1306. The capacitor 1302 is then discharged by enabling switch SW3 using the switch control circuitry 1306. Next, switch SW2 can be enabled, and the capacitor 1302 can be charged via the resistor $R_{REF}$. When $V_C$ becomes greater than $V_{LTH}$, switch SW2 can be disabled using the switch control circuitry 1306 and the capacitor 1302 is discharged via the switch SW3. In exemplary embodiments, the output of the comparator 1304 controls decision making by the switch control circuitry 1306.

FIG. 13B illustrates a timing diagram for the switches SW1, SW2, and SW3. The figure also shows the charging and discharging waveform of $V_C$ in the system as described above for FIG. 13A. The charging time of the capacitor 1302 through the resistor $R_{FSR}$ is denoted as $t_1$ and the charging time of the capacitor 1302 through $R_{REF}$ is denoted as $t_2$. $t_D$ denotes the time it takes to discharge the capacitor 1302. In some embodiments, $t_D$ can be assumed to be negligible compared to $t_1$ and $t_2$. Taking the ratio of the two measured values of time, $$\frac{t_2}{t_1} = \frac{R_{REF}C}{R_{FSR}C} \tag{5}$$

$$R_{FSR} = \frac{t_1 R_{REF}}{t_2} \tag{6}$$

As shown in the waveforms of FIG. 13B, values of $t_1$ and $t_2$ can vary due to various factors. This variation in time is denoted as $\Delta t_1$ and $\Delta t_2$, where $\Delta t_1$ is the variation in time $t_1$ and $\Delta t_2$ is the variation in time $t_2$. Thus, we can say that measured time $t_{(M)}$ is a combination of real time $t_{(R)}$ and the variation in time measurement $\Delta t$, i.e., $$t_{(M)} = t_{(R)} \pm \Delta t \tag{7}$$

The ratio of the measured time gives $$\frac{t_{2(M)}}{t_{1(M)}} = \frac{T_{2(R)} \pm \Delta t_2}{T_{1(R)} \pm \Delta t_1} \tag{8}$$

Expanding this equation, we get, $$\frac{t_{2(M)}}{t_{1(M)}} = \frac{t_{2(R)}\left(1 \pm \dfrac{\Delta t_2}{t_{2(R)}}\right)}{t_{1(R)}\left(1 \pm \dfrac{\Delta t_1}{t_{1(R)}}\right)} \tag{9}$$

$$\frac{t_{2(M)}}{t_{1(M)}} = \frac{t_{2(R)}}{t_{1(R)}}\left[1 + \frac{\Delta t_2}{t_{2(R)}} \pm \frac{\Delta t_1}{t_{1(R)}}\right] \tag{10}$$

where the term $$\frac{\Delta t_2}{r_{2(R)}} \pm \frac{\Delta t_1}{r_{1(R)}}$$

represents the fractional error. In an exemplary system, it can be desirable to maximize accuracy at a pressure of 30 mmHg, which is the the threshold beyond which capillary blood flow is reduced. $R_{FSR}$=10 kΩ is approximately equal to a pressure of 30 mmHg. In such a case, the goal is to calculate the bounds of worst case fractional error and its exact value at $R_{FSR}$=10 kΩ. Taking into account the worst case fractional error, $$\varepsilon = \frac{\Delta t_2}{t_{2(R)}} + \frac{\Delta t_1}{t_{1(R)}} \tag{11}$$

$$\varepsilon = \frac{\Delta t}{C}\left[\frac{1}{R_{REF}} + \frac{1}{R_{FSR(min)}}\right] \tag{12}$$

where $\Delta t$ is the maximum time error for every rise time measurement. According to this exemplary analysis, the worst case for $\Delta t$, i.e., $\Delta t_{MAX}$=92 μS, and the typical value of $\Delta t$ is $\Delta t_{TYP}$=32 μS.

Figure 13C:
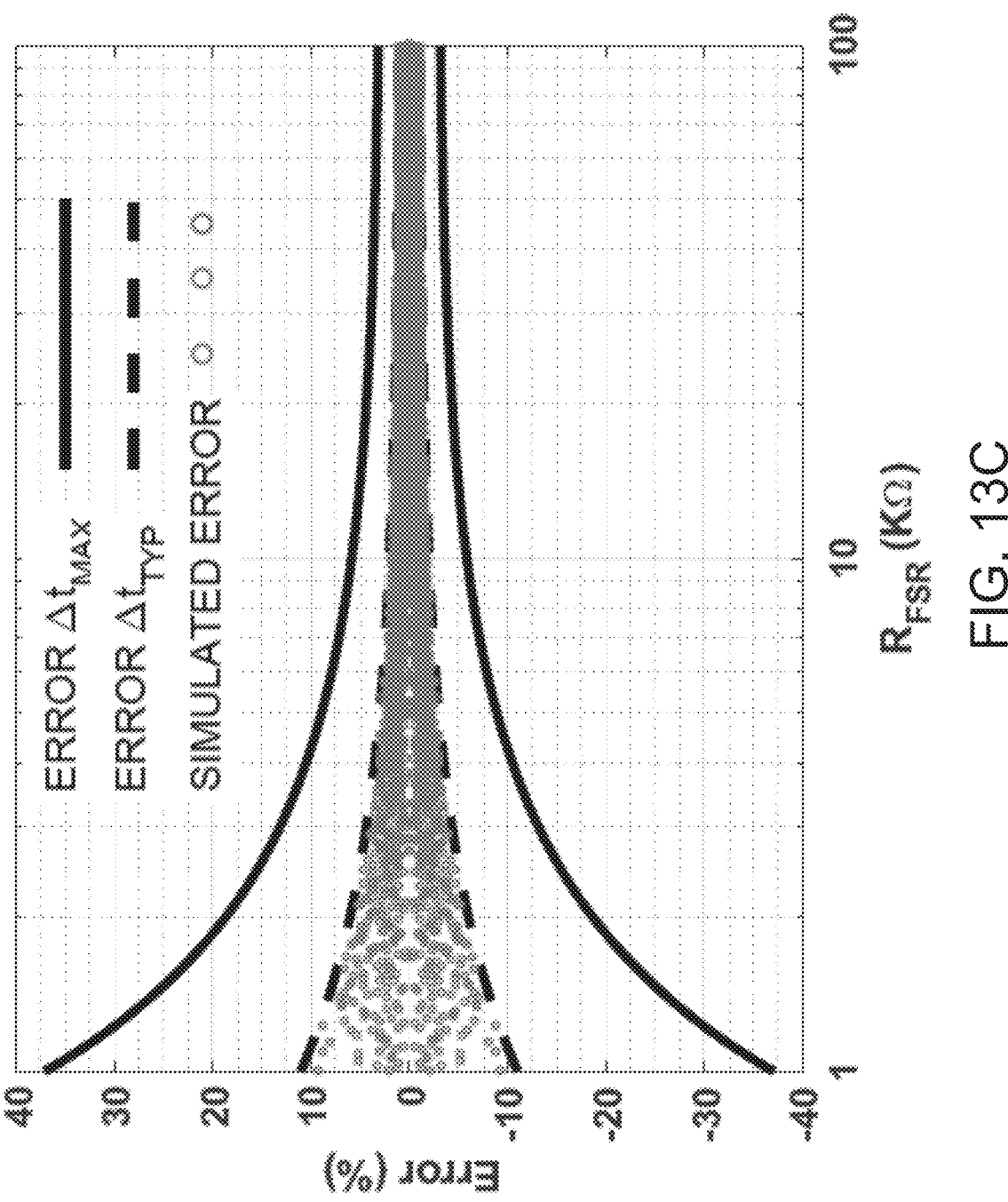
FIG. 13C illustrates a Monte Carlo simulation of measurement error along with worst case typical and maximum errors.

The analysis can be expanded by simulating variation of the value of $R_{FSR}$ from 1 kΩ to 100 kΩ for both $\Delta t_{MAX}$ and $\Delta t_{TYP}$ and taking $R_{REF}$=10 kΩ. FIG. 13C shows the comparison of the worst case error for $\Delta t_{MAX}$ and $\Delta t_{TYP}$ along with Monte Carlo simulation by introducing error in random form. The Monte Carlo simulation shows that the randomly simulated error is within the bounds of the worst case error for any given value of $R_{FSR}$. In addition, the worst case error at $R_{FSR}$=10 kΩ is within ±1% for $\Delta t_{TYP}$ and within ±5% for $\Delta t_{MAX}$ The value of the capacitor 1302 can be selected to set the expected error of the measurement. For example, the value of the capacitor 1302 identified using Equation 12 for the error to be within 1% at $R_{FSR}$=10 kΩ is 640 nF. From the error analysis depicted in FIG. 13C, using a single capacitor 1302 can potentially cause a high measurement error. As the value of applied pressure increased, the value of $R_{FSR}$ decreases according to the power-law expression described in Equation (9). The worst case error can be as high as ±37% for $R_{FSR}$=1 kΩ. This can be rectified by using a larger capacitor.

A larger capacitor would decrease the measurement error. But when the value of $R_{FSR}$ is high, the measurement time will increase by a considerable amount. This can be detrimental to the system as the value of the pressure applied can change quickly and the technique might not be able to capture measurements on a sufficient time-scale. Thus, the system in some embodiments includes one or more additional capacitors (e.g., C2) in parallel to the capacitor 1302 C1 when $R_{FSR}$ decreases. The second capacitor can be bigger than the first one, e.g., C2 can be approximately four times bigger than C1 in some embodiments.

When the second or higher number capacitor (C2) is added in parallel to the first capacitor 1302 (C1), the overall capacitance increases. While increased capacitance can reduce the measurement error, increasing the overall value of C can cause $t_2$ to increase as well because $R_{REF}$=10 kΩ. To overcome this problem, some systems according to the present disclosure can include another reference resistor, i.e., $R_{REF2}$. In accordance with various embodiments, $R_{REF2}$ can be smaller than the first reference resistor, $R_{REF1}$. In some embodiments, the second or higher reference resistor ($R_{REF2}$) can have a value that is ten times lower than the value of the first reference resistor.

In some embodiments, the values of one or more of the reference resistors and one or more of the capacitors can be configurable to optimize the design as the value of $R_{FSR}$ changes. For example, when the applied pressure increases, the value of $R_{FSR}$ decreases. In response, the system can add C2 in parallel to C1 in order to ensure the error does not increase. At the same time, $R_{REF2}$ needs to be used in place of $R_{REF1}$ in order to ensure that $t_2$ does not increase. Similarly, as the applied pressure decreases, and $R_{FSR}$ increases, the system can reconfigure to use only C1 and $R_{REF1}$.

Figure 13D:
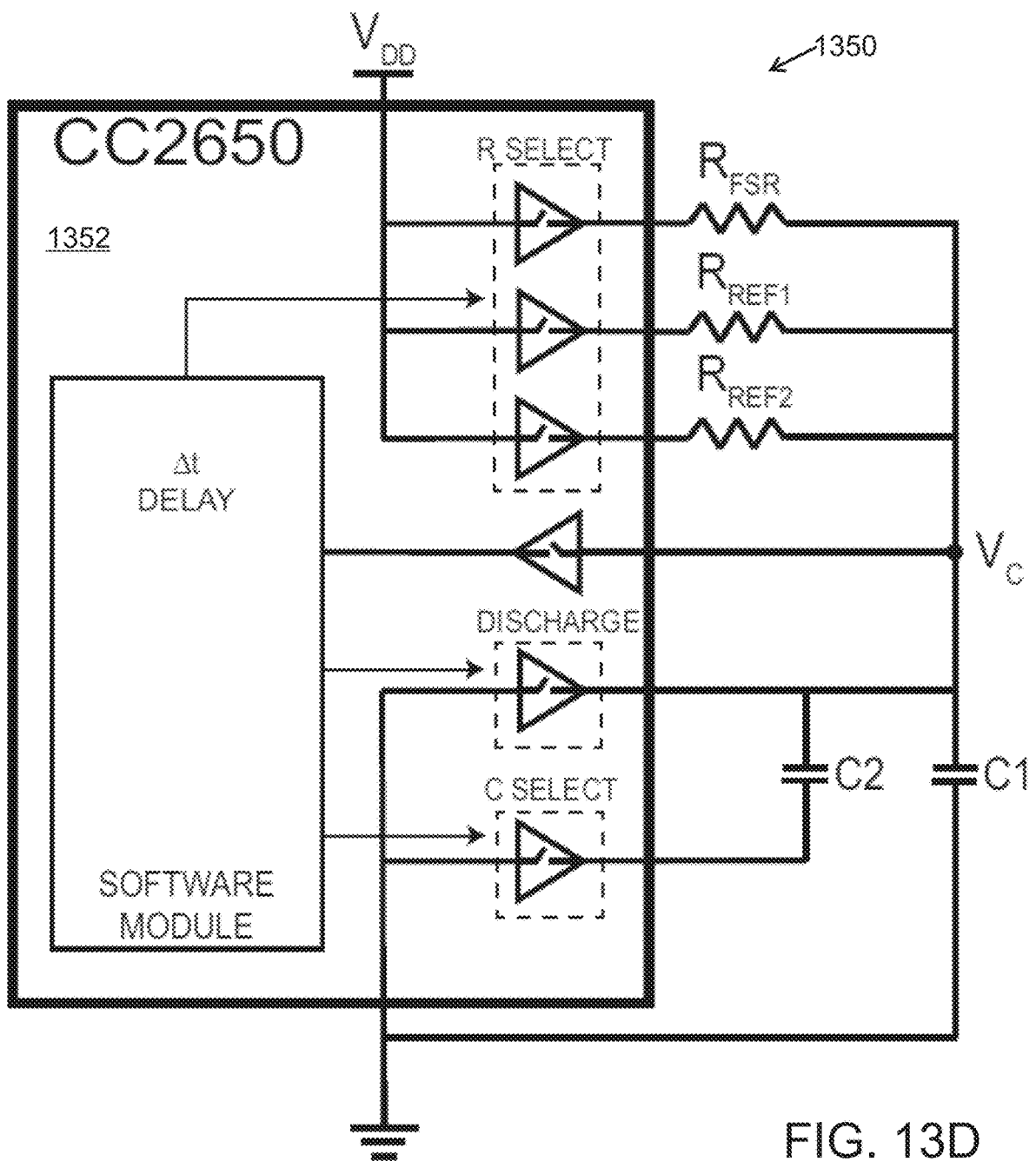
FIG. 13D illustrates an exemplary system for a time-domain-based measurement calibration technique in accordance with various embodiments described herein.

FIG. 13D illustrates an exemplary system 1350 for a time-domain-based measurement calibration technique in accordance with various embodiments described herein. The system is implemented as shown in FIG. 6. The system 1350 includes a processor 1352 such as a microprocessor that is configured to execute instructions to open or closes switches to enable or disable specific resistors (R select), to enable or disable specific capacitors (C select), or to discharge the voltage. In some embodiments, the input/output pins of the processor 1352 are tri-state switches. The resistors $R_{FSR}$, $R_{REF1}$, and $R_{REF2}$ are connected via output pins of the processor 1352. When the processor 1352 executes instructions to enable one of these resistors, the resistor is connected to $V_{DD}$. Capacitor C1 stays connected at all times and discharges through the discharge switch when the switch is enabled. The discharge switch connects the capacitor to ground. Capacitor C2 can be added in parallel to C1 by enabling the switch labeled C Select. The switches defining R Select, discharge, and C Select can be controlled by the software module of the processor 1352.

The software module of the processor 1352 controlling the switches can be configured in such a way that it enables the resistor $R_{REF1}$ and the capacitor C1 for higher values of the resistor $R_{FSR}$. When the resistor $R_{FSR}$ decreases, the processor 1352 can execute instructions from the software module to enable the resistor $R_{REF2}$, to disable the resistor $R_{REF1}$, and to enable the capacitor C2 such that it is in parallel with the capacitor C1. By taking this action, the system 1350 can reduce the measurement error while also ensuring that the charging time is not too high. This configurability of the system 1350 gives the system 1350 the ability to change the values of resistance and capacitance in the sensing circuit as the value of $R_{FSR}$ changes.

Figure 13E:
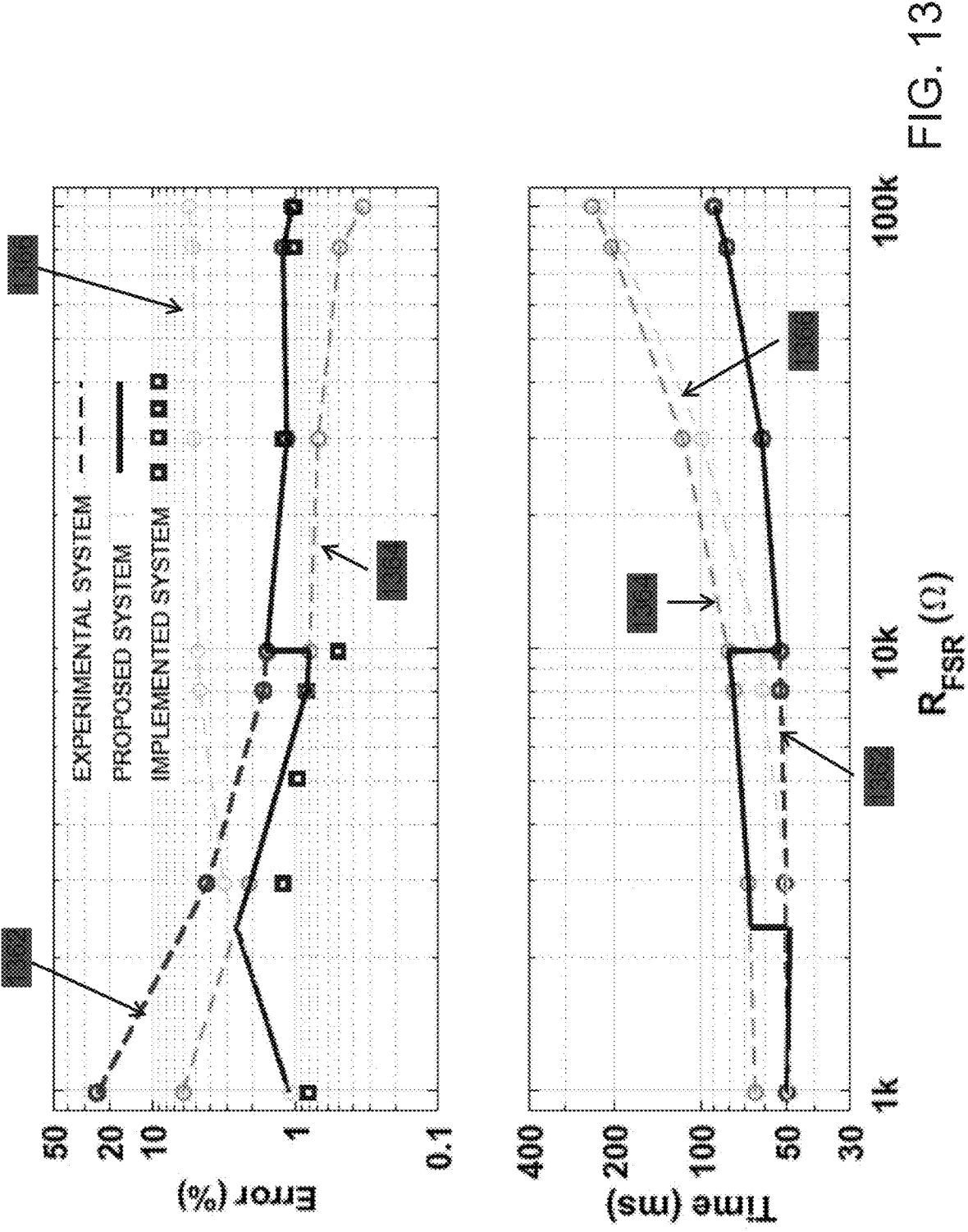
FIG. 13E illustrates experimental results from the system of FIG. 13D.

FIG. 13E illustrates experimental results from the system 1350. The dashed lines in the upper plot of FIG. 13E shows the experimental error for each of three static scenarios. The system configuration for plot 1362 includes only the capacitor C1 and a value of the resistor $R_{REF1}$=10 kΩ. The system configuration for plot 1364 includes both capacitor C1 and capacitor C2 and a value of the resistor $R_{REF1}$=10 kΩ. The system configuration for plot 1366 includes both capacitor C1 and capacitor C2 and a value of the resistor $R_{REF1}$=1 kΩ. The lower plot of FIG. 13E shows the charging time for the three static scenarios (dashed lines) as $R_{FSR}$ varies from 1 kΩ to 100 kΩ.

The results in FIG. 13E highlight the advantages of having a reconfigurable system 1350 where the processor 1352 of the system 1350 can change the value of capacitance and resistance for total reference resistance $R_{REF}$. The solid lines in FIG. 13E show the ideal configuration of the system 1350 in order to control both the error and charging time within acceptable limits over a range of sensor resistance output values. As $R_{FSR}$>10 kΩ, the processor 1352 can execute instructions to control the switches to enable only the resistor $R_{REF1}$ and the capacitor C1 in the circuit. As $R_{FSR}$ falls below 10 kΩ, the processor 1352 can add the capacitor C2 in parallel to the capacitor C1. In this situation, the measurement error is reduced while the charging time is increased but still may stay within acceptable limits. When $R_{FSR}$≥2.5 kΩ, the processor 1352 can execute instructions to cause the switches to enable $R_{REF2}$ to reduce measurement error and charging time as the value of $R_{FSR}$ decreases. The open squares in the upper plot of FIG. 13E represent an implementation of the reconfigurable system 1350 described herein as $R_{FSR}$ is varied from 1 kΩ to 100 kΩ. The system 1350 follows the pattern of the proposed system shown in the solid line.

Advantageously, the time-domain based force measurement system does not require use of a reference voltage or analog-to-digital converter and, thus, is more easily interoperable with standard digital components.

Figures 14, 15:
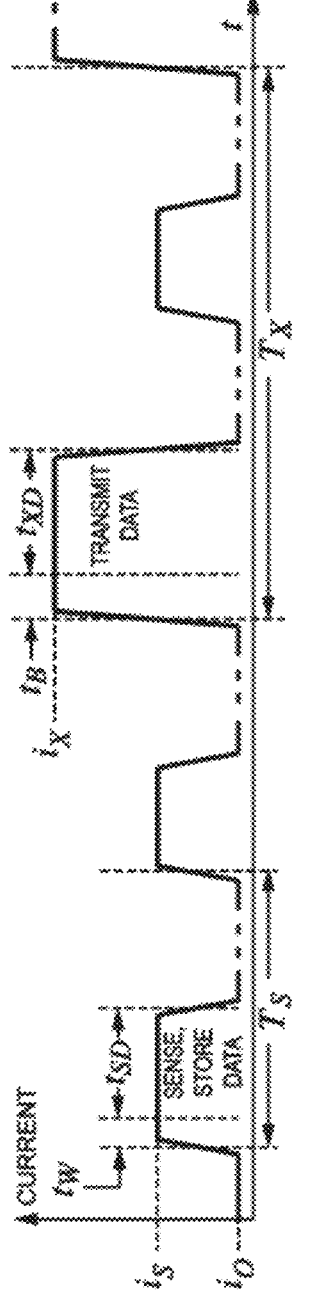
FIG. 14 illustrates a schematic of a timing diagram to regulate power consumption in accordance with various embodiments described herein.
FIG. 15 illustrates a table with the contribution of each component of processor current consumption with respect to the total average current.

To minimize power consumption in the sensing device 110, the microprocessor 135 and transmission/reception by the communications electronics (e.g., wireless communications 118 and/or near field communications 128) can be activated only when necessary to meet system throughput requirements. FIG. 14 illustrates a schematic of a timing diagram to regulate power consumption in accordance with various embodiments described herein. System resource operation is described as follows:

Sleep: Background current $i_0$ is always being consumed.

Sensing: The microcontroller wakes up and senses physical quantities every $T_s$ seconds. When active for obtaining sensing data, the microprocessor 135 can consume a current of $i_s$. Waking up occurs over a time $t_w$, followed by a time $t_{SD}$ to complete sensing and data acquisition. $D_S$ bits of data are generated during each sensing time. Thus, the total charge drawn from the battery 111 for one sensing event is given by the expression $$q_s = i_S(t_W + t_{SD}) \tag{13}$$

and the average current required for sensing is given by the expression $$i_{S(AVG)} = \frac{q_S}{T_S} = i_S \frac{t_W}{T_S} + i_S \frac{t_{SD}}{T_S} \tag{14}$$

where the expression $i_S$ $$\frac{t_W}{T_S}$$

represents current consumed during wake up by the microprocessor 185 and $i_S$ $$\frac{t_{SD}}{T_S}$$

represents current consumed during sensing. For both terms, the goal of minimizing power consumption drives toward the largest $T_S$ possible while maintaining a time resolution adequate for the physical processes being sensed. Preliminary results in indicate that a time of $T_S = 1$ second may be adequate in some embodiments.

Transmitting: The microprocessor 185 wakes up and transmits data every $T_X$ seconds. When active for transmitting, the microprocessor 185 consumes a current $i_X$. Before data can be transmitted, a time $t_B$ is required to establish the wireless link to the server, e.g., using Bluetooth Low Energy (BLE). Transmission of sensed data requires a time $t_{XD}$ at a data rate equal to the link capacity of C bits/second. Thus, the charge required for one transmission event is $$q_X = i_X(t_B + t_{XD}) \tag{15}$$

and the average current required for transmission is $$i_{X(AVG)} = \frac{q_X}{t_X} = i_X\left(\frac{t_B}{T_X} + \frac{t_{XD}}{T_X}\right) \tag{16}$$

We can gain more insight into this equation by observing that the amount of data sent over the link must be equal to the total amount of data generated by sensing. Because there are $T_X/T_S$ sensing events between each transmission:

$$D_S \frac{T_X}{T_S} = C t_{XD} \rightarrow t_{XD} = \frac{D_S}{C}\frac{T_X}{T_S} \tag{17}$$

Combining the last two expressions gives:

$$i_{X(AVG)} = i_X \frac{t_B}{T_X} + i_X \frac{D_S/T_S}{C} \tag{18}$$

Where the first term represents current consumption for establishing the wireless link and the second term represents current consumption for transmission. Thus, the total current is the sum of current consumed for link overhead and current required for transmitting sensed data.

With respect to the current needed to establish the link the goal of minimizing power consumption drives use of the largest $T_X$ possible while maintaining a time increment adequate for alerting the patient or caregiver to the risk of tissue damage, Since the time required for tissue necrosis is many minutes even for high pressure cases, some embodiments described herein can utilize $T_X = 60$ seconds.

With respect to the current needed to transmit data, the current $i_X$ is scaled by the ratio of the sensor output data rate Ds/Ts relative to the link capacity C. In some embodiments, each of the three sensed quantities results in a 16 byte data word as the output. To send the output from each sensor (e.g., pressure sensor, temperature, moisture, etc.), the size of the data word is multiplied by the number of sensed quantities to be sent. For example, six sensor would produce a total of Ds=96 bytes per sensing event. FIG. 15 illustrates a table with the contribution of each component to the total average current of 315 µA in this example. Due to the low data rate and infrequent transmission, the dominant contributor to the power consumption is background power consumption, with the power required for sensing as the only other appreciable component. The battery capacity required to support an average current draw of 315 µA for 7 days is 53 mA-hr, which is within the range of present-day lithium polymer battery technology.

The pressure ulcer monitoring system 100 described herein was used to measure ulcer formation in experiments with rats. The goals of the study were to determine the extent of injury caused by formation of a pressure ulcer and how the injury changes over time.

The National Pressure Ulcer Advisory Panel (NPUAP) stages pressure injury as seen in Table I. Since our goal is prevention of any of these stages, we can consider a binary outcome: no damage on the one hand or any pressure injury (Stages 1 to 4 or unstageable). In some embodiments, a probit analysis can be used to analyze the collected data. Probit analysis is a type of regression used to analyze binomial response variables that transforms a sigmoid-dose response curve into a straight line that can be analyzed by regression. Pressures of 30-60-90-120-150 mmHg, and times of 1-2-4-6-8 hours were used during the experiment of pressure and time. The probit analysis can be used to determine the probability of developing a pressure ulcer at clinically relevant pressures and time points.

TABLE I

| STAGE | DEFINITION |
|---|---|
| 1 | Nonblanchable erythema |
| 2 | Partial-thickness skin loss with exposed dermis |
| 3 | Full thickness skin loss with exposed adipose tissue (fat) or granulation tissue present |
| 4 | Full thickness skin loss with exposed fascia, muscle, tendon, ligament or bone at the base of the wound |
| Unstageable | Full thickness skin loss in which the extent of the injury cannot be confirmed due to overlying slough or eschar |

Figure 16:
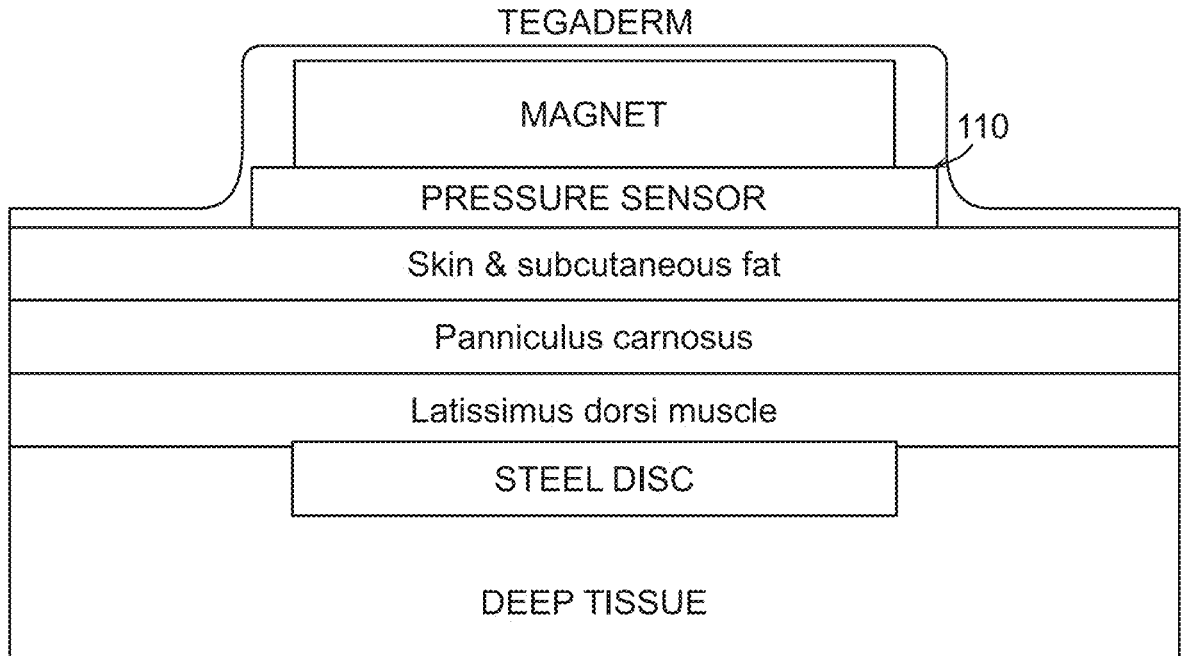
FIG. 16 illustrates a schematic of intraoperative placement of the magnetic disc in animal experiments using a pressure ulcer monitoring system according to the present description.

Sprague-Dawley rats underwent a surgical procedure for steel disc implantation. While under anesthesia, circular magnetic discs are implanted deep into the latissimus dorsi muscle of the rats. FIG. 16 illustrates a schematic of intra-operative placement of the magnetic disc. Two discs are implanted with one on each of the dorsal flanks of the rat. This ensures that each rat can serve as its own control. After the animals recover from the surgical procedure, magnets are applied to the skin surface according to the cohort being tested. Data regarding pressure and time are collected using a pressure ulcer monitoring system 100 as described herein in order to to predict the probability of pressure ulcer formation. Over the subsequent three days, the area of injury is examined and clinically graded (i.e., no injury vs. grades 1-4 or ungradeable ulcers) as it demarcates. On post-operative day 15, the animals are euthanized. At that time, the final visual grading of pressure ulcers took place. Biopsies of the resulting area of the injury were taken and sent for histology to confirm the grade of injury.

The five cohorts that were tested were 150 mmHg, 120 mmHg, and 90 mmHg for 4 hours each, 60 mmHg for 6 hours, and 30 mmHg for 8 hours. FIG. 17 shows the results of the experimental protocol for five rats. Each of the 5 rats developed a pressure ulcer. On the day of sacrifice, the size of the pressure injury was measured, and visible skin ulceration was clinically graded. Each of the 5 rats had a stage 2 pressure ulcer. We can see in FIG. 17 that the actual pressure range is more than the nominal pressure. This is due to the technique being used. As the magnet and the steel plate are pulled towards one another due to the magnetic force, it causes the fluids in the tissues to flow out, decreasing the distance between the magnet and the steel plate. In turn, the magnetic pull is increased. This leads to a situation where the applied pressure increases monotonically until equilibrium is achieved.

We can see the various stages of damage to both skin and muscle due to the different levels of pressure applied for certain time intervals. It should be noted that all rats exhibited mild foreign body reaction at the deep surface in both the experimental and control flanks. This is mainly due to the presence of the steel discs. Histological evidence shows that the right side (magnet application site) exhibited damage and physiological changes to the epidermal layer of the skin and into the muscle. Conversely, the left side (control side) exhibited no tissue or muscular damage. This suggests that the foreign body reaction on both sides was not indicative of the damage and physiological changes present on the right side. Hematoxylin & eosin were used as the stains for the histological evaluation. The images in FIG. 17 have magnification set at 4× and scale bar=10 μm.

At the pressure of 150 mmHg, Rat 1 exhibited mild damage in the panniculus carnosus, where heavy neutrophil granulocyte infiltration and tissue disruption can be seen on the magnet side. Similar damage was also observed in the latissimus dorsi of the rat. Histology reveals no muscle fiber disruption on the control side.

Rat 2 was subjected to 120 mmHg of pressure for 4 hours. It shows similar but slightly less damage in the latissimus dorsi and the panniculus carnosus. It also had moderate to severe neutrophil granulocyte infiltration in addition to moderate epidermal damage. Similar to Rat 1, histology reveals no muscle fiber disruption on the control side of Rat 2.

90 mmHg of pressure was applied to Rat 3 for 4 hours. At a lower pressure for the same duration compared to Rat 1 and 2, this rat did not show any histological damage to the latissimus dorsi or the panniculus carnosus. However, it can be seen that the magnet side changes in nuclei density and some immune cell infiltration as compared to the control side. This means that the muscles on the magnet side are experiencing low grade inflammation that would potentially lead to muscle disruption and muscular damage. This rat exhibited minimal epidermal damage.

For Rat 4, 60 mmHg of pressure was applied for 6 hours. Compared to the previous animals, Rat 4 experienced a decreased pressure for a longer duration. Rat 4 started showing some thickening of the latissimus dorsi, with slight muscle fiber disruption. The rat exhibited no epidermal damage. Histology of Rat 4 reveals no muscle fiber disruption on the control side.

Lastly, Rat 5 was subjected to 30 mmHg of pressure for 8 hours. This rat showed no signs of muscle fiber disruption on either the control side or on the magnet side. However, the rat exhibited tissue disruption and minimal epidermal damage on just the magnet side.

In this cohort, we have shown that there is strong clinical correlation in the magnitude and time duration of applied pressure with the extent of injury. At higher pressures (e.g., Rat 1 and Rat 2), the extent of injury increased. The panniculus carnosus of the rat had heavy neutrophil granulocyte infiltration, along with damage to the latissimus dorsi of the rats. Muscle fiber disruption was also evident.

In regard to Rat 3 (90 mmHg for 4 hours) and Rat 5 (30 mmHg for 8 hours), these rats exhibited no visible muscular level damage. They only exhibited minimal epidermal damage. While Rat 4 (60 mmHg for 6 hours) was beginning to show some thickening of the latissimus dorsi. The explanation can be due to the effects of the animal's physical activity or potentially exhibiting microvascular trauma. Physical activity increases the resistance that muscle has to acute damage and inflammation due to the heavy presence of chemokines and molecular pathways that play a role in the homeostasis of myofibres. These low pressures may be inducing some local acute inflammation that is being attenuated by satellite cells and local immune cells, hence why there is no muscle damage present but the commencement of immune cell infiltration. Histological evidence shows that the right side (magnet application side) exhibited damage and physiological changes to the epidermal layer of the skin and into the muscle, whereas the left side (control side) exhibited no tissue or muscular damage.

In some embodiments, the data processor can execute instructions to develop a diagnostic function by processing patient data using a machine-learning algorithm. Machine learning algorithms can assist in early identification and prediction of the onset of pressure ulcers so that preventive actions can be taken well before the pressure ulcer has formed. Machine learning algorithms can build a mathematical model of sample data or training data (e.g., patient data) that has the ability to make predictions or decisions without being explicitly programmed to perform the task. These machine learning algorithms can elucidate the relationships between variables of unknown dependency to better understand the correlations and dependencies between variables and provide predictive value. Machine-learning algorithms that can be used with embodiments described herein include, but are by no means limited to, linear regression, naïve Bayes, decision tree, k-nearest neighbor, random forest, support vector machines, convolutional or recurrent neural networks, Bayesian network models, long-term short-memory implementations, and other suitable implementations.

In some embodiments, the diagnostic function can be developed based on a machine-learning algorithm variant known as supervised learning. In supervised learning, the model or network is trained using both known inputs and corresponding known outputs as described in more detail below.

In some embodiments, the diagnostic function can be developed based on a deep learning variant of machine learning algorithms. Deep learning is based on data representation learning as opposed to task specific algorithms. Deep learning consists of multiple hidden layers in an artificial neural network. Through the process of model training, each level learns to transform its input data into a slightly more abstract and composite representation.

In some embodiments, the patient data that the machine learning algorithm will evaluate to produce the diagnostic function can include categories of data that are obtainable using a sensor patch such as pressure, temperature, relative humidity, 3-axis motion/accelerometer, bioimpedance. Many of these patient data categories include temporal data (i.e., data acquired over a period of time). Thus, the patient data can be representated as a time series. In some embodiments, the diagnostic function can perform time series forecasting, i.e., the diagnostic function can be used to predict future values based on previously observed values. For example, the machine-learning algorithm can include the use of one or more support vector machines (SVM), which are a form of supervised learning models, to investigate time series data. In some embodiments, long short-term memory (LSTM) implementations of machine-learning algorithms can be used in some embodiments. LSTM are units of a recurrent neural network (RNN), which are a form of deep neural networks. LTSM networks are well-suited to classify, process, and make predictions based on time series data because these networks can identify and account for lags (often of unknown duration) between important events in a time series.

Moreover, LSTMs are a form of RNNs that are capable of learning long-term dependencies. In other words, the networks can preserve information such as connections between nodes for long periods of time. In some embodiments, an LSTM block can include three gates (input, forget, and output), a block input, a single cell, an output activation function, and, optionally, one or more peephole connections. Peephole connections enable the input into the model of precise timings that can improve the learning rate for the model and/or enable the model to converge faster. In some embodiments, layers of the LSTM model can have weights that include one or more of input weights, recurrent weights, peephole weights, and bias weights. Relevant LSTM models that can be used to form a diagnostic function as described herein is described in "LSTM: A Search Space Odyssey" by Klaus Greff, et al., *IEEE Transactions on Neural Networks and Learning Systems*, Vol. 28, No. 10, October 2017, pp 2222-2232, and "Long Short-term Memory" by Sepp Hochreiter et al., *Neural Computation*, Vol. 9, Issue 8, 1997, pp. 1735-1780, and "*Simplifying Long Short-Term Memory Acoustic Models for Fast Training and Decoding*" by Yajie Miao et al., 2016 *IEEE International Conference on Acoustics, Speech and Signal Processing (ICASSP)*, March 2016, the entire contents of each of the publications being incorporated herein by reference.

The LSTM outputs are recurrently fed as the inputs. At time step t, the vector formulas of the computation can be described as:

$$i_t = \sigma(W_{ix}x_t + W_{ih}h_{t-1} + p_i c_{t-1} + b_i) \tag{19}$$

$$f_t = \sigma(W_{fx}x_t + W_{fh}h_{t-1} + p_f c_{t-1} + b_f) \tag{20}$$

$$c_t = f_t \odot c_{t-1} + i_t \odot \phi(W_{cx}x_t + W_{ch}h_{t-1} + b_c) \tag{21}$$

$$o_t = \sigma(W_{ox}x_t + W_{oh}h_{t-1} + p_o c_t + b_o) \tag{22}$$

$$h_t = o_t \odot \phi(c_t) \tag{23}$$

where $x_t$ is the input vector. The vectors $i_t$, $o_t$, $f_t$ are the activation of the input, output, and forget gates respectively. The $W_{\cdot x}$ terms are the weight matrices for the inputs $x_t$, the $W_{\cdot h}$ are the weight matrices for the recurrent inputs $h_{t-1}$, and the b terms are the bias vectors. The $p_i$, $p_o$, $p_f$ are parameter vectors associated with peephole connections. The functions $\sigma$ and $\phi$ are the logistic sigmoid and hyperbolic tangent non-linearity, respectively. The operation $\odot$ represents element-wise multiplication of vectors.

Training of the diagnostic function can be performed using patient data collected from a plurality of patients. In some embodiments, the training data set can include data accumulated during animal trials. The training data set can be divided into three parts—a training set, which represents the real world use of the diagnostic function; a validation set, used for optimization of the parameters; and a test set for final evaluation of the diagnostic function. The patient data can include different sets of nodes. In some embodiments, a first set of nodes can include patient-specific data 320 obtainable from the patient's electronic health record (EHR). Such EHR data can include gender, age, weight, medical condition, mobility, or nutrition. The input values for this EHR data can be represented in the training process by variable weight parameters based on a number of medical/non-medical/general parameters. In some embodiments, a second set of nodes can include measurable patient-specific data 320 such as data obtainable from the pressure sensor 110 or through other measurements. For example, data types in the second set of nodes can include pressure data, temperature data, relative humidity (e.g., moisture) data, three-axis motion and/or accelerometer data, or bioimpedance data.

In some embodiments, the machine-learning algorithm can develop the diagnostic function as a Bayesian network. Bayesian networks present the advantage that their structures are interpretable, which enables greater intuitive understanding of the logic behind the model. In various embodiments, a range of scoring functions, search algorithms, and structure initialization methods can be used to develop the Bayesian network. Bayesian networks suitable for use with embodiments of the systems and methods described herein are described in more detail in "Predictive models for pressure ulcers from intensive care unit electronic health records using Bayesian networks" by Pacharmon Kaewprag et al., *BMC Medical Informatics and Decision Making* 2017, Volume 17 (supplement 2), Issue 65, pp. 81-91, the entire contents of which is incorporated herein by reference.

FIG. 19 illustrates a flowchart of a method to diagnose a pressure ulcer condition of a patient in accordance with various embodiments described herein. The method 1900 includes inputting patient data 320 into a patient electronic health record (EHR) system to identify initial pressure ulcer classifiers for the patient based on age, gender, weight, health status, mobility, and medication history (step 1902). At this point, it is possible to optionally perform a first machine learning analysis of initial patient data to generate a first pressure ulcer diagnostic function for the patient (step 1904). For example, a model for the diagnostic function can be built using various machine-learning techniques as described above. Initial measurements of the medical condition of the patient can be performed, including measurements of any existing pressure ulcer and optionally including an image, size, location, and values for Braden scale (step 1905). The initial measurement data can be inputted into the EHR. The initial measurement data can be used to modify the pressure ulcer diagnostic function for the patient (step 1906).

Sensor devices 110 as described above can be applied to the patient at one or more locations ($L_1$, $L_2$, $L_3$) to generate first sensor data ($d_1$, $d_2$, $d_3$) (step 1908). For example, the sensor devices 110 could be applied at a patient's heel, knee, ankle, buttocks, or other pressure points. Data acquired from the sensor devices 110 can be used to further modify the pressure ulcer diagnostic function ($f_1$, $f_2$, $f_3$ . . . ) specific to each sensor location ($L_1$, $L_2$, $L_3$ . . . ) on the patient based on processed sensor data (step 1910). At the same time, the method 1900 includes revising the data monitoring program on the sensor to periodically or continuously update the sensor data based upon the pressure ulcer diagnostic function (step 1912). In some optional embodiments, the method 1900 utilizes motion sensor data to condition the diagnostic sensor data transmitted to the data processor or handheld devices (step 1918). In other words, the motion sensor data can be analyzed concurrently with pressure or other sensor data to modify the pressure data, e.g., to minimize the effect of the pressure data in a real-time analysis when motion sensor data indicates that the patient is moving in such a way as to relieve the pressure on the sensor. In such a situation, it may be unnecessary to raise an alert to cause the person to be moved because they have already done so.

The method 1900 can include revising the machine learning module based on sensor data and querying a database based upon the revised machine learning module (step 1916). The pressure ulcer diagnostic function ($f_1$, $f_2$, $f_3$) specific to each location can then be revised based on the revised machine learning module (step 1920). Finally, a diagnosis of a pressure ulcer condition of the patient can be provided and/or the patient can be automatically moved in response to sensed data indicating the patient condition and using the revised pressure ulcer diagnostic function (step 1922).

Bioimpedance is the ability of biological tissue to impede an electric current, and is broadly used in body composition measurements and healthcare assessment systems. These systems non-invasively source a small amount of alternating current into human tissues and measure the resulting voltage. From the sourced current and measured voltage, one can determine the electrical properties of the underlying tissues. From an electrical standpoint, impedance (Z) is the effective resistance to an alternating current, is dependent on the frequency of the alternating current, and can be defined by its magnitude (|Z|) and phase angle ($\theta$). The relationships between Z, |Z|, and $\theta$ can be seen in equations 24-26. Bioimpedance is a complex quantity composed of resistance (R), which is primarily caused by total body water and reactance ($X_c$), that is caused by the capacitance of cell membranes:

$$Z = R + jX_c \tag{24}$$

$$|Z| = \sqrt{R^2 + X_c^2} \tag{25}$$

$$\theta = \tan^{-1}\left(\frac{X_c}{R}\right) \tag{26}$$

Tissue impedance measurements vary based on a variety of factors including measurement frequency, electrode material, electrode size, tissue composition, distance between electrodes, and whether the electrode is gelled or not. For living tissues, there are three distinct frequency-dependent regions known as the $\alpha$, $\beta$, and $\gamma$-dispersions. In bioimpedance-based healthcare systems, frequencies in the $\beta$-dispersion (few kHz up to 1 MHz) are targeted since the $\beta$-dispersion is primarily caused by structural changes to cell membranes and can indicate pathological status.

The use of electrical parameters in order to predict development of pressure injuries can, for example, use subepidermal moisture (SEM) as an early indicator of pressure injury development. SEM is a measure of skin and other tissue's hydration, which is directly proportional to its ability to hold charge, or capacitance. Inflammation, which is typically the earliest sign of an impending pressure injury, can be detected via SEM 3 to 10 days before visual symptoms of a pressure injury.

There is a correlation between bioimpedance measurements with the development of pressure injury pathophysiology. A pressure injury model that bioimpedance measurements (impedance magnitude and phase angle) change as pressure injuries develop can be used. An impedance analyzer connected to an electrode array can be used to measure the bioimpedance of rats for days after pressure injuries were caused by placing a raised section of skin between two magnets for several hours. The resulting bioimpedance measurements correlated with pressure injury development, thereby indicating that inflammatory processes beneath the skin's surface progressively change the electrical properties of living tissues. A maximum correlation can occur at a measurement frequency of around 15 kHz, for example. Note that bioimpedance measurements can be dependent on electrode proximity to an existing pressure injury. Where electrode sets were placed close-to and far-from an existing pressure injury, the proximity of the electrodes strongly correlates with the pressure injury site, demonstrating that inflammatory processes change the electrical properties of the underlying tissues and can be measured via bioimpedance.

Bioimpedance provides information regarding the underlying tissue composition and compression state. Compared to the other metrics implemented for measuring pressure ulcers (pressure, temperature, humidity), this is the first to measure a property of the tissue itself. It is well known that different tissue types are affected at differing rates when an external load is applied to the body and this must be taken into account in a system that attempts to predict pressure ulcer likelihood.

Bioimpedance can be used to measure the comparative impedance magnitude and phase changes before, during, and after tissue compression. In this way, the system can compare the effect of tissue loading on the tissue's electrical properties and predict the amount of strain. For example, if a tissue sample exhibits high external force measured by the pressure sensor but had low strain, it can imply that the tissue is maximally compressed and is at higher risk of damage. On the other hand, a high force and a high strain can indicate that a compliant tissue or one that is not over a bony prominence. By multiplexing an array of bioimpedance electrodes the system obtains better spatial resolution as well as implement additionalimpedance comparison methods. Multiple electrodes allow the impedance from multiple sites to be compared to each other and an analysis of healthy versus at-risk tissue.

Figure 20:
FIG. 20 illustrates a further preferred embodiment of a sensor device to be applied to one or more locations on a patient

FIG. 20 illustrates a sensor device 110 that includes bioimpedance electrodes 202 and a motion sensor 204. The bioimpedence electrodes 202 can be connected to a driver in the control circuitry to drive current across a tissue spanning the electrodes at multiple frequencies. Sensed impedance data can be sent processed on board the sensor device 110 in some embodiments or can be transmitted to a server or other computing device wirelessly using the antenna 119 in some embodiments.

The sensor device 110 also includes the motion sensor 204. The motion sensor 204 can detect acceleration (e.g., magnitude and direction) in some embodiments. For example, the motion sensor 204 can include a 3-axis MEMs accelerometer. Data provided by the motion sensor 204 can be used alone or in conjunction with time-series data provided by other sensors. Motion data can be integrated with other sensor data to condition the sensor data in various embodiments. Information about recent motion by the patient can modify the severity of the diagnosis. For example, a patient who has recently moved to alleviate a building amount of pressure on a particular part of the tissue may not require an alert to be issued to require the patient to move. For a given patient the diagnostic function can modify the weighting coefficient for the pressure sensor data based on a correlation with the sensed movement of the sensor, for example. A reduction (or increase) in the weighting coefficient for one or more sensor elements can thus be facilitated or constrained based on the motion data. The combination of the weighted pressure sensor and motion sensor data can be used to notify the patient or caregiver that some body movement is needed or can automatically instruct a robotic bed assembly or other patient movement device to adjust a position of the patient.

Figure 21:
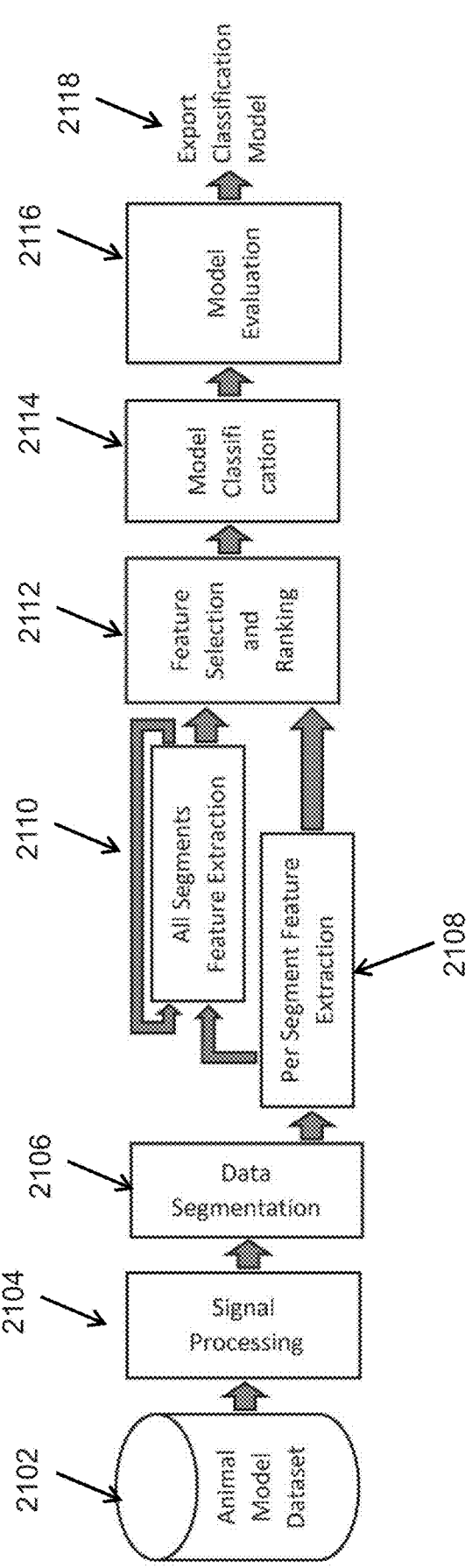
FIG. 21 illustrates a flow diagram for data collection, feature extraction, and classification.

FIG. 21 illustrates a flow diagram for data collection, feature extraction, and classification. Data from one or more sensor devices can also be processed in real time during sequential time intervals using the data processor mounted with the sensor device or using a second data processor that is external to the sensor device such as a mobile phone, a table, or a networked computer. To generate a classification model, a model dataset 2102 is provided. The model dataset 2102 may comprise data from humans or non-human animals. The model dataset 2102 may be acquired using sensor devices 110 as described herein, for example, with respect to FIG. 2A-2B, 12A-12B, or 20. In an exemplary embodiment, the model dataset 2102 is a data sequence acquired at a frequency of 2 Hz for an interval in a range of between four and six hours.

The model dataset 2102 is processed by a signal processing module 2104. Signal processing processes can include averaging or smoothing, for example. The processed data from the signal processing module 2104 is then segmented using a data segmentation module 2106. For example, the data sequence of the model dataset 2102 can be divided into equal segments of 30 minutes each in some implementations. In some embodiments, the segment length is selected so that high pressure can be detected promptly and a caregiver alerted if the process detects a risk of pressure ulcer formation.

The segmented data from the data segmentation module 2106 undergoes feature extraction using a per segment feature extraction module 2108. For example, time, frequency, and statistical features can be extracted for each segment of the total interval in some embodiments. In some embodiments, additional feature extraction can be performed iteratively using an all segments feature extraction module 2110. For example, a moving average can be calculated for a feature in the all segments feature extraction module 2110. In some embodiments, accumulated features over all segments (e.g., calculated by the mean of the moving average) can have greater importance and contribute more to model performance as compared to features calculated for only a single segment. In some embodiments, the all segments feature extraction module 2110 computes a value for each segment that includes data from that segment and from all segments acquired prior to that segment. The per segment feature extraction module 2108 and the all segments feature extraction module 2110 can be performed using periodically or continuously updated sensor data acquired as in the method flow illustrated in FIG. 19 and described above.

The extracted features are used to develop classification models to predict severity of a pressure ulcer (among other possible diagnostics). In some embodiments, machine learning classification algorithms such as Random Forest, Bagged Trees, support vector machine (SVM), and k-nearest neighbors (KNN) can be used to build a model to predict the severity of a pressure ulcer based on the intensity and distribution of the pressure captured by the extracted features. In preferred embodiments, ensemble algorithms can be utilized due to their ability to identify nonlinear relationships in the feature space. Statistical analysis and classification of the pressure sensor readings using a flow diagram such as in FIG. 21 can be performed using, e.g., MATLAB (The Mathworks, Inc., Natick, MA).

Extracted features from the data, whether from the per segment feature extraction module 2108 or the all segments feature extraction module 2110, can be selected and ranked using a feature selection and ranking module 2112. Once the data features are selected and ranked, machine learning models can be synthesized to classify the levels of pressure ulcer. Model classification is performed using a model classification module 2114. The models are evaluated using a model evaluation module 2116. For examples, models can be evaluated in terms of one or more of model precision, model accuracy, and area under the curve. The performance of classification models can be evaluated using 10-folds cross-validation, which most evenly distributes data in testing folds. Cross-validation can be performed by partitioning data into 10 disjoint folds at the population level. For each fold, the model can be trained using the out-of-fold observations. The model performance can then be assessed using the in-fold data. The average performance metrics can be calculated for all the folds. The highest-performing model for a given selected metric is exported from the model evaluation module 2116 to become the classification model 2118 used to monitor data in live data monitoring applications.

Feature generation and selection on a per segment of all segments basis is important to determine which features of the model dataset 2102 contribute the greatest amount to improving model characteristics and predictiveness. In an exemplary embodiment, up to 21 per segment features and 21 cumulative (all segments) features can be evaluated. Table 2 includes definitions and descriptions of several features. Feature selection can be performed by calculating feature importance. The importance of features is a measure of the relative contribution of each feature to the accuracy of the classifier. In certain embodiments, the ensemble model uses decision trees with high variance and low bias as base learners. At each node of the decision tree, the split feature is found based on information gain or the more computationally low-cost Gini impurity reduction method. The information gains due to a feature summed across all the levels of decision trees determines its feature importance. Each of the plurality of features can comprise an analytic function to determine a metric function or value. The metric enables ranking of the system output and can provide quantitative indicators of system accuracy. Random forest and bagged trees are composed of multiple decision trees, and thus the importance of a feature is the normalized sum of the information gain delivered by that feature across all trees. The output of these separate trees is aggregated and returned as the final ensemble result. The output of these separate trees is aggregated and returned as the final ensemble result.

TABLE 2

| Feature | Feature Definition | Description |
|---|---|---|
| Skewness | $$\dfrac{\dfrac{1}{n}\sum (x_i - \mu_x)^3}{\left[\dfrac{1}{n}\sum (x_i - \mu_x)^2\right]^{3/2}}$$ | Asymmetry of the signal distribution |
| Minimum and Maximum Difference | $\max(x_i) - \min(x_i)$ | Global maximum minus global minimum of the signal of one subject |
| Root Mean Square | $$\sqrt{\frac{1}{n}\sum x_i^2}$$ | Root Mean Square is a statistical measure |
| Entropy Rate | $-\Sigma\,possibility_{unique\ freq} \times \log_2(possibility_{unique\ freq})$ | The uncertainty measure of the signal, and the regularity of a signal when it is anticipated that consecutive data points are related |
| Kurtosis | $$\dfrac{\dfrac{1}{n}\sum (x_i - \mu_x)^4}{\left[\dfrac{1}{n}\sum (x_i - \mu_x)^2\right]^{2}}$$ | The extent to which the distribution of signal amplitudes lies predominantly on the left of the mean amplitude |
| Standard Deviation | $$\sqrt{\frac{1}{n}\sum (x_i - \mu_x)^2}$$ | Measure for signal spreading, defined as the square of standard deviation |
| Harmonic Ratio | $$\dfrac{\sum_{i=1,3,5\ldots} V_i}{\sum_{j=2,4,6\ldots} V_j}$$ | Harmonic Ratio quantifies the harmonic composition of the signal via discrete Fourier transform (DFT) |
| Average Power | $$\dfrac{total\ power\ of\ the\ signal}{bandwidth\ of\ the\ signal}$$ | The mean of the total power underneath the curve of the PSF estimate for a signal |
| The ratio of Spectral Peak | $$\dfrac{\max(power_{freq})}{\mathrm{mean}(power_{freq})}$$ | The ratio of the energies of low and high-frequency bands |
| Signal to Noise Ratio | $$\dfrac{power_{signal}}{power_{noise}}$$ | Power of the whole signal over the power of the computed noise |
| Total Harmonics Distortion | $$\dfrac{\sqrt{\sum_{i=2,3,4,5} V_i^2}}{V_1}$$ | The distortion of the whole signal when compared to its harmonics |
| Peak Frequency | $\max(power_f)$ | The maximum spectral power |
| Spectral Centroid | $$\dfrac{\times power_f^2}{\sum power_f^2}$$ | The frequency that divides the spectral power distribution into two equal parts. |
| Bandwidth | $$\dfrac{\sum (f - spectralCentroid)^2 \times power_f^2}{\sum power_f^2}$$ | The difference between the uppermost and lowermost frequencies/range of frequencies in the signal (weighted average) |
| Moment (order) | $$\frac{1}{n}\sum (x_i - \mu_x)^{order}$$ | Mean, variance, skew, kurtosis |

A further machine learning module that can be implemented to improve patient specific diagnostic function that can discern between pressure ulcers and regular tissue uses a boosting model such as an AdaBoost algorithm. AdaBoost selects the set of features that optimally discern between ulcers and normal tissue, as well as the set of weights that optimally combine such features and a set of thresholds for parameters by minimizing the empirical error on a training dataset. More precisely, AdaBoost learns the function:

$$f(x) = \sum_{t=}^{T} \alpha_t h_t(x),$$

where $h_t(x)$ is a weak classifier and corresponds to:

$$h_r(x) = \begin{cases} -1 & \text{if } \int_{a_1} g_0(I(x))dx > thr \\ 1 & \text{otherwise} \end{cases}$$

It is explicitly contemplated that the systems and methods presented herein may include one or more programmable processing units having associated therewith executable instructions held on one or more of a computer readable medium, RAM, ROM, hard drive, and/or hardware. In exemplary embodiments, the hardware, firmware and/or executable code may be provided, for example, as upgrade module(s) for use in conjunction with existing infrastructure (for example, existing devices/processing units). Hardware may, for example, include components and/or logic circuitry for executing the embodiments taught herein as a computing process, e.g., for controlling the frequency of data sampling from the one or more sensors.

Figure 22:
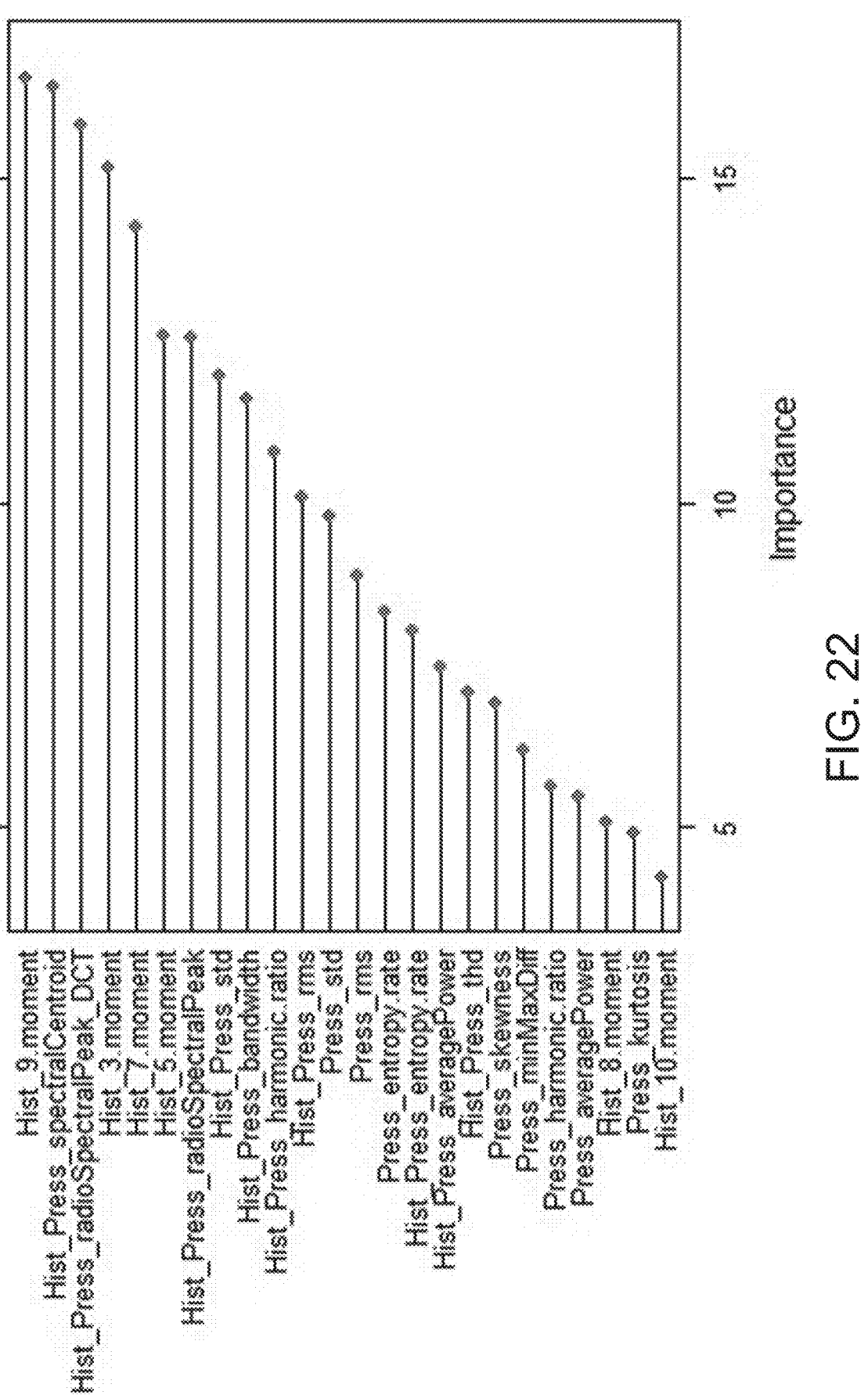
FIG. 22 illustrates ranked feature importance for a selected set of features in an exemplary classification model according to embodiments described herein.

FIG. 22 illustrates the feature importance for a selected set of features. Features in FIG. 22 with "Hist" preceding the feature name denote features calculated as a moving average over several segments (i.e., all segments feature extraction and evaluation as described above). The three most important features in this implementation of the model generation and evaluation were the $9^{th}$ Moment, Spectral Centroid, and Spectral Peak. Note that the average ("Hist") features dominate the top selected features for this particular model which indicates the importance of considering historical (previous) measurements of pressure when predicting pressure ulcer severity.

In an exemplary implementation, extracted features can be classified into the labeled pressure ulcer classes (0, 2, and 2-deep) and the accuracy of various classification models based on different algorithms such as bagged trees, random forest, SVM, and KNN can be compared. Exemplary results of this process are shown in Table 3.

TABLE 3

| ML model | Accuracy | Precision | Recall | Area under Curve (AuC) |
|---|---|---|---|---|
| Random Forest | 92.1% | 90.3% | 88.5% | 0.95 |
| Bagged Trees | 88.7% | 85.3% | 72.3% | 0.94 |
| Quadratic SVM | 85.2% | 77.3% | 63.0% | 0.68 |
| Weighted KNN | 84.5% | 68.3% | 56.7% | 0.88 |
| Naïve Bayes | 84.3% | 69.1% | 72.1% | 0.86 |

Software operating these models is available commercially from The Mathworks, Inc., Natick, MA, including Matlab® and Simulink® products, for example. The Matlab® machine learning toolbox, for example, can enable the use of random forest, bagged trees, and boosting algorithms that can be applied to data using a plurality of weak classifiers.

Figure 23:
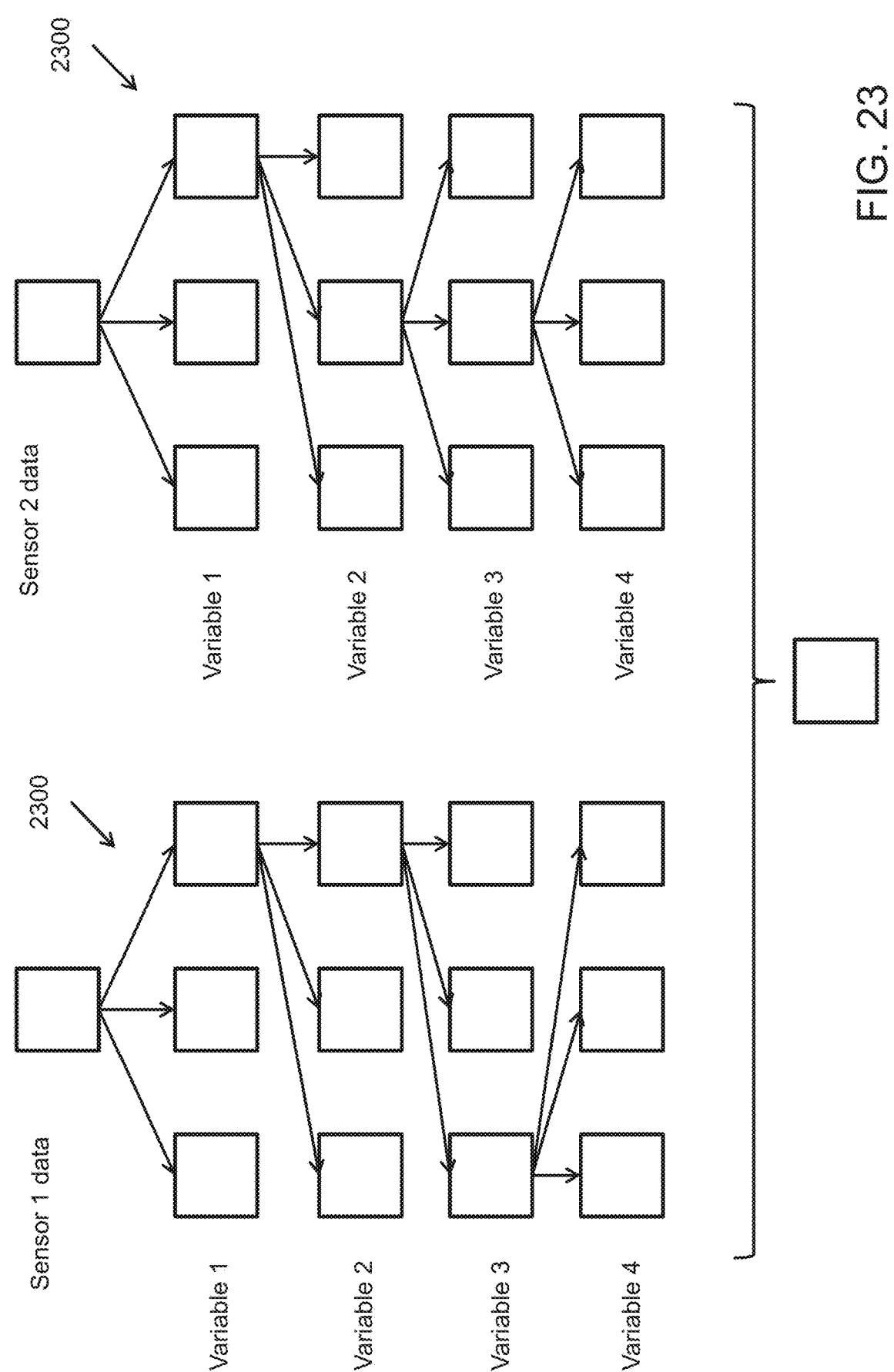
FIG. 23 illustrates a schematic view of ensemble averaging from multiple separate decision trees according to embodiments described herein.

FIG. 23 illustrates a schematic view of ensemble averaging from multiple separate decision trees according to various embodiments. Each decision tree 2300 represents a family of related classification models where each edge level represents a data input such as measurements from a sensor device or other vital statistics related to a patient as described above. For example, the first decision tree 2300 can be based upon data acquired from a first sensor (e.g., located at a first body location) while the second decision tree 2300 can be based upon data acquired from a second sensor (e.g., located at a second body location). Variables 1-4 can include data categories such as age, body mass, blood pressure, and blood oxygenation, or other data categories including those described above in relation to, e.g., FIG. 4. The different models within each edge level extract a different feature from the relevant data for that edge level. The resulting model that is most successful in predicting the data outcomes is then propagated to the next edge level. In some embodiments, ensemble averaging can be used to process results from the resulting model from each of a plurality of decision trees. Although only two decision trees 2300 are depicted in FIG. 23, the analysis can make use of many more than two decision trees in generating the ensemble averaged information.

While the present inventive concepts have been described with reference to particular embodiments, those of ordinary skill in the art will appreciate that various substitutions and/or other alterations may be made to the embodiments without departing from the spirit of the present inventive concepts. Accordingly, the foregoing description is meant to be exemplary and does not limit the scope of the present inventive concepts.

A number of examples have been described herein. Nevertheless, it should be understood that various modifications may be made. For example, suitable results may be achieved if the described techniques are performed in a different order and/or if components in a described system, device, or method are combined in a different manner and/or replaced or supplemented by other components or their equivalents. Accordingly, other implementations are within the scope of the present inventive concepts.

The invention claimed is:

1. A method of determining a pressure ulcer condition of a patient comprising:

entering patient data with a pressure ulcer monitoring system, the system configured to perform computational operations on measured pressure sensor data at a selected tissue surface location on the patient, the computational operations including computing a diagnostic value of a pressure ulcer diagnostic function of the patient using the patient data and the measured pressure sensor data at the selected tissue surface location;

detecting pressure data with a sensor patch device having a pressure sensor with a pressure sensitive area at the selected tissue surface location on the patient wherein the sensor patch device is powered by a battery and includes a control circuit and a wireless transmitter that transmits measured pressure sensor data above a threshold value to an external data processing device, the pressure sensor comprising an array of pressure sensor elements defining the pressure sensitive area that is attached to skin of the patient at the selected tissue surface location with an adhesive; and automatically computing the diagnostic value with the external data processing device using an accumulated value of the measured pressure sensor data at each pressure sensor element of the array of pressure sensor elements sensing pressure above the threshold value during a controlled time interval and detected with the array of pressure sensor elements and processed using the pressure ulcer diagnostic function that includes the selected tissue surface location on the patient and a plurality of patient characteristics including the weight of the patient.

2. The method of claim 1 wherein the step of detecting pressure data with the sensor patch device further comprises attaching a first conformable patch at the tissue surface a location on the patient, the sensor patch device including at least one of a temperature sensor, a humidity sensor and a bioimpedance sensor and a flexible circuit device connected to the sensor patch device, the flexible circuit device including the wireless transmitter.

3. The method of claim 1, wherein the computational operations include processing pressure ulcer data sensed using a pressure sensor patch on a heel of a foot of the patient with a machine learning module that comprises at least one of a support vector machine, a neural network or a Bayesian network.

4. The method of claim 1 wherein the computational operations include processing pressure ulcer data with a machine learning module that comprises one or more decision trees based on an age of the patient, a medication of the patient, the tissue surface location of the pressure sensor on the patient, and a blood pressure of the patient.

5. The method of claim 1, further comprising sensing one or more of a temperature, a humidity, or an orientation at the tissue surface location with the sensor patch device.

6. The method of claim 3, wherein the learning module operates a bagged tree program or a random forest program or wherein the learning module comprises a boosting algorithm, or wherein the learning module processes a plurality of weak classifiers.

7. The method of claim 1, further comprising processing at least one of the patient data and the pressure data with a machine learning module having one or more analytic features to compute one or more metrics wherein the learning module segments the sensed data, selects one or more features, and ranks a metric value for the one or more features.

8. The method of claim 1 further comprising controlling transmission of pressure sensor data above the threshold for each pressure sensor element with the control circuit mounted on a circuit board within the sensor patch device.

9. The method of claim 1 wherein detecting pressure data comprises measuring pressure with each pressure sensor element of the array of pressure sensor elements, each pressure sensor element comprising a resistive pressure sensing element.

10. The method of claim 1 wherein detecting pressure data comprises measuring pressure with each pressure sensor element of the array of pressure sensor elements, each pressure sensor element comprising a capacitive pressure sensing element.

11. The method of claim 1 wherein the detecting step further comprises recording a time of each pressure measurement with the array of pressure sensor elements.

12. The method of claim 1 further comprising recording a location of the sensor patch device on the patient during the step of detecting pressure data.

13. The method of claim 1 further comprising entering the patient data using a data processor that wirelessly communicates with the sensor patch device.

14. The method of claim 1 further comprising time stamping the measured pressure sensor data for wireless transmission.

15. The method of claim 14 further comprising wirelessly transmitting a location data with the time stamped measured pressure sensor data.

16. The method of claim 14 further comprising wirelessly transmitting temperature data with the time stamped measured pressure sensor data.

17. The method of claim 1 wherein the array of pressure sensing elements comprises a two dimensional array.

18. The method of claim 1 wherein the sensor patch device has a thickness of less than 4 mm and includes seal and an adhesive layer to attach to skin of the patient.

19. The method of claim 1 wherein the sensor patch device further comprises a power management circuit connected to the battery.

20. The method of claim 13 wherein the value of the pressure ulcer diagnostic function can exceed a threshold value whereby the data processor transmits a signal to communicate a change of patient condition to a user.

21. The method of claim 1 wherein the wireless transmitter further comprises an antenna.

* * * * *